(12) United States Patent
Sperl et al.

(10) Patent No.: US 8,246,594 B2
(45) Date of Patent: Aug. 21, 2012

(54) ABSORBENT ARTICLE HAVING AN ABSORBENT STRUCTURE CONFIGURED FOR IMPROVED DONNING AND LATERAL STRETCH DISTRIBUTION

(75) Inventors: Michael D. Sperl, Waupaca, WI (US); Davis Dang Hoang Hhan, Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 1175 days.

(21) Appl. No.: 11/026,423

(22) Filed: Dec. 30, 2004

(65) Prior Publication Data

US 2005/0256474 A1 Nov. 17, 2005

Related U.S. Application Data

(63) Continuation-in-part of application No. 10/835,638, filed on Apr. 30, 2004, now Pat. No. 7,993,319.

(51) Int. Cl.
*A61F 13/15* (2006.01)
*A61F 13/20* (2006.01)

(52) U.S. Cl. .............. 604/385.16; 604/385.201

(58) Field of Classification Search .......... 604/383, 604/385.101, 385.09, 385.19, 385.22, 385.01, 604/358, 385.16, 385.201; 428/103; 156/252
See application file for complete search history.

(56) References Cited

U.S. PATENT DOCUMENTS

| | | |
|---|---|---|
| 2,931,361 A | 4/1960 | Sostrin |
| 3,849,241 A | 11/1974 | Butin et al. |
| 3,921,638 A | 11/1975 | Schaar |
| 3,978,861 A | 9/1976 | Schaar |
| 4,036,233 A * | 7/1977 | Kozak .......................... 604/370 |
| 4,050,462 A | 9/1977 | Woon et al. |
| 4,100,324 A | 7/1978 | Anderson et al. |
| 4,205,679 A | 6/1980 | Repke et al. |
| 4,443,513 A | 4/1984 | Meitner et al. |
| 4,522,874 A | 6/1985 | Pommez |
| 4,560,372 A | 12/1985 | Pieniak |
| 4,573,986 A | 3/1986 | Minetola et al. |
| 4,631,062 A | 12/1986 | Lassen et al. |

(Continued)

FOREIGN PATENT DOCUMENTS

EP 0 217 032 A3 4/1987

(Continued)

OTHER PUBLICATIONS

International Search Report and Written Opinion for International Application No. PCT/US2004/004724, dated Aug. 3, 2004, 12 Pages.

(Continued)

*Primary Examiner* — Melanie Hand
(74) *Attorney, Agent, or Firm* — Armstrong Teasdale LLP

(57) ABSTRACT

An absorbent article generally has a longitudinal axis, a lateral axis, a front waist region, a back waist region, and a crotch region extending longitudinally between and interconnecting said front and back waist regions. The article comprises an outer cover stretchable in at least the lateral direction and a liner in opposed relationship with the outer cover and stretchable in at least the lateral direction. An absorbent structure is disposed between the liner and the outer cover and extends from the crotch region to at least one of the front waist region and the back waist region of the article. The article has an attachment zone and at least one non-attachment zone laterally adjacent the attachment zone. The absorbent structure is configured for improved lateral stretch distribution of the article.

23 Claims, 34 Drawing Sheets

U.S. PATENT DOCUMENTS

| | | | |
|---|---|---|---|
| 4,642,110 A | 2/1987 | Dudek | |
| 4,657,802 A | 4/1987 | Morman | |
| 4,663,220 A | 5/1987 | Wisneski et al. | |
| 4,704,114 A | 11/1987 | Wilson et al. | |
| 4,704,116 A | 11/1987 | Enloe | |
| 4,710,187 A | 12/1987 | Boland et al. | |
| 4,720,415 A | 1/1988 | Vander Wielen et al. | |
| 4,731,066 A | 3/1988 | Korpman | |
| 4,747,846 A | 5/1988 | Boland et al. | |
| 4,752,349 A | 6/1988 | Gebel | |
| 4,753,646 A | 6/1988 | Enloe | |
| 4,756,709 A | 7/1988 | Stevens | |
| 4,808,176 A | 2/1989 | Kielpikowski | |
| 4,834,736 A | 5/1989 | Boland et al. | |
| 4,846,823 A | 7/1989 | Enloe | |
| 4,854,995 A | 8/1989 | Kasper et al. | |
| 4,865,597 A | 9/1989 | Mason, Jr. et al. | |
| 4,874,451 A | 10/1989 | Boger et al. | |
| 4,892,536 A | 1/1990 | DesMarais et al. | |
| 4,935,021 A | 6/1990 | Huffman et al. | |
| 4,938,755 A | 7/1990 | Foreman | |
| 4,940,464 A | 7/1990 | Van Gompel et al. | |
| 4,965,122 A | 10/1990 | Morman | |
| 4,981,747 A | 1/1991 | Morman | |
| 4,990,147 A | 2/1991 | Freeland | |
| 5,026,364 A | 6/1991 | Robertson | |
| 5,037,416 A | 8/1991 | Allen et al. | |
| 5,046,272 A | 9/1991 | Vogt et al. | |
| 5,104,116 A | 4/1992 | Pohjola | |
| 5,108,385 A | 4/1992 | Snyder | |
| 5,114,781 A | 5/1992 | Morman | |
| 5,116,662 A | 5/1992 | Morman | |
| 5,151,092 A | 9/1992 | Buell et al. | |
| 5,224,405 A | 7/1993 | Pohjola | |
| 5,226,992 A | 7/1993 | Morman | |
| 5,244,482 A | 9/1993 | Hassenboehler, Jr. et al. | |
| 5,269,775 A | 12/1993 | Freeland et al. | |
| 5,284,703 A | 2/1994 | Everhart et al. | |
| 5,295,987 A | 3/1994 | Widlund et al. | |
| 5,340,424 A | 8/1994 | Matsushita | |
| 5,350,624 A | 9/1994 | Georger et al. | |
| 5,356,405 A | 10/1994 | Thompson et al. | |
| 5,368,584 A | 11/1994 | Clear et al. | |
| 5,397,316 A | 3/1995 | LaVon et al. | |
| 5,397,317 A | 3/1995 | Thomas | |
| 5,462,537 A | 10/1995 | Carr et al. | |
| 5,486,166 A | 1/1996 | Bishop et al. | |
| 5,490,846 A | 2/1996 | Ellis et al. | |
| 5,503,076 A | 4/1996 | Yeo | |
| 5,554,143 A | 9/1996 | Roe et al. | |
| 5,567,265 A | 10/1996 | Zajaczkowski | |
| 5,593,401 A | 1/1997 | Sosalla et al. | |
| 5,611,790 A | 3/1997 | Osborn, III et al. | |
| 5,624,422 A | 4/1997 | Allen | |
| 5,634,916 A | 6/1997 | LaVon et al. | |
| 5,643,242 A | 7/1997 | LaVon et al. | |
| 5,645,542 A | 7/1997 | Anjur et al. | |
| 5,658,269 A | 8/1997 | Osborn, III et al. | |
| 5,681,302 A | 10/1997 | Melbye et al. | |
| 5,690,627 A | 11/1997 | Clear et al. | |
| 5,695,868 A | 12/1997 | McCormack | |
| 5,766,389 A | 6/1998 | Brandon et al. | |
| 5,804,021 A * | 9/1998 | Abuto et al. | 156/252 |
| 5,817,086 A | 10/1998 | Kling | |
| 5,820,973 A | 10/1998 | Dodge, II et al. | |
| 5,843,056 A | 12/1998 | Good et al. | |
| 5,846,232 A | 12/1998 | Serbiak et al. | |
| 5,873,868 A * | 2/1999 | Nakahata | 604/383 |
| 5,883,028 A | 3/1999 | Morman et al. | |
| 5,925,026 A | 7/1999 | Arteman et al. | |
| 5,928,211 A | 7/1999 | Gustafsson et al. | |
| 5,947,947 A | 9/1999 | Tanzer et al. | |
| 5,957,907 A | 9/1999 | Sauer | |
| 5,964,743 A | 10/1999 | Abuto et al. | |
| 5,997,981 A | 12/1999 | McCormack et al. | |
| 6,049,915 A | 4/2000 | Malowaniec | |
| 6,093,870 A | 7/2000 | Carlsson | |
| 6,103,953 A | 8/2000 | Cree et al. | |
| 6,120,485 A | 9/2000 | Gustafsson et al. | |
| 6,129,720 A | 10/2000 | Blenke et al. | |
| 6,132,411 A | 10/2000 | Huber et al. | |
| 6,149,638 A | 11/2000 | Vogt et al. | |
| 6,149,934 A | 11/2000 | Krzysik et al. | |
| 6,152,906 A | 11/2000 | Faulks et al. | |
| 6,160,197 A | 12/2000 | Lassen et al. | |
| 6,174,303 B1 | 1/2001 | Suprise et al. | |
| 6,193,701 B1 | 2/2001 | Van Gompel et al. | |
| 6,217,563 B1 | 4/2001 | Van Gompel et al. | |
| 6,231,557 B1 | 5/2001 | Krautkramer et al. | |
| 6,262,331 B1 | 7/2001 | Nakahata et al. | |
| 6,264,639 B1 | 7/2001 | Sauer | |
| 6,264,641 B1 | 7/2001 | Van Gompel et al. | |
| 6,312,786 B1 | 11/2001 | Schwinn | |
| 6,362,389 B1 | 3/2002 | McDowall et al. | |
| 6,409,711 B1 | 6/2002 | Jonbrink | |
| 6,413,247 B1 | 7/2002 | Carlucci et al. | |
| 6,461,338 B1 | 10/2002 | Shimoe et al. | |
| 6,482,191 B1 | 11/2002 | Roe et al. | |
| 6,521,811 B1 | 2/2003 | Lassen et al. | |
| 6,552,245 B1 | 4/2003 | Roessler et al. | |
| 6,570,056 B1 | 5/2003 | Tanzer et al. | |
| 6,572,598 B1 | 6/2003 | Ashton et al. | |
| 6,582,414 B1 | 6/2003 | Richardson | |
| 6,610,383 B1 | 8/2003 | Morman et al. | |
| 6,623,465 B1 | 9/2003 | Roe et al. | |
| 6,632,212 B1 | 10/2003 | Morman et al. | |
| 6,641,568 B2 | 11/2003 | Ashton et al. | |
| 6,645,190 B1 | 11/2003 | Olson et al. | |
| 6,667,424 B1 | 12/2003 | Hamilton et al. | |
| 6,679,869 B1 | 1/2004 | Schlinz et al. | |
| 6,682,512 B2 | 1/2004 | Uitenbroek et al. | |
| 6,695,827 B2 | 2/2004 | Chen et al. | |
| 6,702,799 B2 | 3/2004 | Otsubo | |
| 6,702,800 B1 | 3/2004 | Vukos et al. | |
| 6,703,538 B2 | 3/2004 | Lassen et al. | |
| 6,706,028 B2 | 3/2004 | Roe et al. | |
| 6,755,808 B2 | 6/2004 | Balogh et al. | |
| 7,011,653 B2 | 3/2006 | Imsangjan et al. | |
| 2002/0013563 A1 | 1/2002 | Lassen et al. | |
| 2002/0029029 A1 | 3/2002 | Otsubo | |
| 2002/0052590 A1 | 5/2002 | Zehner et al. | |
| 2002/0058922 A1 | 5/2002 | Skog | |
| 2002/0099352 A1 | 7/2002 | Heden et al. | |
| 2002/0104608 A1 | 8/2002 | Welch et al. | |
| 2002/0111598 A1 | 8/2002 | Vogt et al. | |
| 2002/0165514 A1 | 11/2002 | Datta et al. | |
| 2003/0023213 A1 * | 1/2003 | Fernfors et al. | 604/359 |
| 2003/0088230 A1 | 5/2003 | Balogh et al. | |
| 2003/0125696 A1 | 7/2003 | Morman et al. | |
| 2004/0013850 A1 | 1/2004 | Kling | |
| 2004/0044323 A1 | 3/2004 | Roessler et al. | |
| 2004/0102749 A1 | 5/2004 | Olson et al. | |
| 2004/0127878 A1 | 7/2004 | Olson et al. | |
| 2004/0127881 A1 | 7/2004 | Stevens et al. | |
| 2005/0143710 A1 | 6/2005 | Van Gompel et al. | |
| 2005/0148987 A1 | 7/2005 | Van Gompel et al. | |

FOREIGN PATENT DOCUMENTS

| | | |
|---|---|---|
| EP | 0 603 748 A1 | 6/1994 |
| EP | 605 017 A2 | 7/1994 |
| EP | 0 835 088 B1 | 4/1998 |
| EP | 847 739 A2 | 6/1998 |
| EP | 0 951 886 A1 | 10/1999 |
| EP | 1 201 212 A3 | 5/2002 |
| EP | 1 219 274 A1 | 7/2002 |
| EP | 0 957 868 B1 | 2/2003 |
| EP | 1 310 224 A2 | 5/2003 |
| GB | 2284538 A | 6/1995 |
| GB | 2 305 610 A | 9/1996 |
| GB | 2310606 A | 9/1997 |
| JP | 2004 195244 A | 7/2004 |
| WO | WO 93/06805 A1 | 4/1993 |
| WO | WO 95/15410 A1 | 6/1995 |
| WO | WO 95/19753 A1 | 7/1995 |
| WO | WO 98/29239 A1 | 7/1998 |
| WO | WO 99/33426 A1 | 7/1999 |
| WO | WO 99/33427 A1 | 7/1999 |

| | | |
|---|---|---|
| WO | WO 00/37009 A3 | 6/2000 |
| WO | WO 01/88245 A2 | 11/2001 |
| WO | WO 02/34184 A1 | 5/2002 |
| WO | WO 02/069870 A2 | 9/2002 |
| WO | WO 02/096333 A2 | 12/2002 |
| WO | WO 03/051254 A2 | 6/2003 |
| WO | WO 03/057106 A1 | 7/2003 |
| WO | WO 2004/108041 A1 | 12/2004 |

OTHER PUBLICATIONS

"Polyethylene—Low Density (LDPE)—Material Information," Internet web page "http://www.goodfellow.com/csp/active/STATIC/E/Polyethylene_-_Low_Density.HTML", p. 3, line 1, Goodfellow Corporation, Devon, PA.

* cited by examiner

SAMPLE 3

SAMPLE 2

SAMPLE 1

SAMPLE 6

SAMPLE 5

SAMPLE 4

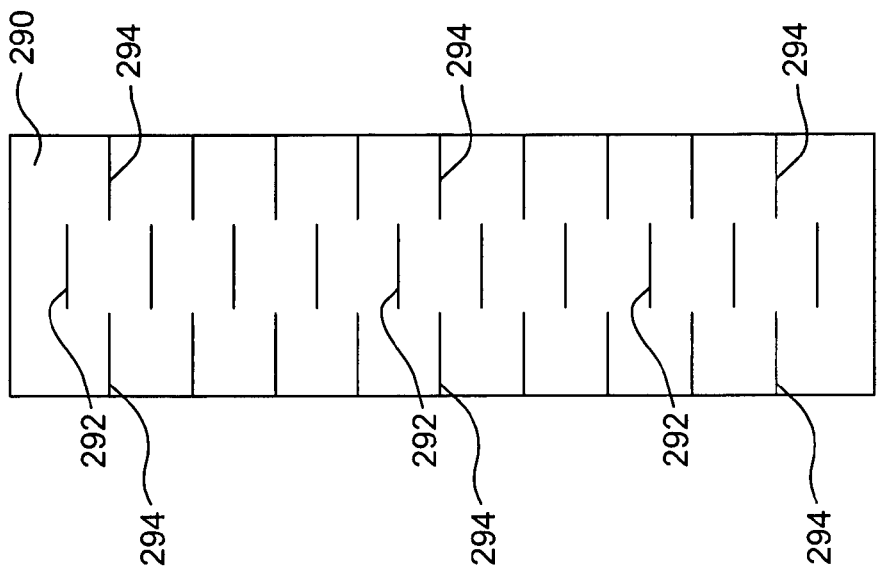
FIG. 20 SAMPLE 9
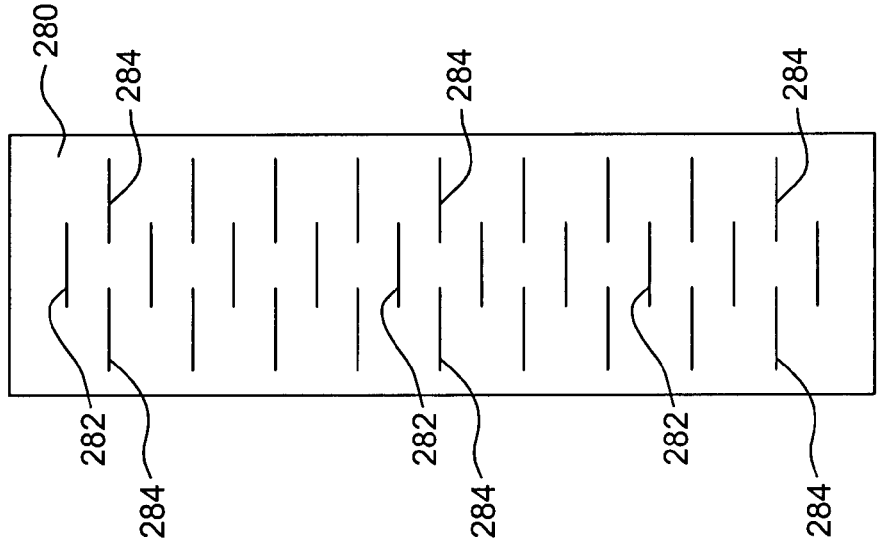
FIG. 19 SAMPLE 8
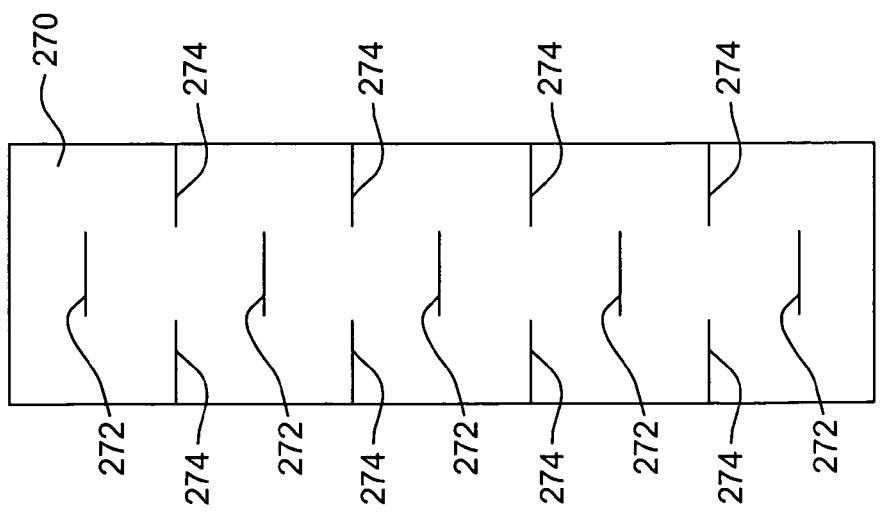
FIG. 18 SAMPLE 7

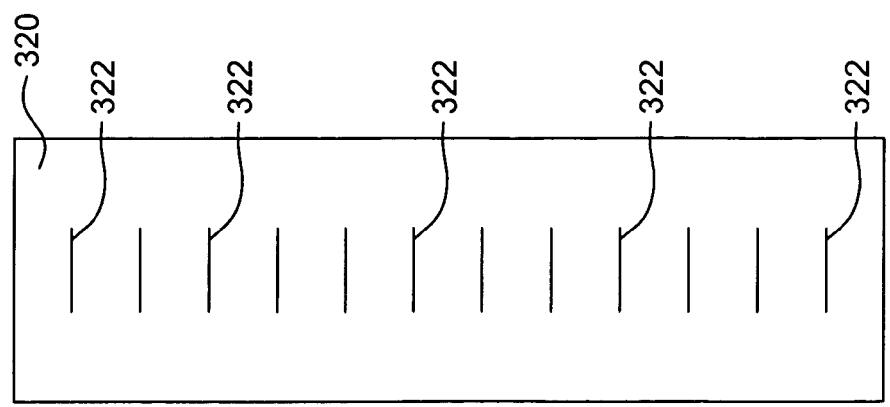
FIG. 27 SAMPLE 12
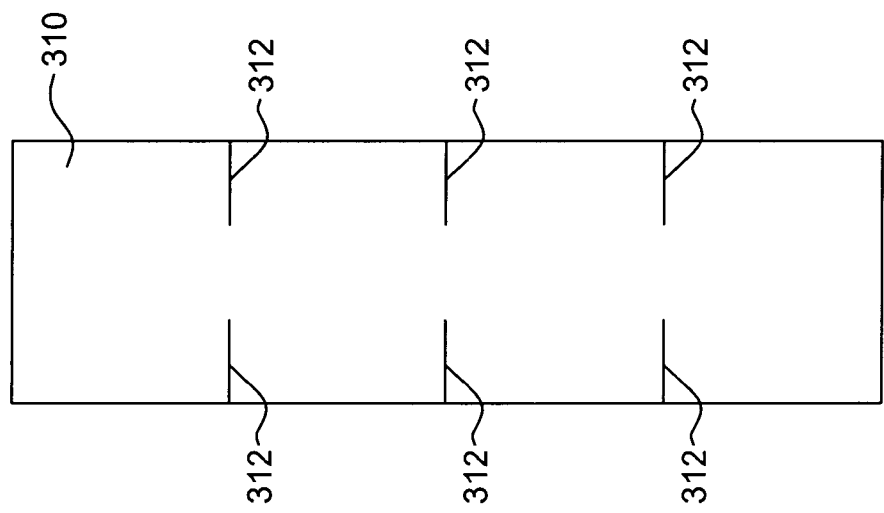
FIG. 26 SAMPLE 11
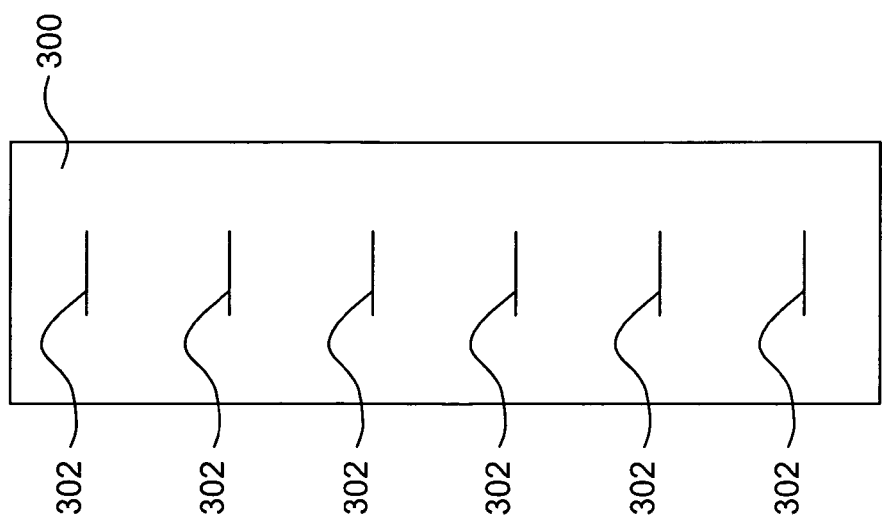
FIG. 25 SAMPLE 10

SAMPLE 13

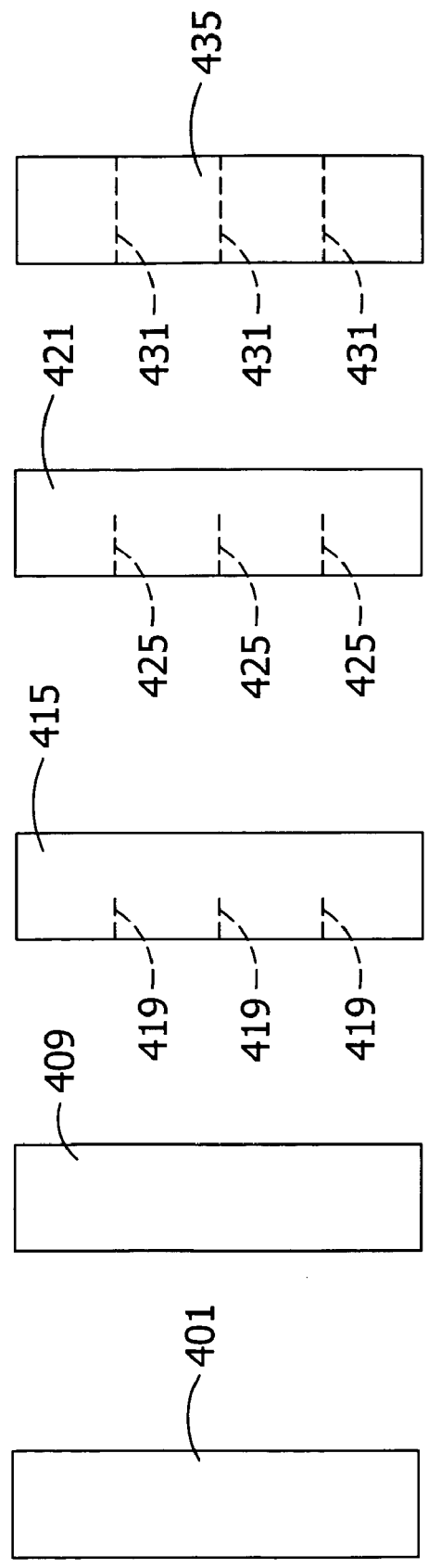

ABSORBENT ARTICLE HAVING AN ABSORBENT STRUCTURE CONFIGURED FOR IMPROVED DONNING AND LATERAL STRETCH DISTRIBUTION

CROSS-REFERENCE TO RELATED APPLICATIONS

This application is a continuation-in-part patent application of U.S. patent application Ser. No. 10/835,638 entitled Absorbent Article Having an Absorbent Structure Configured for Improved Donning of the Article, filed Apr. 30, 2004, the disclosure of which is fully incorporated herein by reference.

FIELD OF THE INVENTION

The present invention relates generally to absorbent articles intended for personal wear, and more particularly to an absorbent article having an absorbent structure configured to facilitate easier donning and improved lateral stretch distribution of the article.

BACKGROUND OF THE INVENTION

Absorbent articles such as diapers, training pants, incontinence garments, and the like conventionally include a liquid permeable body-facing liner, a liquid impermeable outer cover, and an absorbent core (also referred to as an absorbent body or absorbent structure) formed separate from the outer cover and liner and disposed therebetween for taking in and retaining liquid (e.g., urine) exuded by the wearer.

Absorbent articles may be designed with extensible or elastic components that improve donning, fit during wear, and removal of the article from the wearer. In some of these absorbent articles, the outer cover and/or the liner may be stretchable to permit some expansion of the article when necessary to provide a better fit on the wearer. For example, a child pulling on a pair of training pants typically pulls both upward on the pants and outward on the pants (e.g., at the waist) to widen the waist opening and pull the pants up over the buttocks and hips to the child's waist. Thus an expansion force is applied to the article to increase the dimensions thereof.

Typically, the absorbent structure of these articles is attached to the outer cover and/or liner to form an attachment zone of the article over which the stretchability of the outer cover and/or liner is inhibited by the less stretchable absorbent structure. The portion of the outer cover and liner that is not attached to the absorbent structure, the non-attachment zone, has a higher amount of stretchability than the attachment zone of the article.

The lateral stretch distribution of the absorbent article is the distribution of stretch across the lateral width of the absorbent article that is needed to expand the waist opening of the article. The distribution of stretch in the circumference of existing articles includes areas with little or no amount of stretch (e.g., the attachment zone) and areas with a relatively higher amount of stretch (e.g., the non-attachment zone) resulting in an uneven lateral stretch distribution in the article. The extension energy of an absorbent article (or a portion of an absorbent article) is defined as the amount of resistance to stretching in the article. The extension energy is inversely proportional to the amount of lateral stretch in the article so that a larger amount of extension energy means that the article will have increased resistance to stretching. An absorbent article having ideal lateral stretch distribution would have an equal lateral stretch distribution and equal extension energy in both the attachment zone and non-attachment zone of the article.

Each layer of material of the absorbent article adds extension energy and resistance to stretching to the outer cover and/or the liner and contributes to the expansion force required to expand the waist opening during donning. The uneven lateral stretch distribution across the circumference of the article requires that the article be made such that substantially all of the stretch needed to increase the circumference of the pant during donning occurs in the portions of the article having a high amount of stretch, typically the non-attachment zone. In existing absorbent articles, the absorbent structure must be reduced in size or made of reduced basis weight in order to reduce the size of the attachment zone, or increase the stretchability of the absorbent structure so as to improve the lateral stretch distribution across the lateral width of the article.

FIG. 32 shows a graph comparing the extension energy of a complete training pant, a stretchable outer cover and liner of the training pant (e.g., without the absorbent structure therebetween), and a stretchable absorbent structure of the training pant. The graph of FIG. 32 illustrates that the complete pant has significantly higher extension energy than both the outer cover and liner and the absorbent structure of the pant. Also, the results indicate that, as expected, the less stretchable absorbent structure contributes a larger amount of extension energy to the entire pant than the outer cover and liner. An ideal training pant design would include an extension energy that is as low as possible to allow elongation of the training pant at a decreased donning force of the article. Further, an ideal pant design would have equal lateral stretch distribution across the attachment zone and the non-attachment zone of the article.

There is a need, therefore, to improve the construction of the absorbent structure of the stretchable absorbent article to decrease the extension energy and the required donning force of the article and to improve the lateral stretch distribution of the article so that the absorbent article may be more easily donned, while maintaining the performance of the article.

SUMMARY OF THE INVENTION

In one embodiment, an absorbent article of the present invention generally has a longitudinal axis, a lateral axis, a front waist region, a back waist region, and a crotch region extending longitudinally between and interconnecting said front and back waist regions. The article comprises an outer cover stretchable in at least one direction and a liner in opposed relationship with the outer cover and stretchable in the at least one direction. An absorbent structure is disposed between the liner and the outer cover and extends from the crotch region to at least one of the front waist region and the back waist region of the article. The article has an attachment zone and a non-attachment zone. The absorbent structure has a ratio of extension energy in the non-attachment zone to the extension energy in the attachment zone of at least approximately 0.4 for a strain ranging from greater than 0% to approximately 80% as measured by a Material Elongation Tensile Test.

In another embodiment, the absorbent article generally comprises an outer cover stretchable in at least one direction and a liner in opposed relationship with the outer cover and stretchable in the at least one direction. An absorbent structure is disposed between the liner and the outer cover and extends from the crotch region to at least one of the front waist region and the back waist region of the article. The article has an attachment zone and a non-attachment zone. The absorbent structure has a ratio of elongation in the attachment zone to elongation in the non-attachment zone of at least approximately 0.3 for a tensile force of at least 200 grams as measured by a Material Elongation Tensile Test.

In yet another embodiment of the present invention an absorbent article has a longitudinal axis, a lateral axis, a front waist region, a back waist region, and a crotch region extending longitudinally between and interconnecting said front and back waist regions. The article comprises an outer cover stretchable in at least one direction and a liner in opposed relationship with the outer cover and stretchable in the at least one direction. A stretchable absorbent structure is disposed between the liner and the outer cover and extends from the crotch region to at least one of the front waist region and the back waist region of the article, the absorbent structure has at least two weakening elements disposed therein extending in the longitudinal direction for improved lateral stretch distribution across the lateral width of the article.

Other features of the invention will be in part apparent and in part pointed out hereinafter.

BRIEF DESCRIPTION OF THE DRAWINGS

FIGS. 12-20 illustrate eight samples of absorbent structure material that were tested in accordance with an experiment described herein;

FIGS. 25-28 illustrate four samples of absorbent structure material that were tested in accordance with a second experiment described herein;

FIGS. 33-37 illustrate test samples that were tested in accordance with a third experiment described herein;

Corresponding reference characters indicate corresponding parts throughout the several views of the drawings.

DETAILED DESCRIPTION OF THE INVENTION

Figure 1:
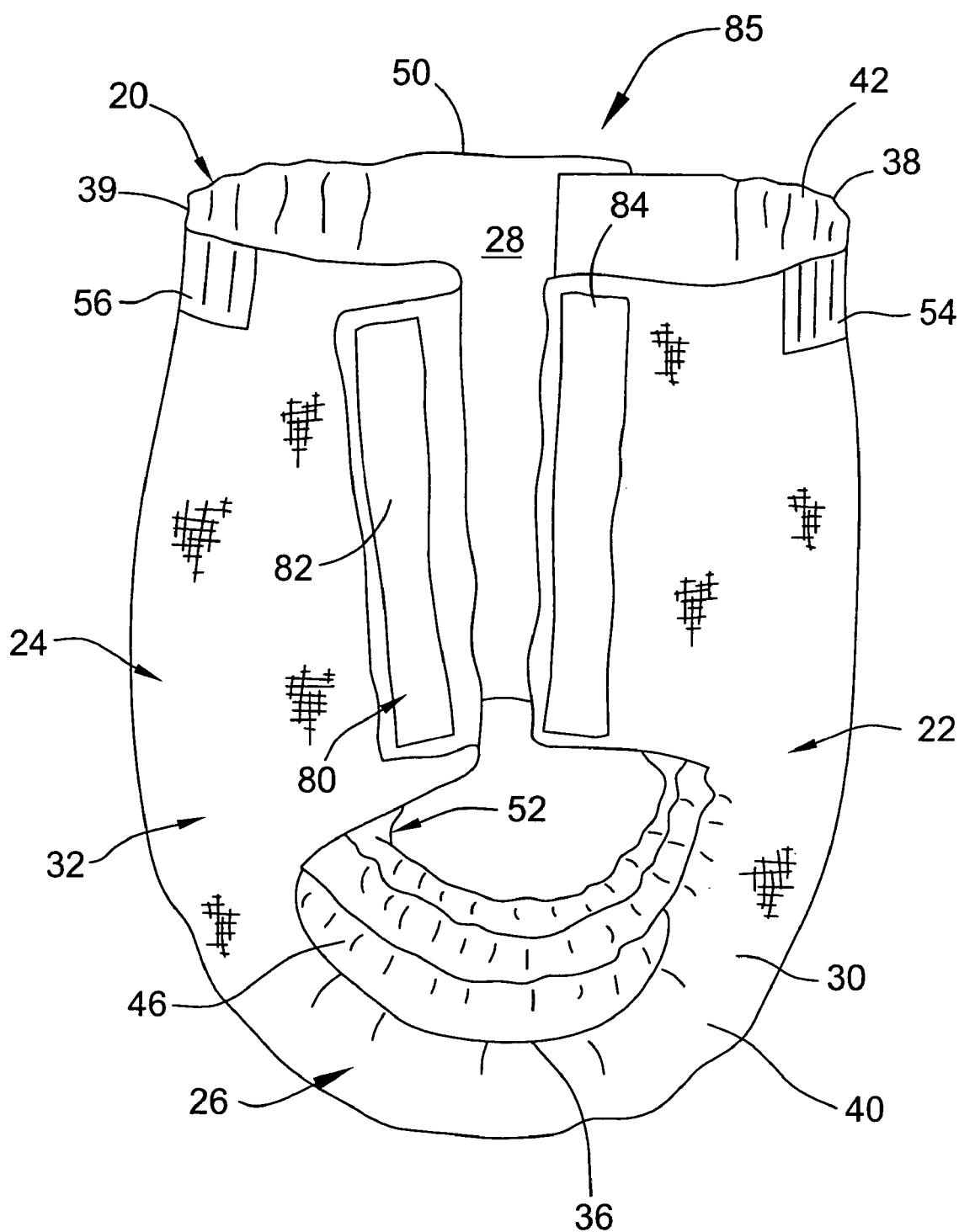
FIG. 1 is a side perspective of an article of the present invention shown in the form of a pair of training pants having a mechanical fastening system fastened on one side of the training pants and unfastened on the opposite side thereof.

Referring now to the drawings and in particular to FIG. 1, an absorbent article of the present invention is representatively illustrated therein in the form of children's toilet training pants and is indicated in its entirety by the reference numeral 20. The absorbent article 20 may or may not be disposable, which refers to articles that are intended to be discarded after a limited period of use instead of being laundered or otherwise conditioned for reuse. It is understood that the present invention is suitable for use with various other absorbent articles intended for personal wear, including but not limited to diapers, feminine hygiene products, incontinence products, medical garments, surgical pads and bandages, other personal care or health care garments, and the like without departing from the scope of the present invention.

By way of illustration only, various materials and methods for constructing training pants such as the pants 20 of the various aspects of the present invention are disclosed in PCT Patent Application WO 00/37009 published Jun. 29, 2000 by A. Fletcher et al; U.S. Pat. No. 4,940,464 issued Jul. 10, 1990 to Van Gompel et al.; U.S. Pat. No. 5,766,389 issued Jun. 16, 1998 to Brandon et al., and U.S. Pat. No. 6,645,190 issued Nov. 11, 2003 to Olson et al. which are incorporated herein by reference.

Figure 2:
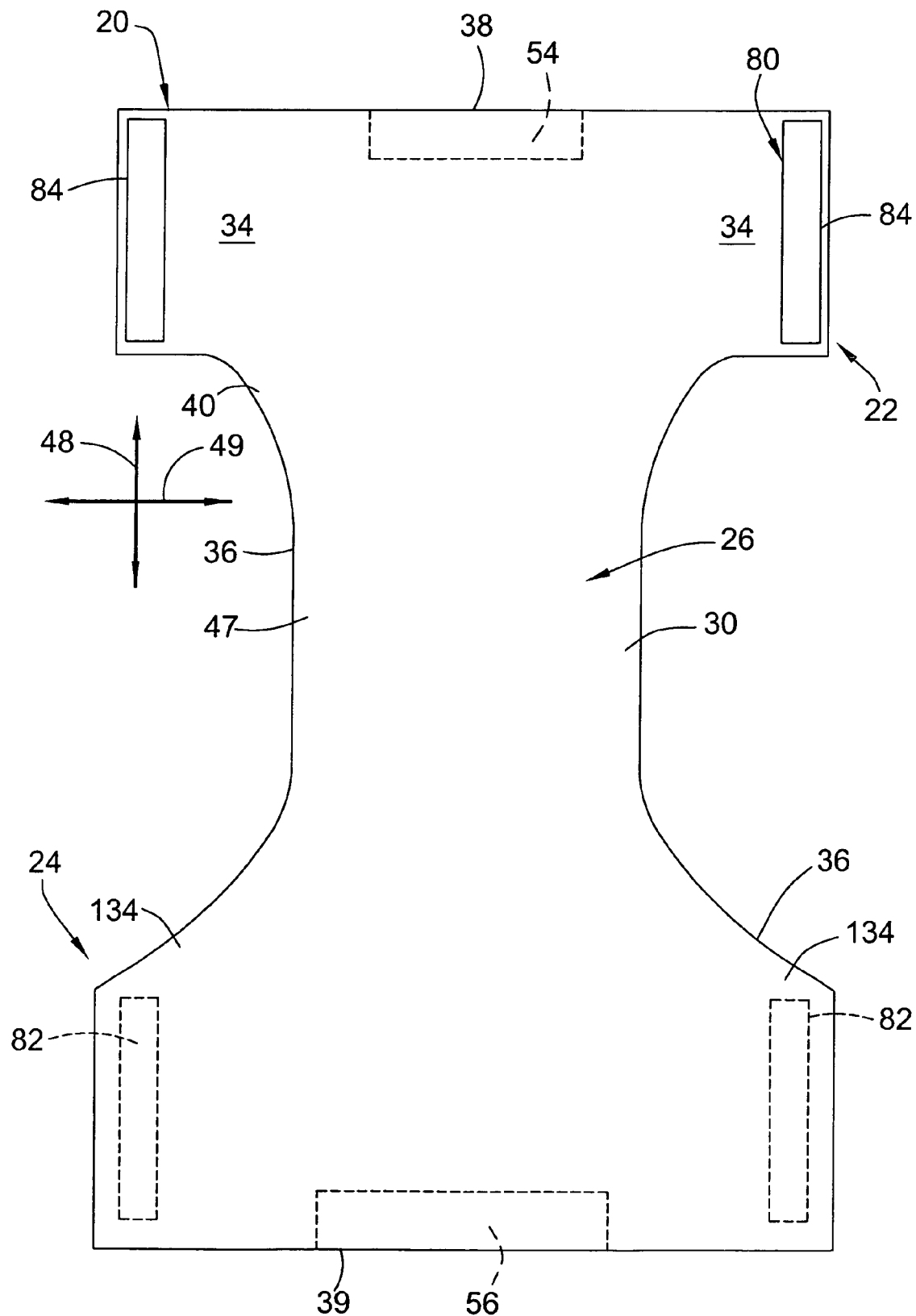
FIG. 2 illustrates a bottom plan view of the training pants of FIG. 1 with the pants in an unfastened, unfolded and laid flat condition, and showing the surface of the training pants that faces away from the wearer.
Figure 3:
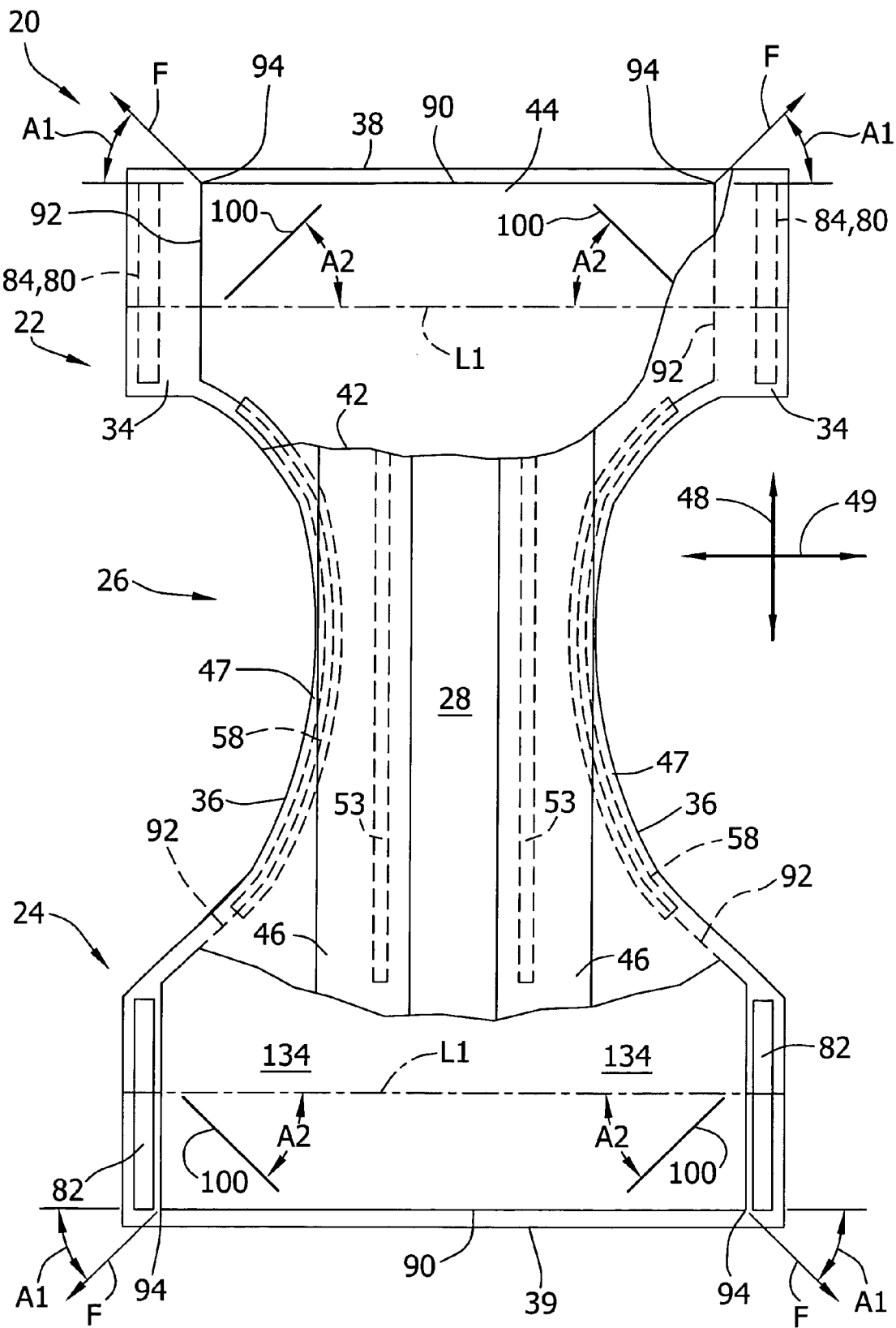
FIG. 3 illustrates a top plan view similar to FIG. 2 showing the surface of the training pants that faces the wearer when worn and with portions cut away to show underlying features.

The pair of training pants 20 is illustrated in FIG. 1 in a partially fastened condition. The pants 20 define a longitudinal direction 48 of the pants (e.g. of the article) and a lateral direction 49 thereof perpendicular to the longitudinal direction as shown in FIGS. 2 and 3. The pants 20 further define a pair of longitudinal end regions, otherwise referred to herein as a front waist region 22 and a back waist region 24, and a center region, otherwise referred to herein as a crotch region 26, extending longitudinally between and interconnecting the front and back waist regions 22, 24. The pants 20 also define an inner surface 28 adapted in use (e.g., positioned relative to the other components of the pants 20) to be disposed toward the wearer, and an outer surface 30 opposite the inner surface. The front and back waist regions 22, 24 comprise those portions of the pants 20, which when worn, wholly or partially cover or encircle the waist or mid-lower torso of the wearer. The crotch region 26 generally is that portion of the pants 20 which, when worn, is positioned between the legs of the wearer and covers the lower torso and crotch of the wearer. With additional reference to FIGS. 2 and 3, the pair of training pants 20 has a pair of laterally opposite side edges 36 and a pair of longitudinally opposite waist edges (broadly, longitudinal ends), respectively designated front waist edge 38 and back waist edge 39.

The illustrated pants 20 comprises an absorbent assembly, generally indicated at 32, and a fastening system for securing the pants in a three-dimensional pants configuration. The absorbent assembly 32 is illustrated in FIGS. 1-8 as having an hourglass shape. However, it is contemplated that the absorbent assembly 32 may have other shapes (e.g., rectangular, T-shaped, I-shaped, and the like) without departing from the scope of this invention.

The absorbent assembly 32 comprises an outer cover 40 and a bodyside liner 42 (FIGS. 1 and 3) attached to the outer cover 40 in a superposed (opposed) relation therewith by adhesives, ultrasonic bonds, thermal bonds, pressure bonds, or other conventional techniques. The liner 42 is suitably joined to the outer cover 40 along at least a portion of the longitudinal ends of the pants 20. In addition, the liner 42 is suitably joined to the outer cover 40. The liner 42 is suitably adapted, i.e., positioned relative to the other components of the pants 20, for contiguous relationship with the wearer's skin during wear of the pants. The absorbent assembly 32 also comprises an absorbent structure 44 (FIG. 3) disposed between the outer cover 40 and the bodyside liner 42 for absorbing liquid body exudates exuded by the wearer and a pair of containment flaps 46 secured to the bodyside liner 42 for inhibiting the lateral flow of body exudates.

With the training pants 20 in the fastened position as partially illustrated in FIG. 1, the front and back waist regions are connected together by the fastening system 80 to define the three-dimensional pants configuration having a waist opening 50 and a pair of leg openings 52. The front and back waist edges 38 and 39 (e.g. longitudinal ends) of the training pants 20 are configured to encircle the waist of the wearer to define the waist opening 50 (FIG. 1) of the pants.

As illustrated in FIG. 3, a flap elastic member 53 can be operatively joined with each containment flap 46 in any suitable manner as is well known in the art. The elasticized containment flaps 46 define a partially unattached edge which assumes an upright configuration in at least the crotch region 26 of the training pants 20 to form a seal against the wearer's body. The containment flaps 46 can be located along the side edges, and can extend longitudinally along the entire length of the absorbent assembly 32 or may extend only partially along the length thereof. Suitable constructions and arrangements for the containment flaps 46 are generally well known to those skilled in the art and are described in U.S. Pat. No. 4,704,116 issued Nov. 3, 1987 to Enloe, which is incorporated herein by reference.

To further enhance containment and/or absorption of body exudates, the training pants 20 may comprise a front waist elastic member 54 (FIG. 2), a rear waist elastic member 56, and leg elastic members 58 (FIG. 3), as are known to those skilled in the art. The waist elastic members 54 and 56 may be operatively joined to the outer cover 40 and/or the bodyside liner 42 adjacent the longitudinal ends 38, 39. The leg elastic members 58 may be operatively joined to the outer cover 40 and/or the bodyside liner 42 along the opposite side edges generally at the crotch region 26 of the training pants 20.

The flap elastic members 53, the waist elastic members 54 and 56, and the leg elastic members 58 can be formed of any suitable elastic material. As is well known to those skilled in the art, suitable elastic materials comprise sheets, threads, strands, or ribbons of natural rubber, synthetic rubber, or thermoplastic elastomeric polymers. The elastic materials can be stretched and adhered to a substrate, adhered to a gathered substrate, or adhered to a substrate and then elasticized or shrunk, for example with the application of heat, such that elastic retractive forces are imparted to the substrate. In one particular aspect, for example, the leg elastic members 58 may comprise a plurality of dry-spun coalesced multifilament spandex elastomeric threads sold under the trade name LYCRA and available from Invista, Inc. of Wilmington, Del., U.S.A.

The fastening system 80 of the illustrated embodiment comprises laterally opposite first fastening components 82 adapted for refastenable engagement to corresponding laterally opposite second fastening components 84. In one embodiment, a front or outer surface of each of the fastening components 82, 84 comprises a plurality of engaging elements. The engaging elements of the first fastening components 82 are adapted to repeatedly engage and disengage corresponding engaging elements of the second fastening components 84 to releasably secure the pants 20 in its three-dimensional configuration.

The fastening components 82, 84 can comprise any refastenable fasteners suitable for absorbent articles, such as adhesive fasteners, cohesive fasteners, mechanical fasteners, or the like. In particular embodiments the fastening components comprise mechanical fastening elements for improved performance. Suitable mechanical fastening elements can be provided by interlocking geometric shaped materials, such as hooks, loops, bulbs, mushrooms, arrowheads, balls on stems, male and female mating components, buckles, snaps, or the like.

In the illustrated aspect, the first fastening components 82 comprise loop fasteners and the second fastening components 84 comprise complementary hook fasteners. Alternatively, the first fastening components 82 can comprise hook fasteners and the second fastening components 84 can comprise complementary loop fasteners. In another embodiment, the fastening components 82, 84 can comprise interlocking similar surface fasteners, or adhesive and cohesive fastening elements such as an adhesive fastener and an adhesive-receptive landing zone or material; or the like. One skilled in the art will recognize that the shape, density and polymer composition of the hooks and loops may be selected to obtain the desired level of engagement between the fastening components 82, 84. When engaged, the fastening components 82, 84 of the illustrated aspect define refastenable engagement seams 85 (FIG. 1). Suitable fastening systems are also disclosed in the previously incorporated PCT Patent Application WO 00/37009 published Jun. 29, 2000 by A. Fletcher et al. and the previously incorporated U.S. Pat. No. 6,645,190 issued Nov. 11, 2003 to Olson et al.

The outer cover 40 suitably comprises a material that is substantially liquid impermeable. The outer cover 40 can be a single layer of liquid impermeable material, but more suitably comprises a multi-layered laminate structure in which at least one of the layers is liquid impermeable. For instance, the outer cover 40 can comprise a liquid permeable outer layer and a liquid impermeable inner layer that are suitably joined together by a laminate adhesive, ultrasonic bonds, thermal bonds, pressure bonds or the like. Suitable laminate adhesives, which can be applied continuously or intermittently as beads, a spray, parallel swirls, or the like, can be obtained from Bostik Findley Adhesives, Inc., of Wauwautosa, Wis., U.S.A., or from National Starch and Chemical Company, Bridgewater, N.J. U.S.A. The liquid permeable outer layer can be any suitable material and is desirably one that provides a generally cloth-like texture. One example of such a material is a 20 gsm (grams per square meter) spunbond polyolefin nonwoven web. The outer layer may also be made of those materials of which the liquid permeable bodyside liner 42 is made. While it is not a necessity for the outer layer to be liquid permeable, it is suitable that it provides a relatively cloth-like texture to the wearer.

The inner layer of the outer cover 40 can be both liquid and vapor impermeable, or it may be liquid impermeable and vapor permeable. The inner layer can be manufactured from a thin plastic film, although other flexible liquid impermeable materials may also be used. The inner layer, or the liquid impermeable outer cover 40 when a single layer, prevents waste material from wetting articles, such as bed sheets and clothing, as well as the wearer and caregiver. A suitable liquid impermeable film for use as a liquid impermeable inner layer, or a single layer liquid impermeable outer cover 40, is a 0.75 mil (0.02 millimeter) polyethylene film commercially available from Pliant Corporation of Schaumburg, Ill., U.S.A.

More suitably, the outer cover 40 is stretchable, and even more suitably the outer cover is elastomeric. As used herein, the term "stretchable" refers to a material that may be extensible or elastomeric. That is, the material may be extended, deformed or the like, without breaking, and may or may not significantly retract after removal of an extending force. The terms "elastomeric" or "elastic" are used interchangeably herein and refer to that property of a material where upon removal of an elongating force, the material is capable of recovering to substantially its unstretched size and shape or the material exhibits a significant retractive force. The term "extensible" refers to that property of a material where upon removal of an elongating force, the material experiences a substantially permanent deformation or the material does not exhibit a significant retractive force. In particular, elastomeric materials utilized in connection with the present invention may be elongated/extended or stretched in at least one direction without breaking by at least 25% (to at least 125% of its initial unstretched length) in at least one direction, suitably by at least 50% (to at least 150% of its initial unstretched length) and which will recover, upon release of the applied stretching or biasing force, at least 10% of their elongation. It is generally preferable that the elastomeric material or composite be capable of being elongated by at least 100%, more preferably by at least 200%, of its relaxed length and recover at least 30%, and more preferably at least 50%, of its elongation upon release of a stretching, biasing force within about 1 minute.

Similarly, extensible or elongatable materials of the present invention may be capable of stretching in at least one direction without breaking by at least 25% (to at least 125% of its initial unstretched length) in at least one direction, suitably by at least 50% (to at least 150% of its initial unstretched length), more suitably by at least 100% (to at least 200% of its initial unstretched length). As an example, an extensible material having an initial unstretched length of 3 inches (7.6 centimeters) may be stretched without breaking to a stretched length of at least 3.75 inches (9.5 centimeters) in at least one direction (for the "by at least 25%" value).

The outer cover 40 may be constructed of spunbond fabrics, films, meltblown fabrics, elastic netting, microporous web, bonded carded webs or foams provided by elastomeric or polymeric materials. Elastomeric non-woven laminate webs can comprise a non-woven material joined to one or more gatherable non-woven webs, films, or foams. Stretch Bonded Laminates (SBL) and Neck Bonded Laminates (NBL) are examples of elastomeric composites. Non-woven fabrics are any web of material that has been formed without the use of textile weaving processes which produce a structure of individual fibers that are interwoven in an identifiable repeating manner.

Examples of suitable materials are spunbond-meltblown fabrics, spunbond-meltblown-spunbond fabrics, spunbond fabrics, or laminates of such fabrics with films, foams, or other nonwoven webs. Elastomeric materials may include cast or blown films, foams, or meltblown fabrics composed of polyethylene, polypropylene, or polyolefin copolymers, as well as combinations thereof. The elastomeric materials may include PEBAX elastomer (available from AtoChem located in Philadelphia, Pa.), HYTREL elastomeric polyester (available from Invista, Inc. of Wilmington, Del.), KRATON elastomer (available from Kraton Polymers of Houston, Tex.), or strands of LYCRA elastomer (available from Invista, Inc. of Wilmington, Del.), or the like, as well as combinations thereof. The outer cover 40 may comprise materials that have elastomeric properties through a mechanical process, printing process, heating process, or chemical treatment. For example such materials may be apertured, creped, neck-stretched, heat activated, embossed, micro-strained, or combinations thereof and may be in the form of films, webs, and laminates.

In particular suitable embodiments of the invention, the outer cover 40 may include a 0.4 ounces per square yard (osy) (13.6 grams per square meter (gsm)) basis weight layer of G2760 KRATON elastomer strands adhesively laminated with a 0.3 gsm layer of adhesive between two facings. Each facing can be composed of a thermal point bonded bicomponent spunbond non-woven fibrous web having a 0.7 osy (23.7 gsm) basis weight. The adhesive is similar to an adhesive which is supplied by Bostik-Findley Adhesive of Wauwautosa, Wis. and designated as H2525A, and the elastomer strands are placed and distributed to provide approximately 12 strands of KRATON elastomer per inch (2.54 cm) of lateral width of the outer cover 40.

Alternatively, the outer cover 40 may comprise a woven or non-woven fibrous web layer that has been totally or partially constructed or treated to impart the desired levels of liquid impermeability to selected regions that are adjacent or proximate the absorbent structure. For example, the outer cover 40 may include a gas-permeable, non-woven fabric layer laminated to a polymer film layer which may or may not be gas-permeable. Other examples of fibrous, cloth-like outer cover 40 materials can include a stretch thinned or stretch thermal laminate (STL) material composed of a 0.6 mil (0.015 mm) thick polypropylene blown film and a 0.7 osy (23.8 gsm) polypropylene spunbond material (2 denier fibers).

Suitable materials for a biaxially stretchable (i.e., stretchable both laterally and longitudinally) outer cover 40 include biaxially extensible material and biaxially elastic material. One example of a suitable biaxially stretchable outer cover material can include a 0.3 osy polypropylene spunbond that is necked 60% in the lateral direction 49 and creped 60% in the longitudinal direction 48, laminated with 3 grams per square meter (gsm) Bostik-Findley H2525A styrene-isoprene-styrene based adhesive to 8 gsm PEBAX 2533 film with 20% $TiO_2$ concentrate. The outer cover 40 can preferably be stretched, laterally and/or longitudinally, by at least 30% (to at least 130% of an initial (unstretched) width and/or length of the outer cover 40). More suitably, the outer cover 40 can be stretched laterally and/or longitudinally, by at least 50% (to at least 150% of the unstretched width or length of the outer cover 40). Even more suitably, the outer cover 40 can be stretched, laterally and/or longitudinally, by at least 100% (to at least 200% of the unstretched width or length of the outer cover 40). Tension force in the outer cover 40 at 50% extension is preferably between 50 and 1000 grams, more preferably between 100 and 600 grams, as measured on a 3 inch (7.62 cm) wide piece of the outer cover material.

Another example of a suitable material for a biaxially stretchable outer cover 40 is a breathable elastic film/nonwoven laminate, described in U.S. Pat. No. 5,883,028, issued to Morman et al., incorporated herein by reference. Examples of materials having two-way stretchability and retractability are disclosed in U.S. Pat. No. 5,116,662 issued to Morman and U.S. Pat. No. 5,114,781 issued to Morman, both of which are hereby incorporated herein by reference. These two patents describe composite elastic materials capable of stretching in at least two directions. The materials have at least one elastic sheet and at least one necked material, or reversibly necked material, joined to the elastic sheet at least at three locations arranged in a nonlinear configuration, so that the necked, or reversibly necked, web is gathered between at least two of those locations.

The outer cover 40 is suitably sized (e.g., in length and width) larger than the absorbent structure 44 to extend outward beyond the periphery thereof. For example, the outer cover 40 may extend outward beyond the absorbent structure periphery a distance in the range of about 1.3 centimeters to about 2.5 centimeters (about 0.5 to 1 inch). Alternatively, the outer cover 40 may extend a greater amount or a lesser amount beyond the periphery of the absorbent structure 44 as is known in the art.

The bodyside liner 42 is suitably compliant, soft-feeling, and non-irritating to the wearer's skin. The bodyside liner 42 is also sufficiently liquid permeable to permit liquid body exudates to readily penetrate through its thickness to the absorbent structure 44. A suitable bodyside liner 42 may be manufactured from a wide selection of web materials, such as porous foams, reticulated foams, apertured plastic films, woven and non-woven webs, or a combination of any such materials. For example, the bodyside liner 42 may comprise a meltblown web, a spunbonded web, or a bonded-carded-web composed of natural fibers, synthetic fibers or combinations thereof. The bodyside liner 42 may be composed of a substantially hydrophobic material, and the hydrophobic material may optionally be treated with a surfactant or otherwise processed to impart a desired level of wettability and hydrophilicity.

The bodyside liner 42 may also be stretchable, and more suitably it may be elastomeric. Suitable elastomeric materials for construction of the bodyside liner 42 can include elastic strands, LYCRA elastics, cast or blown elastic films, non-woven elastic webs, meltblown or spunbond elastomeric fibrous webs, as well as combinations thereof. Examples of suitable elastomeric materials include KRATON elastomers, HYTREL elastomers, ESTANE elastomeric polyurethanes (available from Noveon of Cleveland, Ohio), or PEBAX elastomers.

As an additional example, in one aspect the bodyside liner 42 suitably comprises a non-woven, spunbond polypropylene fabric composed of about 2 to 3 denier fibers formed into a web having a basis weight of about 12 gsm which is necked approximately 60 percent. Strands of about 9 gsm KRATON G2760 elastomer material placed eight strands per inch (2.54 cm) are adhered to the necked spunbond material. The fabric is surface treated with an operative amount of surfactant, such as about 0.6 percent AHCOVEL Base N62 surfactant, available from ICI Americas, a business having offices in Wilmington, Del., U.S.A. The surfactant can be applied by any conventional means, such as spraying, printing, brush coating or the like. Other suitable materials can be extensible biaxially stretchable materials, such as a neck stretched/creped spunbond. The bodyside liner 42 can also be made from extensible materials as are described in U.S. patent application Ser. No. 09/563,417 filed on May 3, 2000 by Roessler et al. or from biaxially stretchable materials as are described in U.S. patent application Ser. No. 09/698,512 filed on Oct. 27, 2000 by Vukos et al., both references which are herby incorporated by herein by reference.

The liner 42 can suitably be stretched, laterally and/or longitudinally, by at least 30% (to at least 130% of an initial (unstretched) width and/or length of the liner 42). More suitably, the liner 42 can be stretched laterally and/or longitudinally, by at least 50% (to at least 150% of the unstretched width or length of the liner 42). Even more suitably, the liner 42 can be stretched, laterally and/or longitudinally, by at least 100% (to at least 200% of the unstretched width or length of the liner 42). Tension force in the liner 42 at 50% extension is preferably between 50 and 1000 grams, more preferably between 100 and 600 grams, as measured on a 3 inch (7.62 cm) wide piece of the liner material. The nonwoven web can be mechanically stretched, preferably stretched in the machine direction (i.e., longitudinal direction), causing the web to contract or neck in the cross direction (i.e., lateral direciton), before applying the adhesive and creping the web. The resulting necked web product is stretchable in the cross direction. Mechanical stretching of the web is accomplished using processes well known in the art. For instance, the web may be pre-stretched by about 0-100% of its initial length in the machine direction to obtain a necked web that can be stretched (e.g. by about 0-100%) in the cross direction. Preferably, the web is stretched by about 10-100% of its initial length, more commonly by about 25-75% of its initial length. The stretched web is then dimensionally stabilized to some extent, first by the adhesive which is applied to the web, and second by the heat which is imparted from the creping drum. This stabilization sets the cross-directional stretch properties of the web. The machine direction stretch is further stabilized by the out-of-plane deformation of the nonwoven web bonded areas that occurs during creping.

The absorbent structure 44 is disposed between the outer cover 40 and the bodyside liner 42 and has longitudinally opposite ends 90 and laterally opposite side edges 92 (FIGS. 3-6, and 9) that meet at respective corner regions 94 of the absorbent structure. As used herein, the corner regions 94 of the absorbent structure refer generally to those regions at which the edge margin of the absorbent structure transitions from a longitudinal end to an adjacent lateral side edge. For example, in the illustrated embodiment, longitudinal ends 90 of the absorbent structure intersect (e.g., at a right angle) the lateral side edges 92 such that the corner regions 94 of the absorbent structure 44 are generally a defined point. However, it is contemplated that the corner regions 94 may be rounded, e.g., where the absorbent structure 44 is curved to define a rounded transition from the longitudinal ends 90 to adjacent lateral side edges 92, and remain within the meaning of the term corner region as used herein as well as within the scope of this invention. As such, the absorbent structure 44 of the illustrated embodiment has four defined corner regions 94, two of which are laterally spaced from each other at the front waist region 22 of the pants 20 and the other two of which are laterally spaced from each other at the rear waist region 24 of the pants.

While the illustrated absorbent structure 44 is shown and described herein as extending from the crotch region 26 into both the front and back waist regions 22 and 24, it is contemplated that the absorbent structure may extend from the crotch region into only the front waist region, or only the back waist region, without departing from the scope of this invention.

The absorbent structure 44 is suitably compressible, conformable, non-irritating to a wearer's skin, and capable of absorbing and retaining liquids and certain body wastes. For example, the absorbent structure 44 may comprise cellulosic fibers (e.g., wood pulp fibers), other natural fibers, synthetic fibers, woven or nonwoven sheets, scrim netting or other stabilizing structures, superabsorbent material, binder materials, surfactants, selected hydrophobic materials, pigments, lotions, odor control agents or the like, as well as combinations thereof. In a particular embodiment, the absorbent structure comprises a matrix of cellulosic fluff and superabsorbent hydrogel-forming particles. The cellulosic fluff may include a blend of wood pulp fluff. One suitable type of fluff is identified with the trade designation CR 1654, available from U.S. Alliance of Childersburg, Ala., USA, and is a bleached, highly absorbent sulfate wood pulp containing primarily soft wood fibers.

The materials may be formed into a web structure by employing various conventional methods and techniques. For example, the absorbent structure 44 may be formed by a dry-forming technique, an air forming technique, a wet-forming technique, a foam-forming technique, or the like, as well as combinations thereof. Methods and apparatus for carrying out such techniques are well known in the art. Furthermore, the absorbent structure 44 may itself encompass multiple layers in a Z-direction (e.g., thickness) of the absorbent structure. Such multiple layers may take advantage of differences in absorbent capacity, such as by placing a lower absorbent capacity material layer closer to the liner 42 and a higher absorbent capacity material closer to the outer cover 40. Likewise, discrete portions of a single-layered absorbent structure may encompass higher capacity absorbents, and other discrete portions of the structure may encompass lower capacity absorbents.

Superabsorbent material is suitably present in the absorbent structure in an amount of from about 0 to about 90 weight percent based on total weight of the absorbent structure. The absorbent structure may suitably have a density within the range of about 0.10 to about 0.60 grams per cubic centimeter.

Superabsorbent materials are well known in the art and can be selected from natural, synthetic, and modified natural polymers and materials. The superabsorbent materials can be inorganic materials, such as silica gels, or organic compounds, such as crosslinked polymers. Typically, a superabsorbent material is capable of absorbing at least about 10 times its weight in liquid, and preferably is capable of absorbing more than about 25 times its weight in liquid. Suitable superabsorbent materials are readily available from various suppliers. For example, SXM 9394, and Favor 9543 are suitable superabsorbent materials available from Degussa Superabsorbers of Germany.

After being formed or cut to a desired shape, the absorbent structure 44 may be wrapped or encompassed by a suitable wrap (not shown) that aids in maintaining the integrity and shape of the absorbent structure.

The absorbent structure 44 may alternatively comprise a coform material. The term "coform material" generally refers to composite materials comprising a mixture or stabilized matrix of thermoplastic fibers and a second non-thermoplastic material. As an example, coform materials are made by a process in which at least one meltblown die head is arranged near a chute through which other materials are added to the web while it is forming. Such other materials may include, but are not limited to, fibrous organic materials such as woody or non-woody pulp such as cotton, rayon, recycled paper, pulp fluff and also superabsorbent particles, inorganic absorbent materials, treated polymeric staple fibers and the like. Any of a variety of synthetic polymers may be utilized as the melt-spun component of the coform material. For instance, in certain aspects, thermoplastic polymers can be utilized. Some examples of suitable thermoplastics that can be utilized include polyolefins, such as polyethylene, polypropylene, polybutylene and the like; polyamides; and polyesters. In one aspect, the thermoplastic polymer is polypropylene. Some examples of such coform materials are disclosed in U.S. Pat. No. 4,100,324 to Anderson, et al.; U.S. Pat. No. 5,284,703 to Everhart, et al.; and U.S. Pat. No. 5,350,624 to Georger, et al.; which are incorporated herein by reference.

In the preferred embodiment, the absorbent structure 44 is stretchable so as not to inhibit the stretchability of other components to which the absorbent structure may be adhered, such as the outer cover 40 and bodyside liner 42. In a particularly suitable embodiment, the bodyside liner 42, the outer cover 40, and the absorbent structure 44 are each stretchable so that the absorbent structure allows for increased stretchability of the absorbent article as a whole. That is, non-stretchable absorbent structures tend to inhibit stretching of the outer cover and liner, even where the outer cover and liner are stretchable. A stretchable absorbent structure allows the outer cover and liner to more readily stretch, thereby increasing the overall stretchability (and ease of stretching) the entire article.

For this purpose, the absorbent structure material can include elastomeric fibers in an amount which is at least a minimum of about 2 wt %. The amount of elastomeric fibers can alternatively be at least about 3 wt %, and can optionally be at least about 5 wt % to provide improved performance. In addition, the amount of elastomeric fibers can be not more than about 60 wt %. Alternatively, the amount of elastomeric fibers can be not more than about 45 wt %, and optionally, can be not more than about 30 wt % to provide improved benefits. The elastomeric fiber content may impact the absorbent structure 44 stretchability and structural stability without excessively degrading the physical properties or the liquid-management properties of the absorbent structure. An absorbent structure 44 comprising an excessively low proportion of elastomeric fibers may be insufficiently stretchable, and one with an excessively high proportion of elastomeric fibers may exhibit an excessive degradation of its absorbent characteristics, such as poor intake, poor distribution and poor retention of liquid.

The absorbent structure 44 in one particularly suitable embodiment comprises an elastomeric coform material. Such materials are described for instance in U.S. Pat. Nos. 6,231,557 B1 and 6,362,389 B1, which are each incorporated by reference herein. In particular aspects, the elastomeric coform material can have an overall coform basis weight which is at least a minimum of about 50 $g/m^2$. The coform basis weight can alternatively be at least about 100 $g/m^2$ and can optionally be at least about 200 $g/m^2$ to provide improved performance. These values can provide the absorbent structure 44 with the desired stretchability and structural stability without excessively degrading the physical properties or the liquid-management characteristics of the absorbent structure.

Other examples of suitable elastomeric absorbent structures are described in international patent application WO 03/051254 and U.S. Pat. Nos. 5,964,743, 5,645,542, 6,231,557, and 6,362,389 B1, each of which are incorporated by reference herein.

Figure 6:
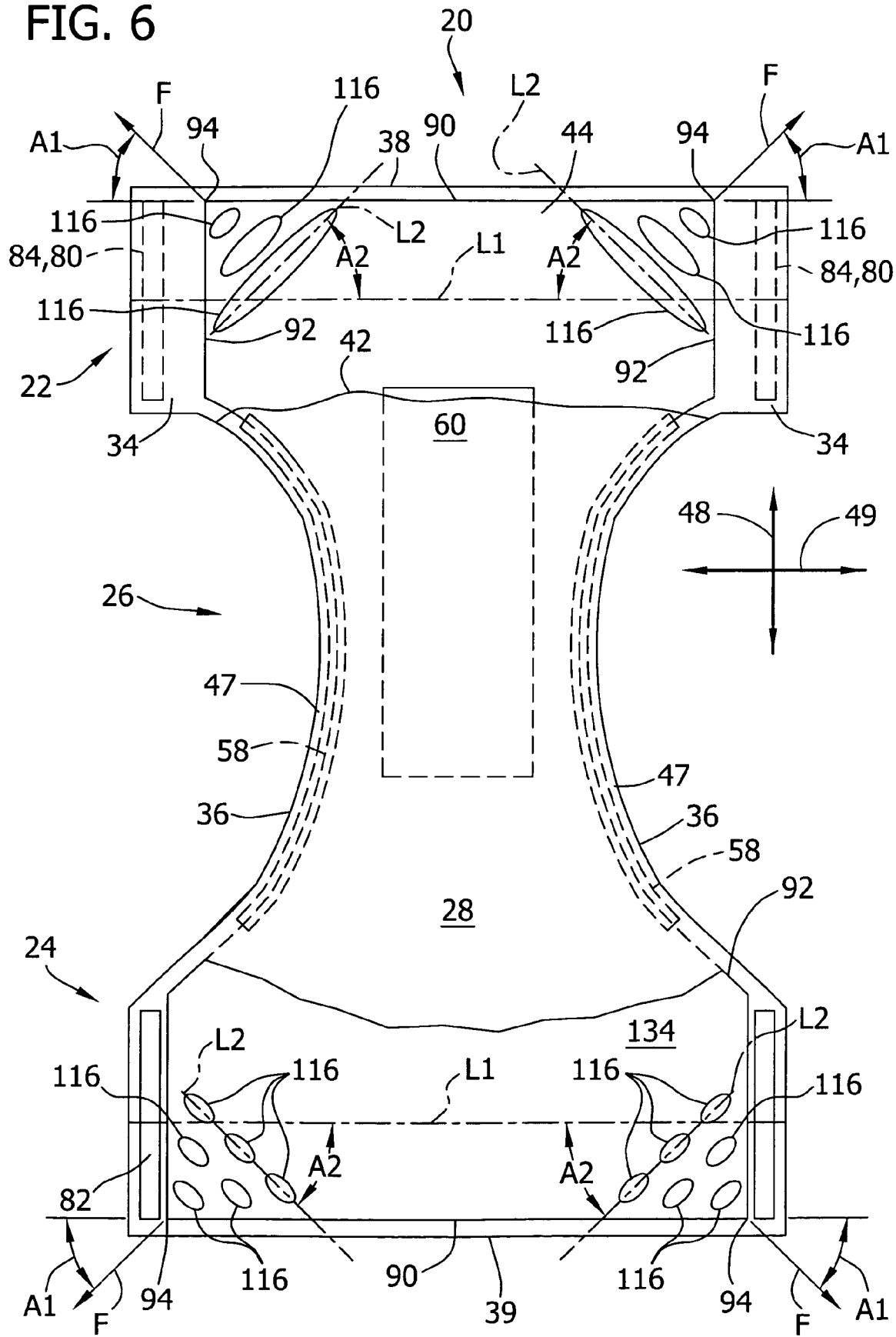
FIG. 6 is a top plan view similar to FIG. 3 but showing an absorbent structure of a fourth embodiment of the invention.

In some embodiments, such as that shown in FIG. 6, a surge management layer 60 is located adjacent the absorbent structure 44 (e.g., between the absorbent structure and the liner 42)

and attached to various components of the article 20 such as the absorbent structure and/or the bodyside liner by methods known in the art, such as by adhesive, ultrasonic or thermal bonding. A surge management layer 60 helps to decelerate and diffuse surges or gushes of liquid that may be rapidly introduced into the absorbent structure of the article. Desirably, the surge management layer 60 can rapidly accept and temporarily hold the liquid prior to releasing the liquid into the storage or retention portions of the absorbent structure 44. Examples of suitable surge management layers are described in U.S. Pat. No. 5,486,166; and U.S. Pat. No. 5,490,846. Other suitable surge management materials are described in U.S. Pat. No. 5,820,973. The entire disclosures of these patents are hereby incorporated by reference herein.

The donning force of an absorbent article refers herein to the force applied to the article to properly don the article on the wearer. The force typically comprises a pulling force applied by the wearer (e.g., via the wearer pulling upward and/or outward on the article), and may further comprise an expansion force applied by the wearer's body to the article to increase the dimensions of the article so as to accommodate the shape and size of the wearer. For example, with reference to the training pants 20, the donning force is the force applied to the pants by a child (or caregiver) to the pants (e.g., at the waist opening) to pull the pants up to the child's waist. This typically comprises sufficient force not only to lift the pants 20 upward but also to expand the waist opening 50 of the pants outward. Additionally, as the pants 20 are pulled up over the child's thighs, buttocks and hips, the child's body may apply additional donning force (e.g., an expansion force) to the pants to expand the waist opening 50 of the pants.

The magnitude and direction of application of the donning force can vary based on the size and construction of the absorbent article being donned, and/or on the donning tendencies of the wearer (i.e., the manner in which a wearer typically dons a garment, such as one foot first, both feet first, pulling at the front and back or at the sides of the article, donning while standing, or sitting, etc.). However, it is believed that the donning force (indicated representatively as F in FIG. 3), particularly for absorbent articles 20 such as training pants and incontinence products that are donned about the hips and waist of a wearer, is applied in a direction that defines an angle A1 (FIG. 3) of greater than zero degrees and less than 90 degrees with respect to the lateral direction 49 of the article. More specifically, it is believed that the donning forces for such absorbent articles 20 are more commonly in a direction that defines an angle A1 of greater than or equal to 30 degrees and less than 90 degrees relative to the lateral direction 49, and even more commonly in a direction than defines an angle A1 greater than or equal to 60 degrees and less than 90 degrees relative to the lateral direction. The absorbent structure 44 of the present invention is suitably configured to reduce the resistance to stretching of the absorbent article, particularly in the direction of application of the donning force F, so that a lower donning force is required to don the article 20 on the wearer.

With particular reference to FIG. 3, the absorbent structure 44 according to one embodiment of the present invention comprises at least one weakening element 100 disposed therein for weakening the absorbent structure to thereby substantially reduce the resistance of the absorbent structure to stretching in the direction of the applied donning force F. For example, in the illustrated embodiment the absorbent structure 44 has four weakening elements 100, one adjacent to each of the corner regions 94 of the absorbent structure (i.e., adjacent to each longitudinal end 90 and corresponding adjacent lateral side edge 92 of the absorbent structure) in the front and back waist regions 22, 24 of the article. It is contemplated, however, that weakening elements 100 may be disposed only in the front waist region 22 of the article 20, or only in the back waist region 24 thereof, without departing from the scope of the invention.

Each of the weakening elements 100 shown in FIG. 3 suitably comprises a slit (broadly, an elongate weakening element) extending fully or partially through the thickness of the absorbent structure 44. The slits 100 each have a length (broadly, a maximum length dimension of the weakening element) extending in a direction that is intended to be generally perpendicular to the donning force applied to the pants 20. For example, the length of each slit shown in FIG. 3 extends in a direction that defines an angle A2 relative to the lateral direction 49 of the absorbent article 44 of greater than zero degrees and less than 90 degrees, more suitably greater than zero degrees and less than or equal to about 60 degrees, and even more suitably greater than zero degrees and less than or equal to about 30 degrees. The two dashed lines L1 extending horizontally across the entire absorbent article of FIG. 3 (e.g. one at the front waist region 22 and one at the back waist region 24) are provided for illustrative purposes only to delineate the angle A2 and do not constitute part of the absorbent article 20. The same is intended for the angled lines L2 extending through the weakening elements 100.

Figure 4:
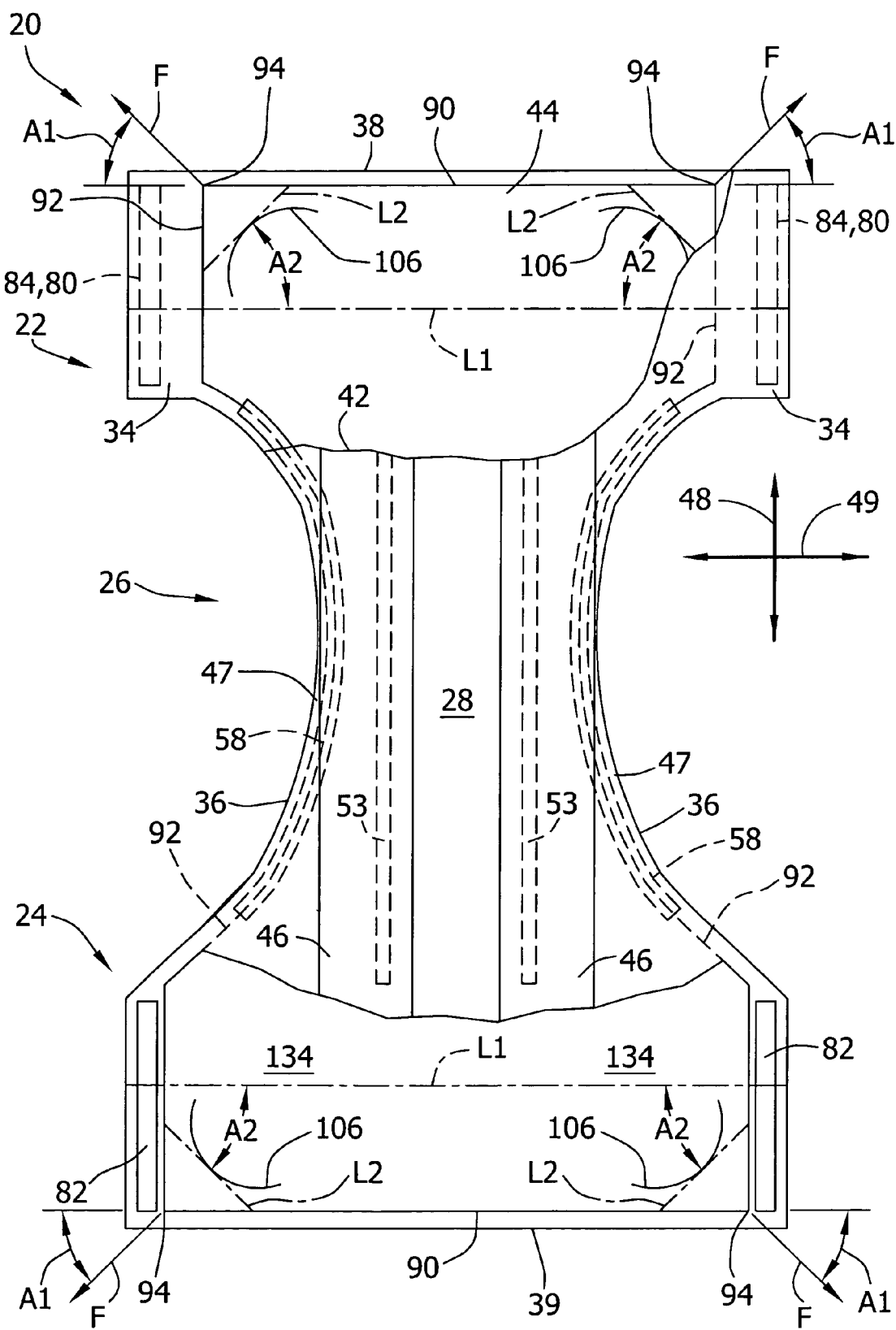
FIG. 4 is a top plan view similar to FIG. 3 but showing an absorbent structure of a second embodiment of the invention.

While the slits 100 shown in FIG. 3 are linear, it is contemplated that the slit may instead be non-linear. For example, in the embodiment of FIG. 4, each slit 106 is generally arcuate or curvilinear. The orientation and curvature of each slit 106 is such that a tangent to the slit extends in a direction that defines an angle A2 relative to the lateral direction 49 of the absorbent article of greater than zero degrees and less than 90 degrees. The arcuate slit 106 shown in FIG. 4 is oriented and curved such that a plurality of tangents define an angle relative to the lateral direction 49 in this range. More suitably, a tangent to the slit defines an angle A2 that is greater than zero degrees and less than or equal to about 60 degrees, and more suitably greater than zero degrees and less than or equal to about 30 degrees.

The arcuate slit 106 facilitates reduced resistance to stretching of the absorbent structure 44 (and hence the absorbent article 20 as a whole) in response to donning forces applied over a range of directions angled relative to the lateral direction 49. It is contemplated that instead of the non-linear slit 106 being a continuous curve, the slit may be segmented, with one or more of the segments extending in a direction that defines an angle A2 relative to the lateral direction 49 within the recited ranges. For example, one segment may extend in a direction that defines an angle of about 30 degrees relative to the lateral direction 49 and a second segment may extend in a direction that defines an angle of about 60 degrees relative to the lateral direction.

Figure 5:
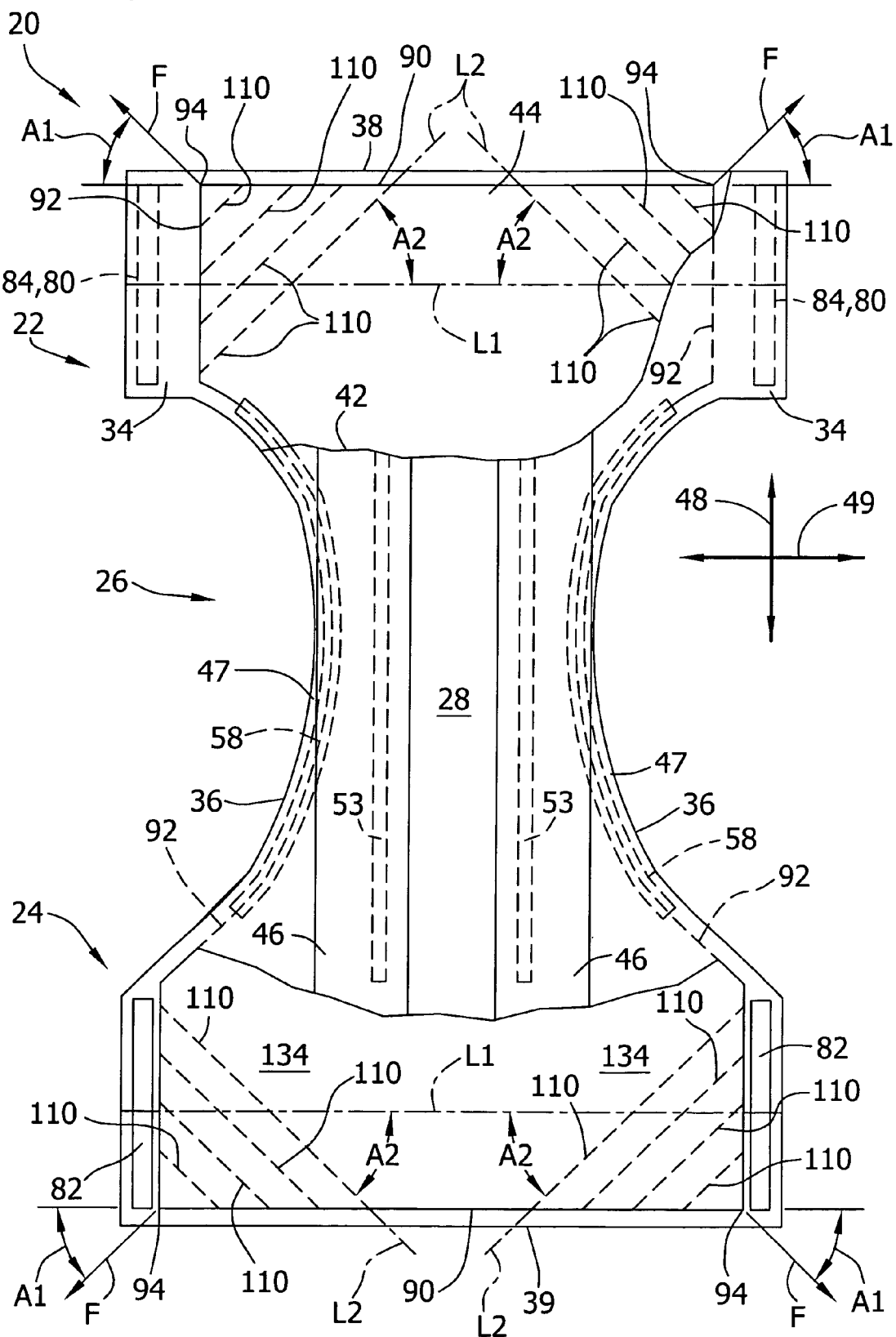
FIG. 5 is a top plan view similar to FIG. 3 but showing an absorbent structure of a third embodiment of the invention.

In another embodiment, shown in FIG. 5, a plurality of weakening elements 110 in the form of slits are disposed adjacent each of the corner regions 94 of the absorbent structure. Some of the slits 106 are arranged in end-to-end (e.g., colinear) spaced relationship with each other intermediate each corresponding longitudinal end 90 and side edge 92 whereby the lengths of the slits lie on a line L2 extending in a direction that defines an angle A2 relative to the lateral direction 49 of greater than zero degrees and less than 90 degrees, more suitably greater than zero degrees and less than or equal to about 60 degrees, and even more suitably greater than zero degrees and less than or equal to about 60 degrees. In the illustrated embodiment, one of the slits 110 in the series of the slits suitably extends to the longitudinal end 90 of the absorbent structure 44, and another slit in the same series of the slits suitably extends to the side edge 92 of the absorbent structure. However, it is contemplated that a slit 110 may extend only to the longitudinal end 90, or only to the side edge 92 of the absorbent structure 44, or that no slits may extend to the longitudinal end or to the side edge, without departing from the scope of this invention.

The slits 110 illustrated in FIG. 5 are also arranged in four parallel rows of slits, with a first or outermost row being disposed nearer the corner region 94 and the remaining rows being spaced sequentially inward from the corner region. Each row of slits 110 lies on a line L2 extending in a direction that suitably defines the angle A2 relative to the lateral direction 49 of the absorbent structure 44. The rows of slits 110 shown in FIG. 5 lie on substantially parallel lines. It is understood, however, that the rows of slits may be other than parallel, as long as each row of slits lies on a line extending in a direction that defines an angle A2 within the recited suitable range of angles relative to the lateral direction 49.

While in the illustrated embodiment the angle A2 defined by the slits 110 disposed at the back waist region 24 of the article 20 is shown to be substantially the same as the angle A2 defined by the slits disposed at the front waist region 22, it is understood that the angle A2 may be different at the front waist region than at the back waist region and remain within the scope of this invention. It is also contemplated that the spacing between slits 110 within a row thereof, or the parallel spacing between two rows of slits, may be greater than or less than the spacing shown in FIG. 5 without departing from the scope of this invention.

Figure 7:
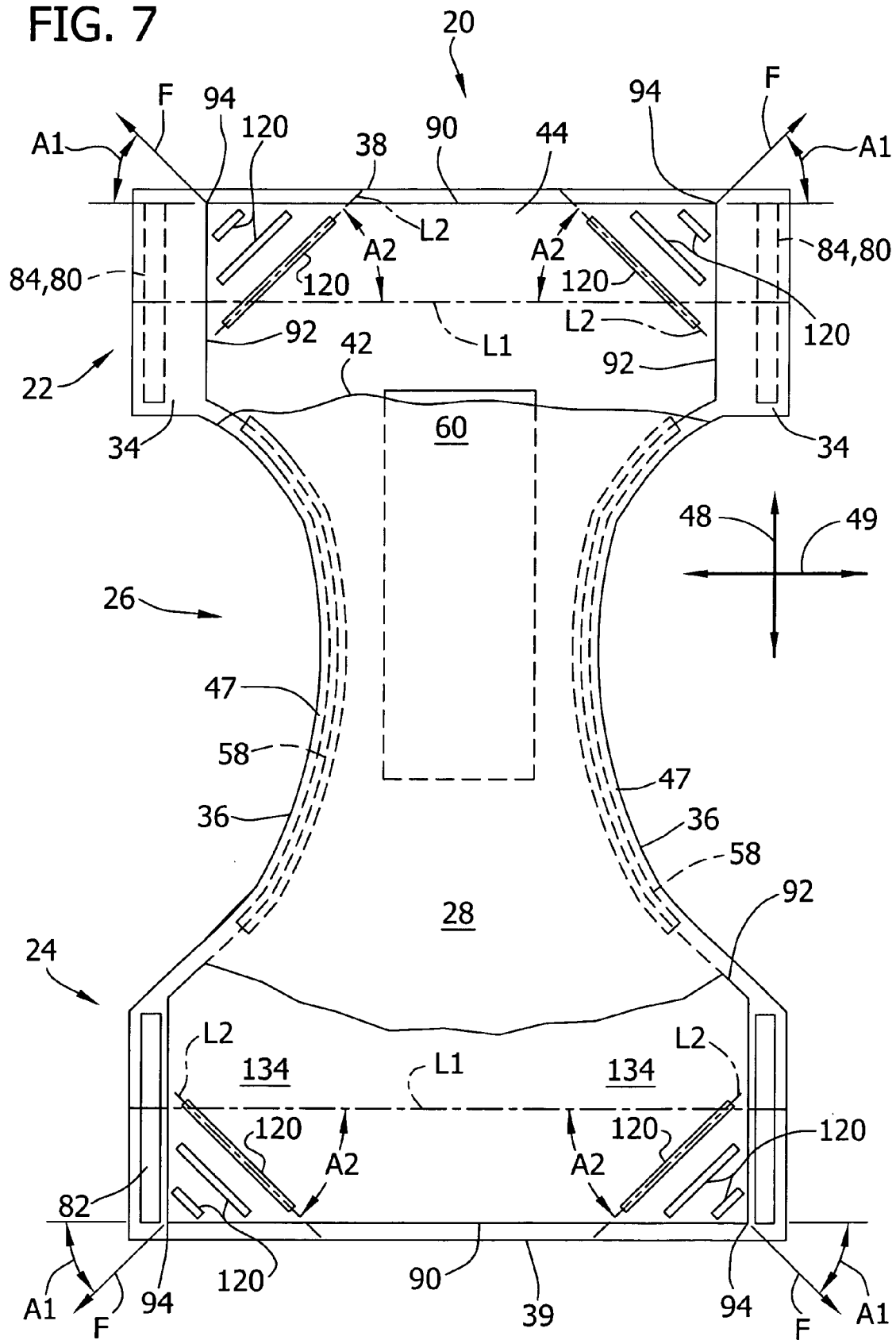
FIG. 7 is a top plan view similar to FIG. 3 but showing an absorbent structure of a fifth embodiment of the invention.
Figure 8:
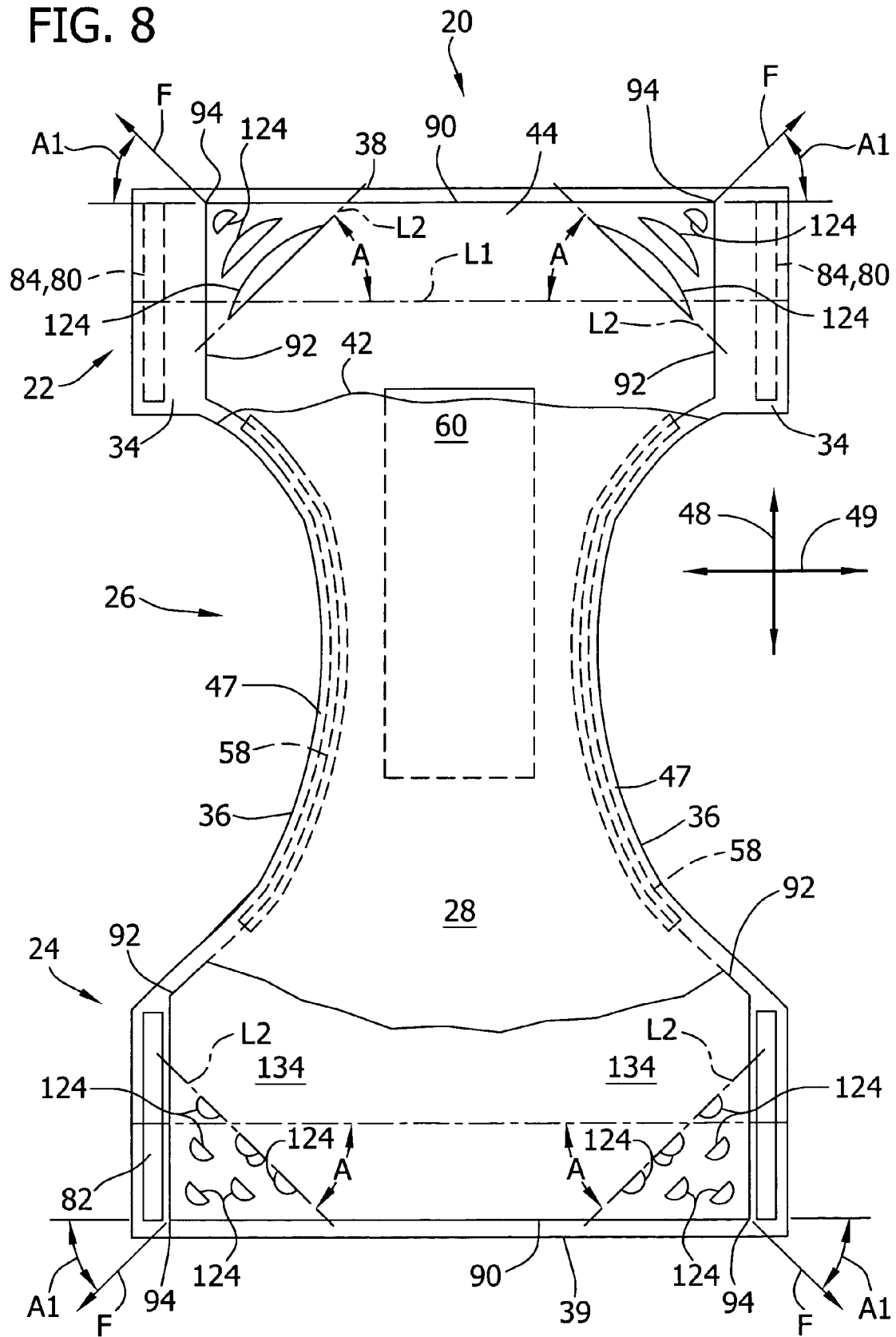
FIG. 8 is a top plan view similar to FIG. 3 but showing an absorbent structure of a sixth embodiment of the invention.

With reference now to FIGS. 6-8, the weakening elements may alternatively comprise voids disposed adjacent the corner regions 94 of the absorbent structure 44. The term "void" as used in reference to the weakening elements refers to apertures that extend through the full thickness of the absorbent structure 44, and to discrete areas of substantially reduced basis weight (e.g., but not extending through the full thickness of the structure) whereby the resistance of the absorbent structure 44 to stretching in the direction of the donning force is decreased generally at the voids.

In the embodiment of FIG. 6, weakening elements 116 are disposed in the absorbent structure 44 at the front waist region 22 and comprise elongate voids having an ovate or elliptical shape. The term elongate as used in reference to the weakening elements refers to a weakening element having a maximum length dimension greater than a maximum width dimension of the weakening element. In the illustrated embodiment, the maximum length dimension of each elongate void 116 suitably extends in a direction that defines an angle A2 relative to the lateral direction 49 of the absorbent article 44 of greater than zero degrees and less than 90 degrees, more suitably greater than zero degrees and less than or equal to about 60 degrees, and even more suitably greater than zero degrees and less than or equal to about 30 degrees (e.g., generally perpendicular to the direction of the donning force F applied to the article 20 by the wearer).

In the illustrated embodiment of FIG. 6, a group of three elongate voids 116 is disposed adjacent each of the corner regions 94 of the absorbent structure 44 at the front waist region 22 of the article 20. The maximum length dimensions of the voids 116 within each group extend in parallel spaced relationship with each other in accordance with the angle A2. The maximum length dimension also increases from the outermost void, nearest the corner region 94, to the innermost void. It is understood, however, that one, two, or more than three elongate voids 116 may be disposed adjacent each corner region 94 of the absorbent structure 44 without departing from the scope of this invention. Also, it is understood that one or more of the voids 116 may extend to the longitudinal end 90 and/or the lateral side edge 92 of the absorbent structure 44. Also, one or more of the voids 116 may be a partial shape (e.g., a partial circle, ellipse, rectangle, etc) located anywhere in the absorbent structure without departing from the scope of this invention.

The weakening elements 116 disposed adjacent the corner regions 94 of the absorbent structure 44 at the back waist region 24 of the article of FIG. 6 also comprise elongate voids. However, these voids 116 are arranged in rows with a first or outermost row being nearest the corner region and comprising a single elongate void, a second or intermediate row comprising a pair of elongate voids disposed in colinear, spaced relationship with each other, and a third or innermost row comprising three elongate voids disposed in colinear, spaced relationship with each other. The maximum length dimensions of the voids 116 extend in a direction that defines the angle A2.

While in the illustrated embodiment the angle A2 defined by the voids 116 disposed at the back waist region 24 of the article 20 is shown to be substantially the same as the angle A2 defined by the voids disposed at the front waist region 22, it is understood that the angle A2 may be different at the front waist region than at the back waist region and remain within the scope of this invention. It is also contemplated that the spacing between elongate voids 116 within a colinear row of voids, or the parallel spacing between two rows of voids, may be greater than or less than the spacing shown in FIG. 6 without departing from the scope of this invention.

Because the elliptical or ovate voids 116 have a curved surface extending along their lengths, the range of potential lines that are tangent to the curved surfaces of the voids is from greater than zero degrees to less than 90 degrees, and particularly includes tangent lines that define an angle A2 relative to the lateral direction 49 of the article 20 corresponding to the previously recited suitable ranges of the angle A2. Thus, where a donning force F is applied to the article 20 in a direction that is anywhere within the range of greater than zero degrees to less than 90 degrees relative to the lateral axis 49, there is a tangent to the void 116 that suitably extends perpendicular to the direction of the donning force.

The weakening elements disposed in the absorbent structure 44 at the front and back waist regions 22, 24 of the absorbent article 20 may alternatively be mirror images of each other, such is in the manner of the slits 100, 106, 110 in the embodiments of FIGS. 3-5, as well in the embodiment of FIG. 7 wherein weakening elements 120 comprise elongate voids that are generally rectangular in shape. It is also contemplated that the elongate voids may be shaped other than elliptical, ovate or rectangular and remain within the scope of this invention. For example, some of the weakening elements 124 disposed in the absorbent structure 44 of the article 20 shown in FIG. 8 are generally semi-elliptical or semi-ovate voids, with the outermost elements (e.g. nearest the corner regions 94) being generally semi-circular voids. It is also understood that the elongate voids 116, 120, 124 may be irregular shaped without departing from the scope of this invention.

While not shown in the drawings, it is alternatively contemplated that the voids 116, 120, 124 need not be elongate. For example, the voids may be circular, square or other non-elongate shape, as long as either a portion of the void extends in a direction that defines an angle A2 relative to the lateral direction 49, or a tangent to the void extends in a direction that defines an angle A2 relative to the lateral direction, that is greater than zero degrees and less than 90 degrees, more suitably greater than zero degrees and less than or equal to about 60 degrees, and even more suitably greater than zero degrees and less than or equal to about 30 degrees.

In use, the weakening elements disposed in the absorbent structure 44 increase the stretchability of the absorbent article 20 and allow easier donning by reducing the amount of tension (e.g., donning force) required to expand the dimensions of the article. For example, with respect to the training pants 20, weakening elements disposed in the absorbent structure 44 of the pants, particularly adjacent the corner regions 94 of the absorbent structure as in the previously described embodiments, increase the stretchability of the absorbent structure 44 in the common direction of application of the donning force so that less force is required to expand the waist opening 50 of the article 20 while pulling on the pants.

The weakening elements disposed in the absorbent structure may be made using a variety of conventional techniques. For example, the weakening elements may be cut into the absorbent structure 44 by a separate cutting process after initial formation of the absorbent structure. Other conventional techniques such as ultra-sonic non-contact cutting techniques may be used to form slits in the absorbent structure 44. Alternatively, the weakening elements may be formed into the absorbent structure 44 by techniques such as blocking air flow to a forming screen during an airforming process as is know in the art.

In the event that the absorbent structure 44 includes a suitable wrap, the wrap may also be stretchable and/or include suitable weakening elements, substantially similar to the weakening elements in the absorbent structure, to enhance the stretchability of the article 20.

Figure 9:
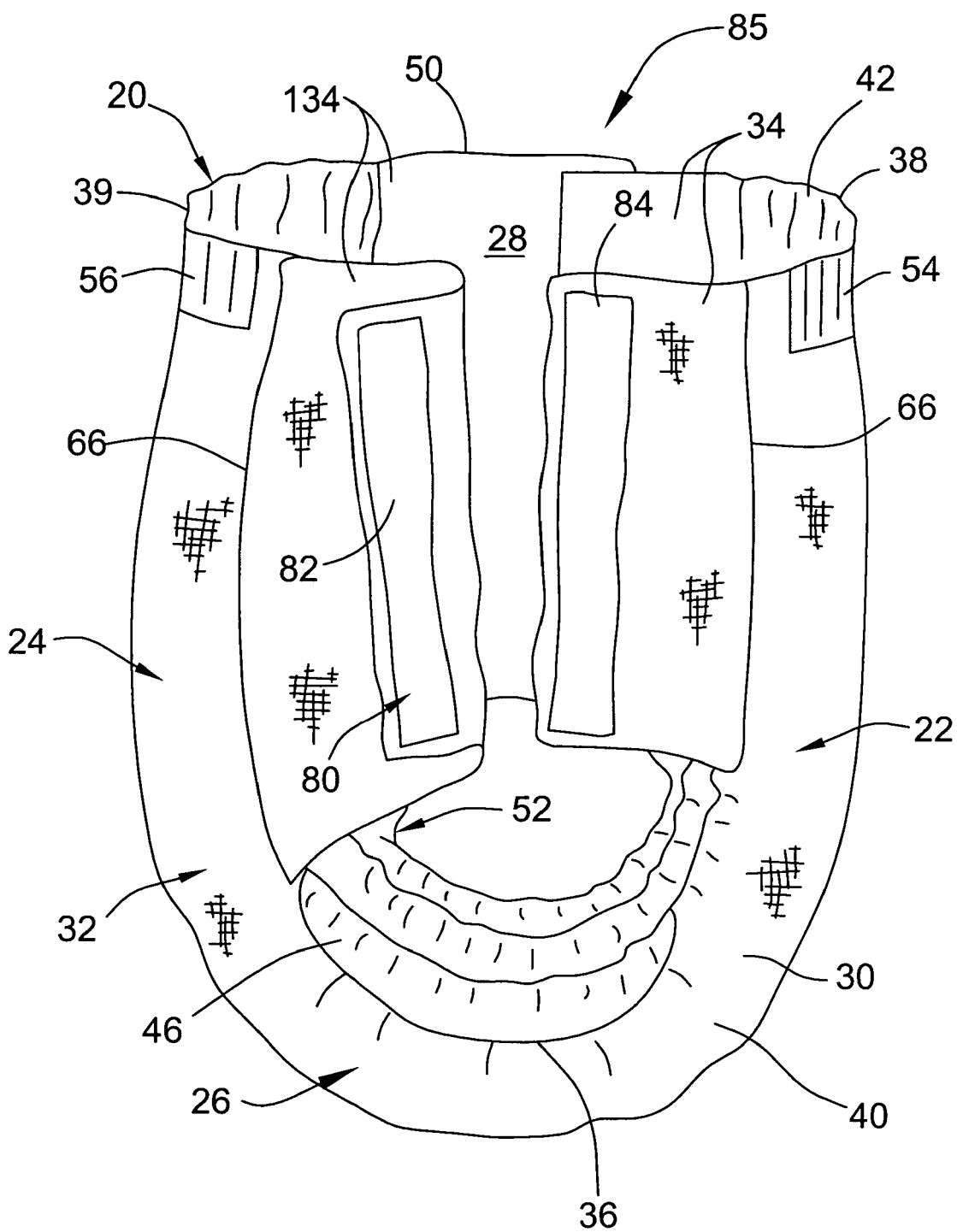
FIG. 9 illustrates a side perspective of another aspect of the present invention shown in the form of a pair of training pants having a pair of separately attached side panels and a mechanical fastening system fastened on one side of the training pants and unfastened on the opposite side thereof.
Figure 10:
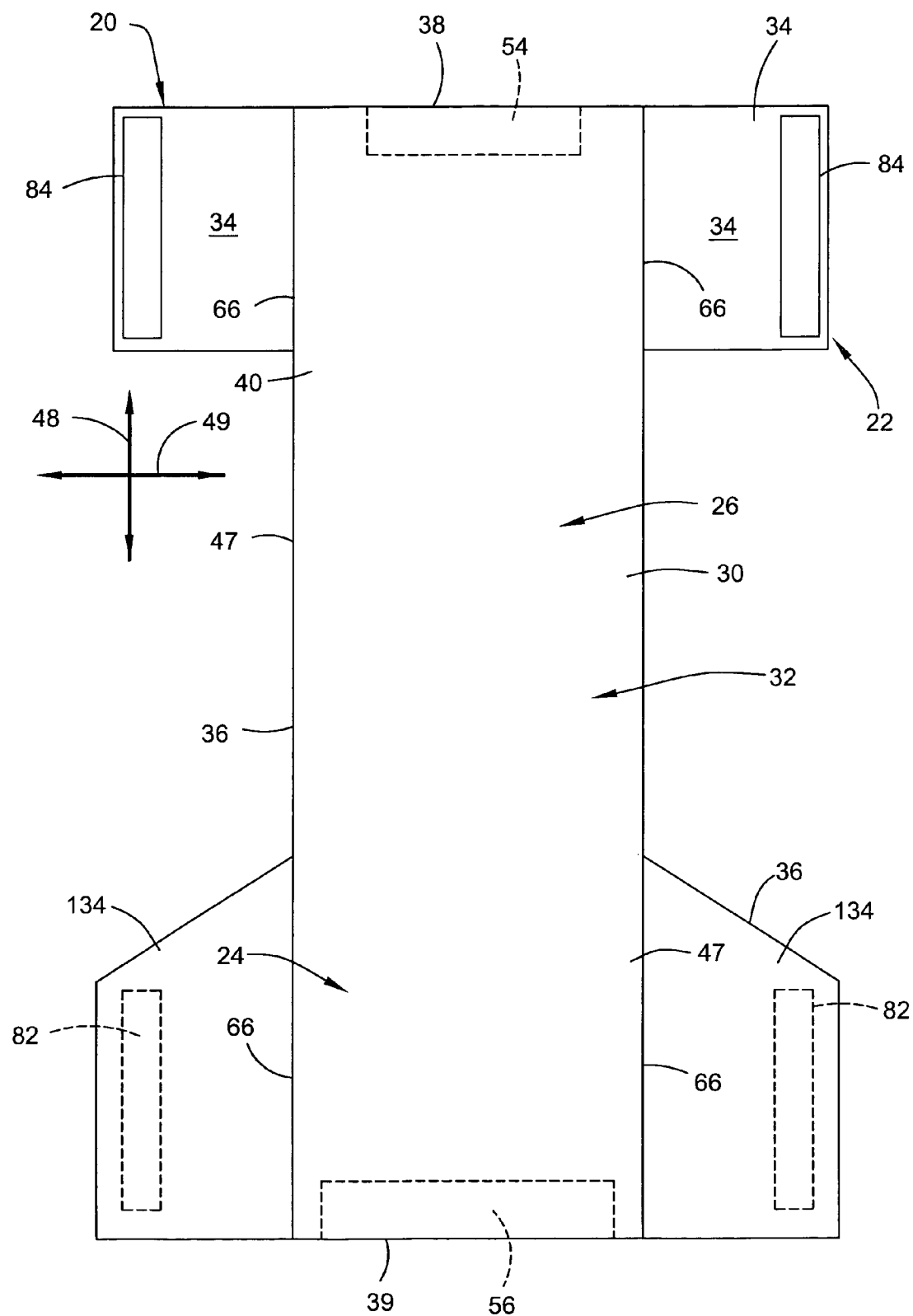
FIG. 10 illustrates a bottom plan view of the training pants of FIG. 9 with the pants in an unfastened, unfolded and laid flat condition, and showing the surface of the training pants that faces away from the wearer.
Figure 11:
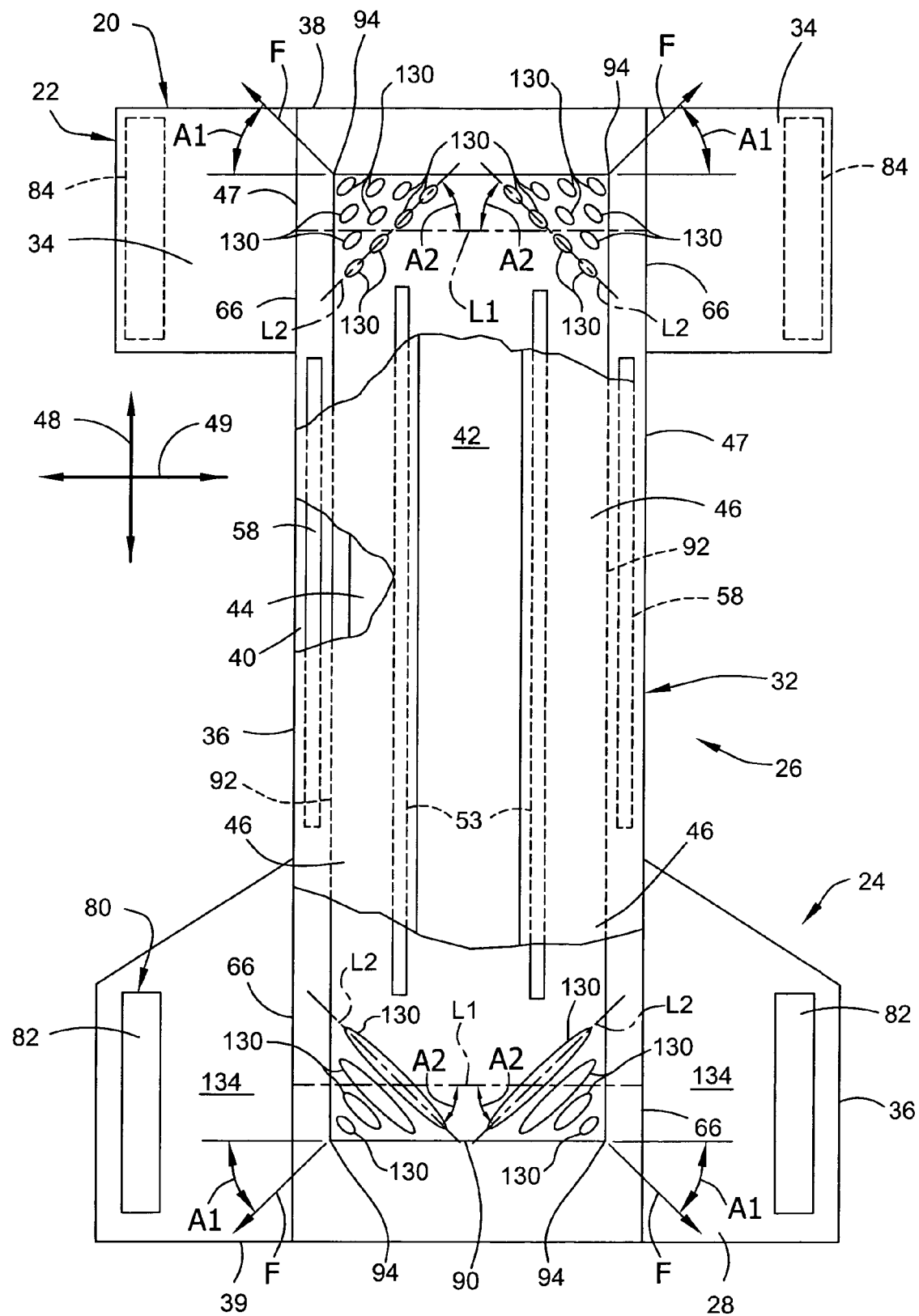
FIG. 11 illustrates a top plan view similar to FIG. 10 showing the surface of the training pants that faces the wearer when worn and with portions cut away to show underlying features.
Figure 14:
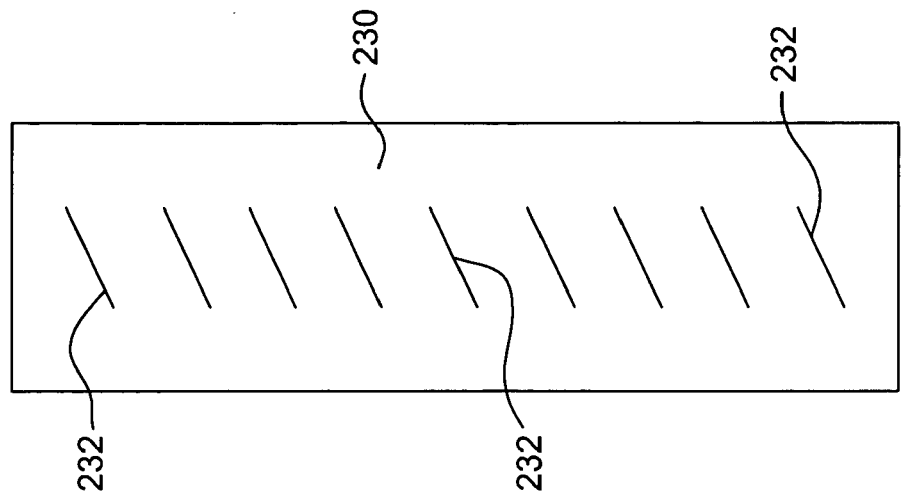
Figure 13:
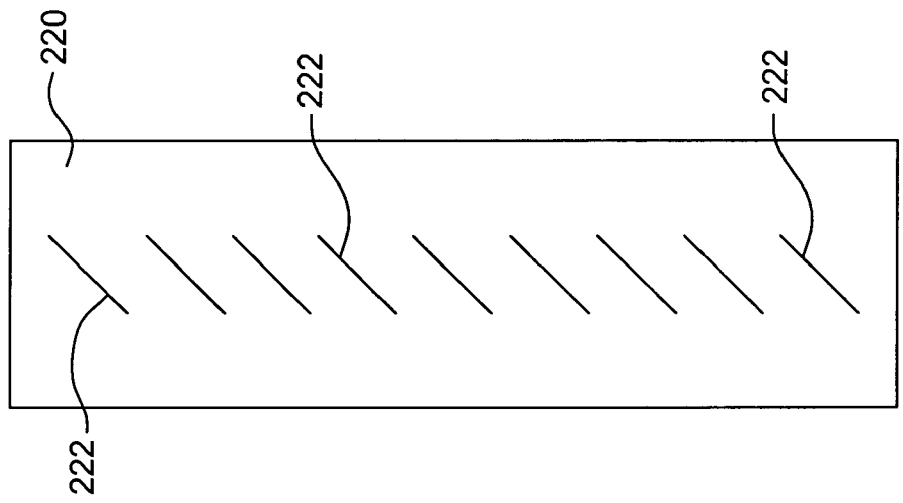

FIGS. 9-11 illustrate another embodiment of the present invention wherein the absorbent article is the form of training pants 20 comprising a generally rectangular central absorbent assembly 32 and side panels 34, 134 formed separately from and secured to the central absorbent assembly. The side panels 34, 134 are permanently bonded along seams 66 to the central absorbent assembly 32 in the respective front and back waist regions 22 and 24 of the pants 20. More particularly, as seen best in FIGS. 10 and 11, the front side panels 34 can be permanently bonded to and extend transversely outward beyond side margins 47 of the absorbent assembly 32 at the front waist region 22, and the back side panels 134 can be permanently bonded to and extend transversely outward beyond the side margins of the absorbent assembly at the back waist region 24. The side panels 34 and 134 may be bonded to the absorbent assembly 32 using attachment means known to those skilled in the art such as adhesive, thermal or ultrasonic bonding.

The front and back side panels 34 and 134, upon wearing of the pants 20, thus comprise the portions of the training pants 20 which are positioned on the hips of the wearer. The front and back side panels 34 and 134 can be permanently bonded together to form the three-dimensional configuration of the pants 20, or be releasably connected with one another such as by the fastening system 80 of the illustrated aspects.

In the embodiment of FIGS. 9-11, the side panels 34, 134 comprise an elastic material capable of stretching at least in a direction generally parallel to the lateral direction 49 of the training pants 20. Suitable elastic materials, as well as one process of incorporating elastic side panels into training pants, are described in the following U.S. patents: U.S. Pat. No. 4,940,464 issued Jul. 10, 1990 to Van Gompel et al.; U.S. Pat. No. 5,224,405 issued Jul. 6, 1993 to Pohjola; U.S. Pat. No. 5,104,116 issued Apr. 14, 1992 to Pohjola; and U.S. Pat. No. 5,046,272 issued Sep. 10, 1991 to Vogt et al.; all of which are incorporated herein by reference. In particular aspects, the elastic material may include a stretch-thermal laminate (STL), a neck-bonded laminate (NBL), a reversibly necked laminate, or a stretch-bonded laminate (SBL) material. Methods of making such materials are well known to those skilled in the art and described in U.S. Pat. No. 4,663,220 issued May 5, 1987 to Wisneski et al.; U.S. Pat. No. 5,226,992 issued Jul. 13, 1993 to Morman; European Patent Application No. EP 0 217 032 published on Apr. 8, 1987 in the name of Taylor et al.; and PCT application WO 01/88245 in the name of Welch et al.; all of which are incorporated herein by reference. Alternatively, the side panel material may include other woven or non-woven materials, such as those described herein as being suitable for construction of the outer cover 40 and/or the bodyside liner 42; mechanically pre-strained composites; or stretchable but inelastic materials.

As shown in FIG. 11, this embodiment may have weakening elements 130 arranged generally adjacent the corner regions 94 of the absorbent structure 44 to increase the stretchability of the absorbent structure in the direction of the donning force F applied to the pants 20. As with the previous embodiments, the weakening elements 130 of the absorbent structure 44 may be slits or voids or other suitable weakening elements. The weakening elements 130 may be located in the absorbent structure at the various locations and orientations as discussed above for the previous embodiments.

EXPERIMENT 1

A Material Elongation Tensile Test, as described later herein, was used to test the effect of different weakening element sizes and patterns for absorbent structures. All test samples were 3"×12" (7.6 cm×30.48 cm) strips of coform absorbent structure material having a target basis weight of about 425 gsm (12.3 osy) and a density of 0.31 g/cc (0.18 o/ci). The tensile force applied to each sample during test was directed in the longitudinal direction of each sample.

The various sample weakening element patterns that were tested in this first experiment are depicted in FIGS. 12-20. Sample 1 (FIG. 12) is a control sample 210 of an absorbent structure that does not include any weakening element or other modification to the structural integrity of the sample.

Sample 2 (FIG. 13) is a strip of absorbent structure 220 substantially similar to Sample 1 except that Sample 2 has nine slits 222 (i.e., weakening elements) passing through the strip of material. Each slit 222 is approximately one inch (25.4 mm) in length and is oriented approximately 60 degrees from the lateral direction of the sample 220. Therefore, the slits 222 of Sample 2 are angled approximately 30 degrees relative to the direction of application (longitudinal) of the tensile force. The slits 222 are generally centered on the strip 220 and are spaced longitudinally from each other a distance of approximately one inch.

Sample 3 (FIG. 14) is a strip of absorbent structure 230 substantially similar to Sample 2 except the nine one-inch (25.4 mm) slits 232 passing through the material are oriented at approximately 30 degrees with respect to the lateral direction. The slits 232 of Sample 3 are thus angled approximately 60 degrees relative to the tensile force applied longitudinally of the sample 230.

Sample 4 (FIG. 15) is a strip of absorbent structure 240 substantially similar to Sample 3 except the slits 242 are oriented in the lateral direction of the sample. Each slit 242 of Sample 3 is thus oriented substantially perpendicular to the tensile force applied longitudinally of the sample 240.

Sample 5 (FIG. 16) is a strip of absorbent structure 250 substantially similar to Sample 4 except the slits 252 are approximately two inches (50.8 mm) in length instead of one inch (25.4 mm).

Sample 6 (FIG. 17) is a strip of absorbent structure 260 substantially similar to Sample 5 except the slits 262 are spaced longitudinally from each other a distance of approximately one-half inch (12.7 mm). Consequently, the Sample 6 absorbent structure 260 has twice as may slits 262 as the Sample 5 absorbent structure 250.

Sample 7 (FIG. 18) is a strip of absorbent structure 270 substantially similar to Sample 4 except that the sample 7 structure includes five one-inch (25.4 mm) slits 272 centered on the strip and spaced longitudinally by a distance of two inches (50.8 mm). Sample 7 has four pairs of one-inch (25.4 mm) slits 274 laterally offset from the centerline of the strip 270 and longitudinally spaced from the centered slits 272 by a distance of one inch (25.4 mm). Each offset slit 274 of each pair passes through the laterally opposite side edges of the sample 270. Sample 7 comprises a combined total of 13 slits 272, 274.

Sample 8 (FIG. 19) is a strip of absorbent structure 280 substantially similar to Sample 7 except the longitudinal spacing between slits 282, 284 is reduced to one-half inch (12.7 mm) and each pair of slits 284 offset from the centerline of the strip has been moved laterally inward from the side edges of the strip. Also, the lateral spacing between each pair of slits has been reduced to one-half inch (12.7 mm).

Sample 9 (FIG. 20) is a strip of absorbent material 290 substantially similar to Sample 8 except the offset slits 294 have been moved laterally outward to extend to the laterally opposite side edges of the strip. Also, the lateral spacing between each pair of slits 292, 294 has been increased to one inch (25.4 mm).

Figure 21:
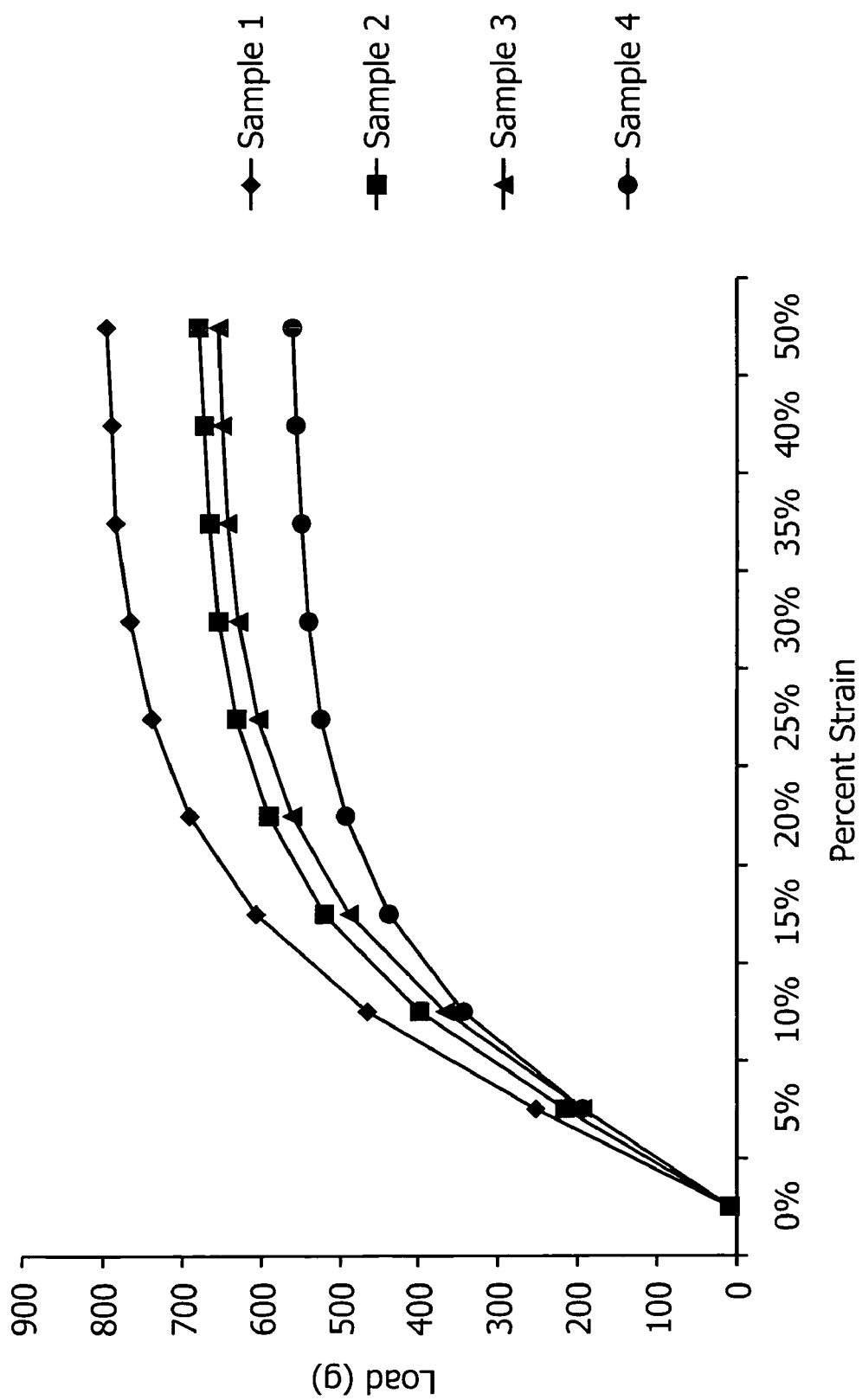
FIGS. 21-24 illustrate a comparison of the data obtained for the samples involved in the experiment.

Plots comparing the test results of the first experiment are provided in FIGS. 21-24. Specifically, a comparison of Samples 1, 2, 3, and 4 is shown in FIG. 21. The Sample 4 absorbent structure 240 having slits 242 oriented perpendicular to the tensile force required less force to produce the same amount of percent strain or elongation of the Sample. Thus, a slit (e.g., weakening element) having a maximum length dimension oriented perpendicular to an applied force is advantageous as compared to a slit of the same length having a maximum length dimension oriented other than perpendicular to the applied force.

Figure 22:
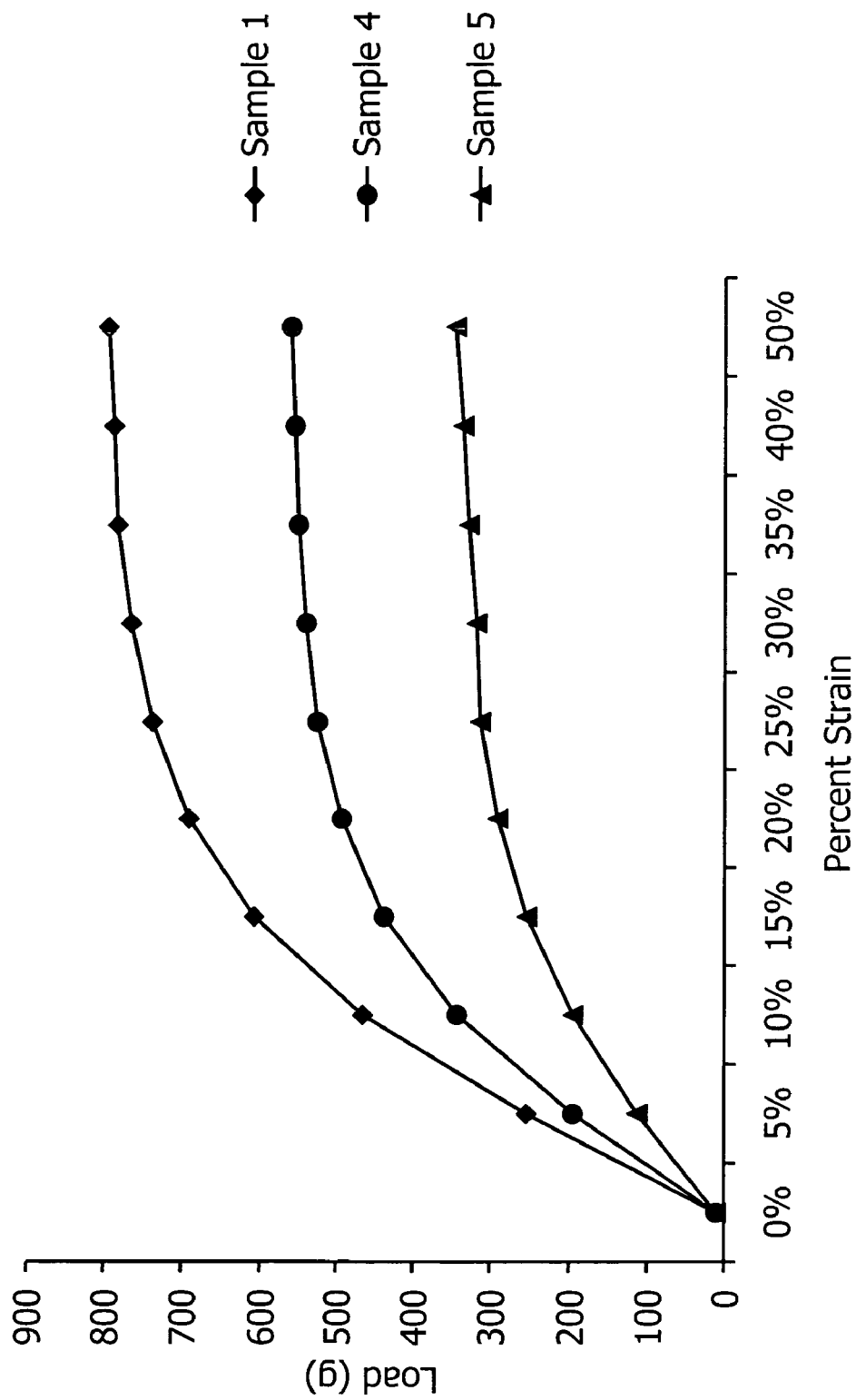

FIG. 22 compares the Sample 5 absorbent structure 250, having two inch (50.8 mm) slits 252 disposed therein, to the Sample 4 absorbent structure 240 having one inch (25.4 mm) slits 242. As can be seen, providing the longer slits 252 substantially reduced the load-strain curve of the absorbent structure 250.

Figure 23:
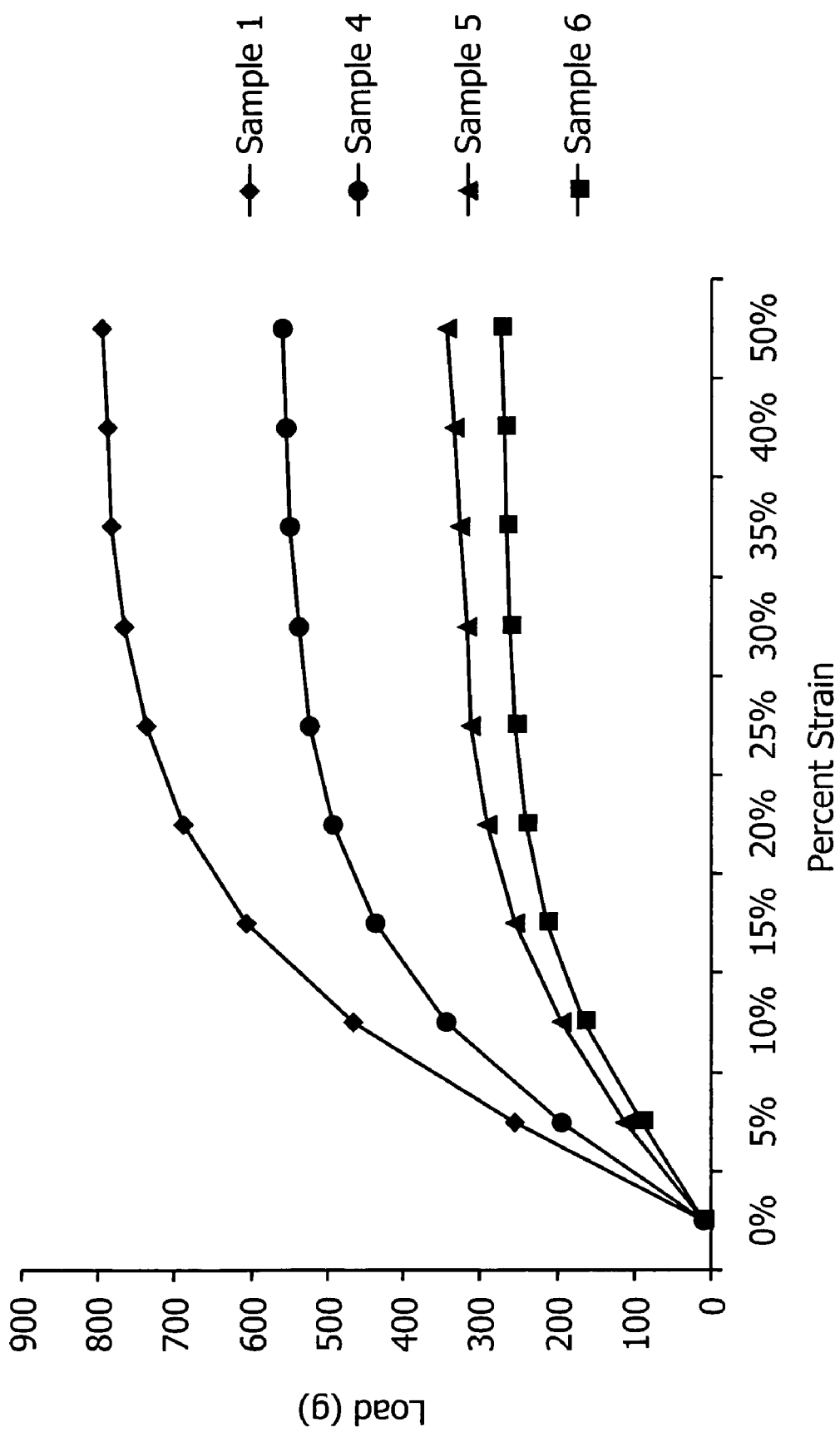

FIG. 23 additionally compares the longitudinally closely spaced slits 262 of the Sample 6 structure 260 to the Sample 5 structure 250. This comparison indicates that Sample 6 having two inch (50.8 mm) slits 262 spaced every half inch (12.7 mm) required less tensile force to produce the same amount of elongation as for Sample 5.

Figure 24:
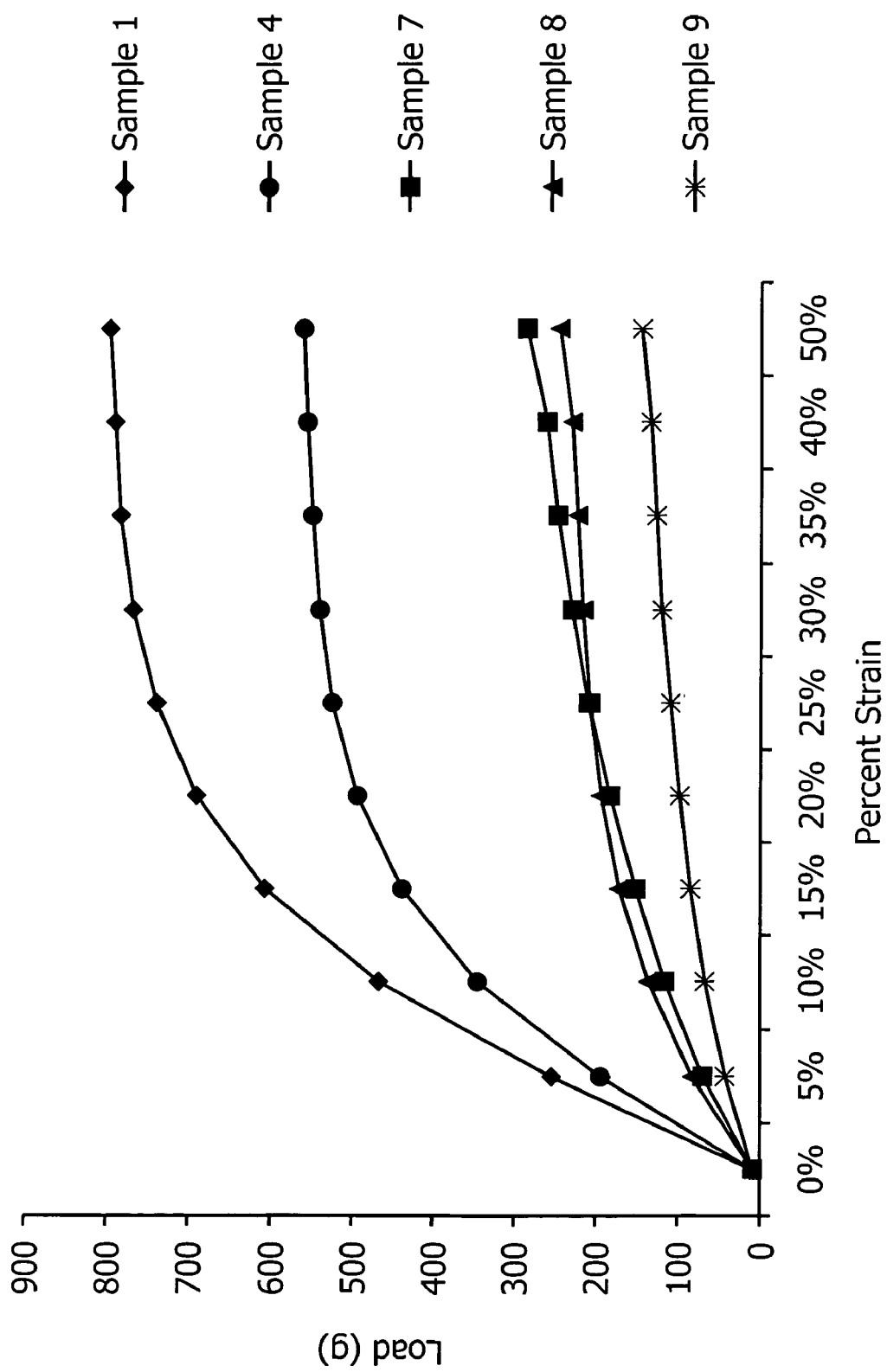
Figure 28:
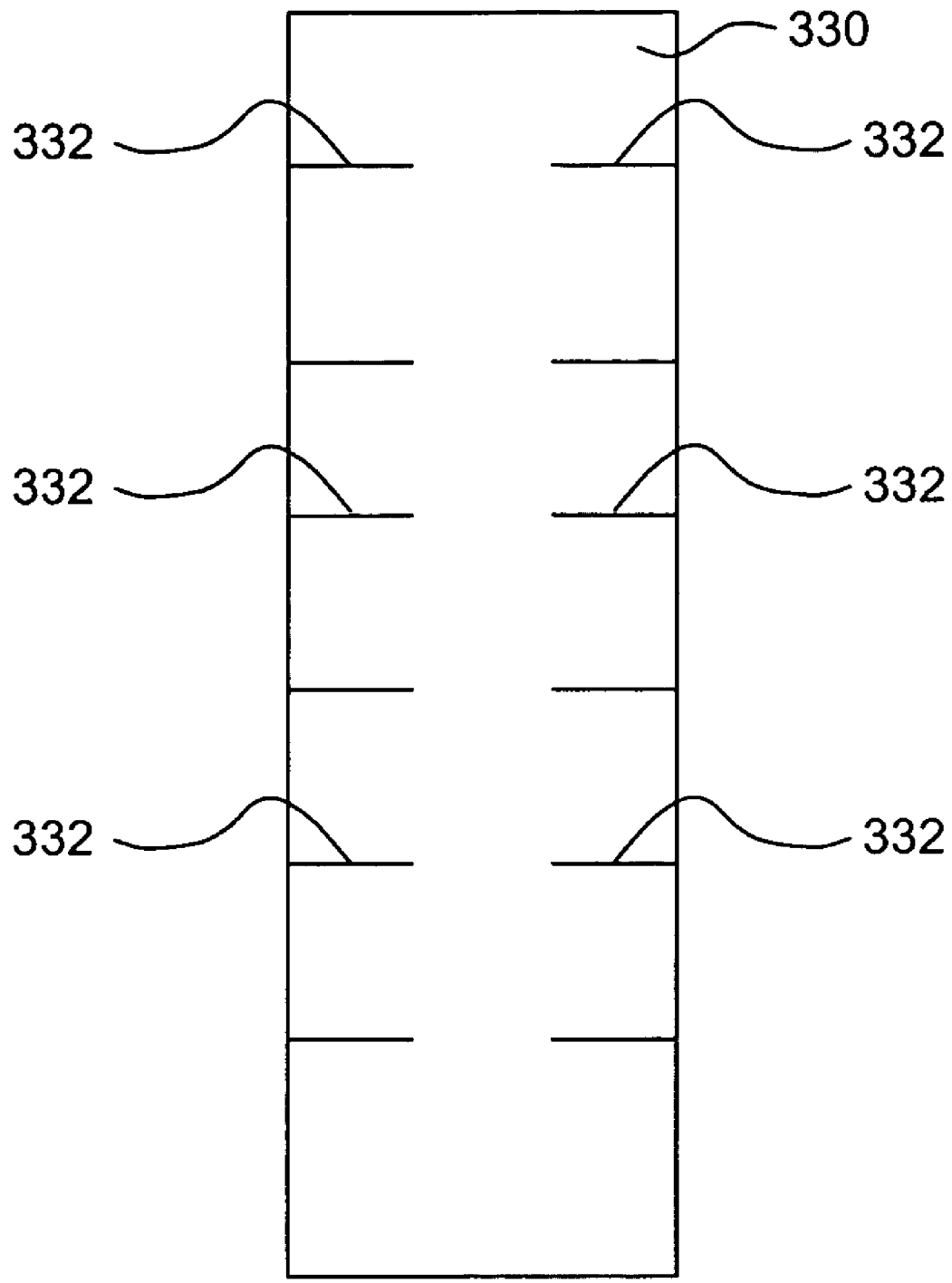

FIG. 24 is a comparison of Samples 1, 4, 7, 8, and 9. Sample 9, having longitudinally extending one inch (25.4 mm) slits 292, 294 every one-half inch (12.7 mm) and alternating pairs of longitudinally extending slits 294 that extend to the side edges of the sample 290 had the lowest load-strain curve of all the Samples tested.

EXPERIMENT 2

A second experiment was performed using the Material Elongation Tensile Test, as described later herein, to test the effect of extending the weakening elements to the lateral side edges of the sample. As with the first experiment, all test samples were 3"×12" (7.6 cm×25.4 cm) strips of coform absorbent structure material having a target basis weight of about 425 gsm (12.3 osy) and a density of 0.31 g/cc (0.18 o/ci). The tensile force applied to each sample during the test was directed in the longitudinal direction of each sample.

Figure 12:
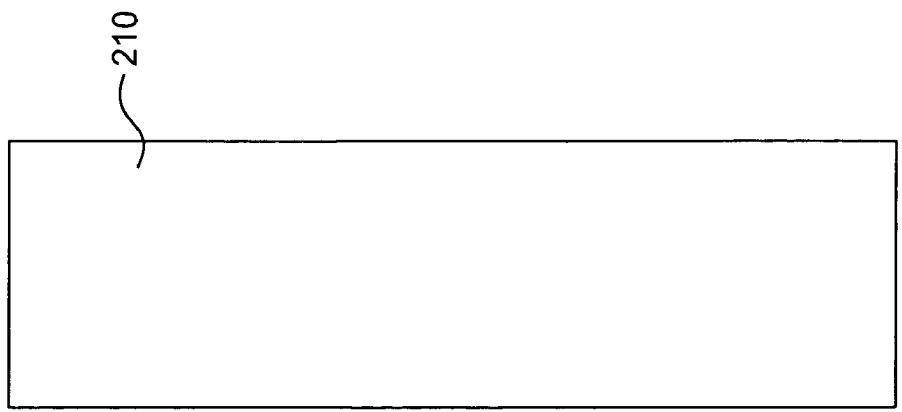
Figure 17:
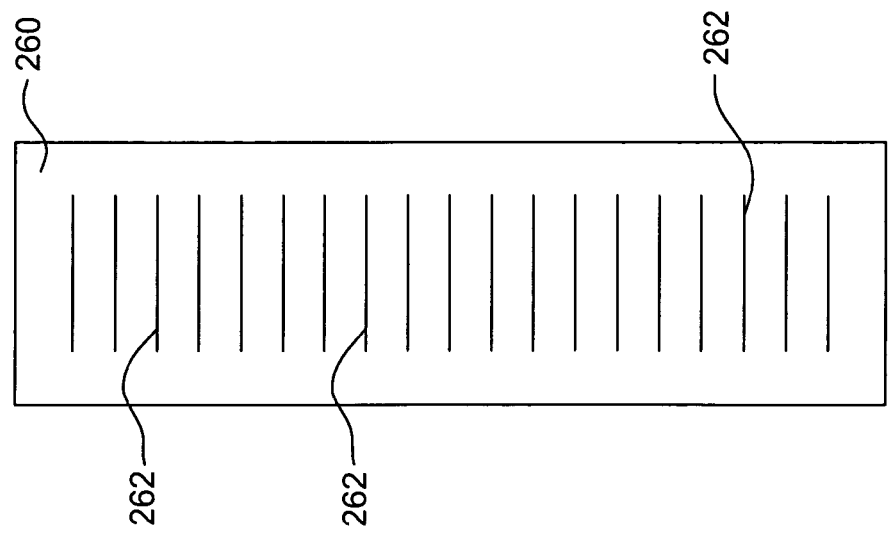
Figure 16:
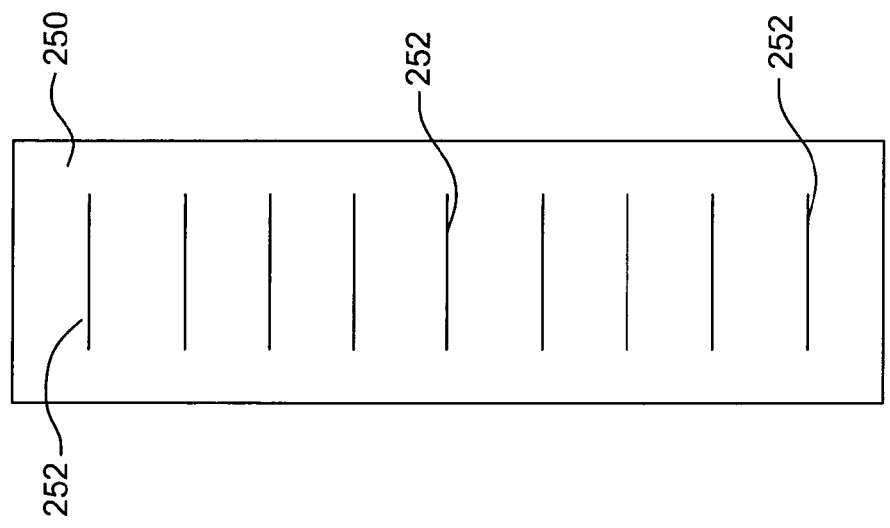
Figure 15:
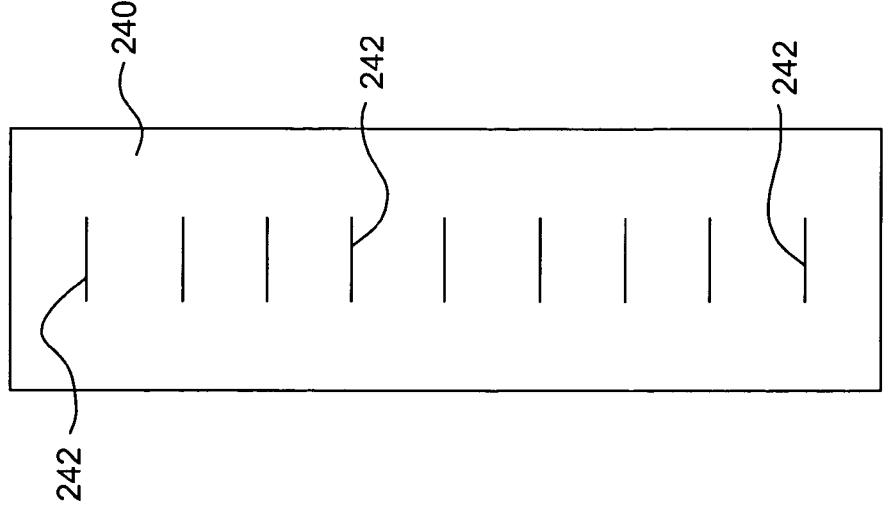

In addition to the Sample 1 control sample depicted in FIG. 12, the additional sample weakening element patterns that were tested in the second experiment are depicted in FIGS. 25-28. Sample 10 (FIG. 25) is a strip of absorbent structure 300 substantially similar to Sample 1 except that Sample 10 has six one-inch (25.4 mm) slits 302 oriented in the lateral direction of the article. The slits 302 are centered on the sample 300 and spaced in from the lateral side edges of the sample.

Sample 11 (FIG. 26) is a strip of absorbent structure 310 substantially similar to Sample 10 except that the sample has pairs of one-inch (25.4 mm) slits 312 oriented on opposed lateral side edges of the structure. Sample 11 has three rows of slits 312 for a total of six one-inch (25.4 mm) slits on the lateral side edges of the sample 310.

Sample 12 (FIG. 27) is a strip of absorbent structure 320 substantially similar to Sample 10 except that twelve one-inch (25.4 mm) slits 322 are provided and more closely spaced than the one-inch (25.4 mm) slits 302 of Sample 10. None of the slits 322 of this sample 320 extend to the lateral side edges of the sample.

Sample 13 (FIG. 28) is a strip of absorbent structure 330 substantially similar to Sample 11 except six rows of slits 332 are provided, each row comprising a pair of slits on the opposed lateral side edges of the structure. Sample 13 comprises a total of twelve one-inch (25.4 mm) slits 332 that are more closely spaced in the longitudinal direction than the six slits 312 of Sample 11.

Figure 29:
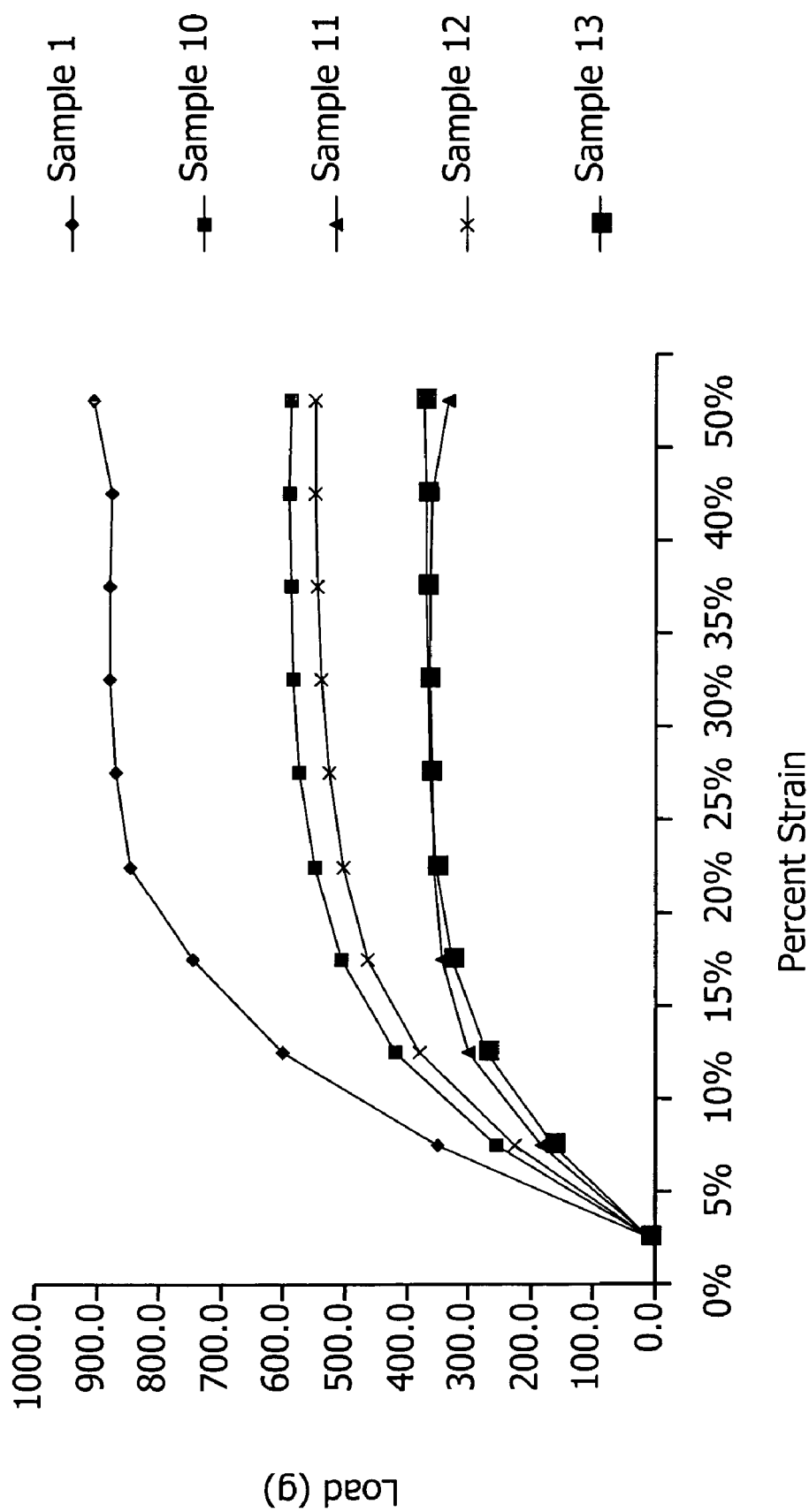
FIG. 29 illustrates a comparison of the data obtained in the second experiment.

FIG. 29 is a plot showing the results of the second experiment including a comparison of the test results for Samples 1 and 10-13. Samples 11 and 13, having slits on the lateral side edges of the sample, required less force to produce the same amount of percent strain or elongation of the Sample. Thus, a slit (e.g., a weakening element) extending to (e.g. intersecting) a lateral side edge or longitudinal edge margin of the absorbent structure is advantageous compared to a slit spaced in from the edges of the absorbent structure. The slits on the lateral side edges of Sample 11 and 13 were observed to promote a narrowing of the sample width (i.e., "necking") near the lateral centerline of the sample. The results of the second experiment show that the necking that occurs in the samples having the slits extending to the edge margin promotes stretching of the sample and allows elongation of the sample at a lower force than a sample having slits spaced in from the lateral side edges of the sample.

EXPERIMENT 3

A third experiment was performed using the Material Elongation Tensile Test, as described later herein, to test the effect that weakening elements provided in the absorbent structure have on lateral stretch distribution of the article. The lateral stretch distribution of the absorbent article 20 as used herein refers to the distribution of stretch across the lateral width of the absorbent article that occurs upon expansion of the waist opening 50 of the article.

In this experiment, five test samples were tested using the Material Elongation Tensile Test. The samples were cut from a rectangular shaped composite comprising a stretchable outer cover layer and stretchable bodyside liner layer with an absorbent layer disposed therebetween and adhered to both the bodyside liner and the outer cover. The outer cover and liner had a length of approximately 500 mm and a width of approximately 250 mm. The absorbent structure had a length and width of approximately 250 mm so that the absorbent structure was only present in approximately half of the composite. In the half of the composite without absorbent structure the outer cover and liner were adhered together with an adhesive. The area including absorbent structure between the outer cover and liner formed an attachment zone of the composite and the area in which the outer cover was adhered directly to the liner formed a non-attachment zone of the composite.

The absorbent structure of the composite comprised a coform absorbent structure material with a target basis weight of about 425 gsm (12.3 osy) and a density of 0.31 g/cc (0.18 o/ci). The absorbent structure of the composite had weakening elements of the present invention in the form of elongate slits through the absorbent structure having various lengths.

The outer cover of the composite comprised a stretchable film/nonwoven laminate produced with the following materials and processes. A film layer filler concentrate comprised of 75% calcium carbonate was dispersed into a polymeric carrier resin. The calcium carbonate, available from Omya, Inc. North America of Proctor, Vt., and designated as 2SST, has an average particle size of 2 microns with a top cut of 8-10 microns and a coating of approximately 1% stearic acid. The polymeric carrier resin which comprises 25% of the blend was a DOWLEX 2517 LLDPE resin supplied by Dow Chemical U.S.A. of Midland Mich. DOWLEX 2517 has a density of 0.917 g/cc (0.530 o/ci) and a melt index of 25. The 75/25 blend of calcium carbonate and LLPE resin was subsequently blended with 33% of SEPTON 2004 which is a SEPS based styrenic block copolymer to provide a final calcium carbonate concentration of 50.25% by weight. The SEPTON resin is available from Septon Company of America of Pasadena, Tex.

The formulation was formed into a film by casting onto a chill roll set to 38° C. (100° F.) at an unstretched basis weight of approximately 67 gsm (1.9 osy). The casting speed was 125 ft/minute (38.1 m/minute). The film was heated to a temperature of 47.5° C. (125° F.), stretched 3.9 times its original length using a machine direction orientor at a line speed of 493 ft/minute (150 m/minute). The film was retracted 0% resulting in a stretched basis weight of approximately 33 gsm (1.0 osy). As used herein, stretching 3.9 times means that a film which, for example, had an initial length of 1 meter if stretched 3.9 times would have a final length of 3.9 meters. The film was then annealed at a temperature of 42° C. (110° F.) across multiple rolls at a line speed of 493 ft/minute (150 m/minute).

The fibrous nonwoven web was a 20 gsm (0.58 osy) spunbond web produced by BBA Materials Technology of Nashville, Tenn. with the trade name of Sofspan 120. The fibrous nonwoven web was introduced into a nip of intermeshing grooved steel rolls at a velocity of 146.9 meters/min (482 ft/m) with the grooves in the rolls being concentric. Each groove was formed with a depth of 0.51 cm (0.200") and with a peak to peak distance of 0.31 cm (0.125") resulting in a maximum draw ratio of 3.4×. The spunbond was stretched to a draw of 2.6× or 160% in the cross direction (CD). The fibrous nonwoven web was heated to a temperature of 93.3° C. (200° F.) while it passed subsequently under a hot air knife and through the temperature controlled nip between grooved rolls set to intermeshing engagement of 3.81 mm (0.150"). The spunbond was drawn 2% in the machine direction between the groove roll unit and the lamination unit causing the CD width to be necked in 5% (even though it had been stretched in the CD by the grooved rolls) to a new width of 50.80 cm (20 inches).

Lamination of the film and nonwoven layer was accomplished using adhesive lamination with a slot die coater. HX9375-01 adhesive, produced by Bostik Findley corporation of Wauwautosa, Wis., was melted to a temperature of 177° C. (350° F.) and applied to the spunbond sheet with an add-on level of 1 gsm (0.03 osy).

The produced laminate for the outer cover material was retracted 10% in the machine direction between the lamination unit and fourth roll in the annealing unit maintaining its width. The laminate was annealed and cooled using 4 temperature controlled rolls. The laminate with the film side in contact with the rolls was heated at 82° C. (180° F.) over two rolls and then cooled at 16° C. (60° F.) over the next two rolls to set the final machine and cross direction stretch material properties. Finally the laminate was transferred with minimal retraction to the winder for a final basis weight of 59 gsm (1.7 osy).

The bodyside liner of the composite comprised a 0.3 osy (10.2 gsm) polypropylene spunbond web that was creped 60% and necked 60%. The terms "creped" or "crepe" refer to a crinkled material or composite having bonded and unbonded areas. The creped material can be returned to approximately its original length by applying a mechanical stress, thus smoothing out the crinkled portions. Necked" or "neck stretched" are interchangeable terms and refer to a method of elongating a nonwoven fabric, generally in the longitudinal, or machine direction, to reduce its width in a controlled manner to a desired amount. The controlled stretching may take place under cool, room temperature or greater temperatures and is limited to an increase in overall dimension in the direction being stretched up to the elongation required to break the fabric, which in most cases is about 1.2 to 1.4 times. When relaxed, the web retracts toward its original dimensions. Such a process is disclosed, for example, in U.S. Pat. No. 4,443,513 to Meitner and Notheis, U.S. Pat. Nos. 4,965,122, 4,981,747 and 5,114,781 to Morman and U.S. Pat. No. 5,244,482 to Hassenboehler Jr. et al.

The adhesive used to attach the outer cover and bodyside liner and/or the absorbent structure of the composite comprised a swirl adhesive available from Bostik-Findley Adhesive of Wauwautosa, Wis. and designated as H2525A.

The samples cut from the composite included a sample of outer cover and liner cut from the portion of the composite free of intervening absorbent structure (the non-attachment zone), a sample cut from the attachment zone of the composite including absorbent structure that was free of any weakening elements, and three samples cut from the attachment zone of the composite that included absorbent structure having weakening elements of various lengths. Each sample was 1"×5" (2.54 cm×12.7 cm) and was cut in the lateral direction of the composite.

The samples tested in the third experiment are depicted in FIGS. 33-37. Sample 14 (FIG. 33) is a strip 401 of the composite that was taken from the non-attachment zone of the composite so that the sample is free from absorbent structure material between the outer cover and liner.

Sample 15 (FIG. 34) is a strip of material 409 from the attachment zone of the composite having a section of the absorbent structure that is free of any weakening elements.

Sample 16 (FIG. 35) is similar to Sample 15 in that it comprises a strip of material 415 from the attachment zone of the composite. But the strip of material 415 of Sample 15 was taken from a portion of the composite that included weakening elements in the absorbent structure in the form of three ½ inch (12.7 mm) long slits 419 that extend to one of the lateral side edges of the absorbent structure of the strip. The slits 419 are spaced approximately one inch (25.4 mm) apart in the longitudinal direction of the sample 415 and pass through only the absorbent structure layer of the sample.

Sample 17 (FIG. 36) is similar to Sample 16 but includes three ¾ inch (19 mm) long slits 425 in the absorbent structure of the sample 421. As with the previous sample the slits 425 extend to one of the lateral side edges of the sample 421 and are spaced apart approximately one inch (25 mm).

Sample 18 (FIG. 37) is similar to Sample 17 except the three slits 431 in the absorbent structure are approximately one inch (25.4 mm) long and extend to both of the lateral side edges of the sample 435. The slits 431 are spaced apart approximately one inch (25.4 mm) in the longitudinal direction and pass through only the absorbent layer of the sample 435.

Figure 38:
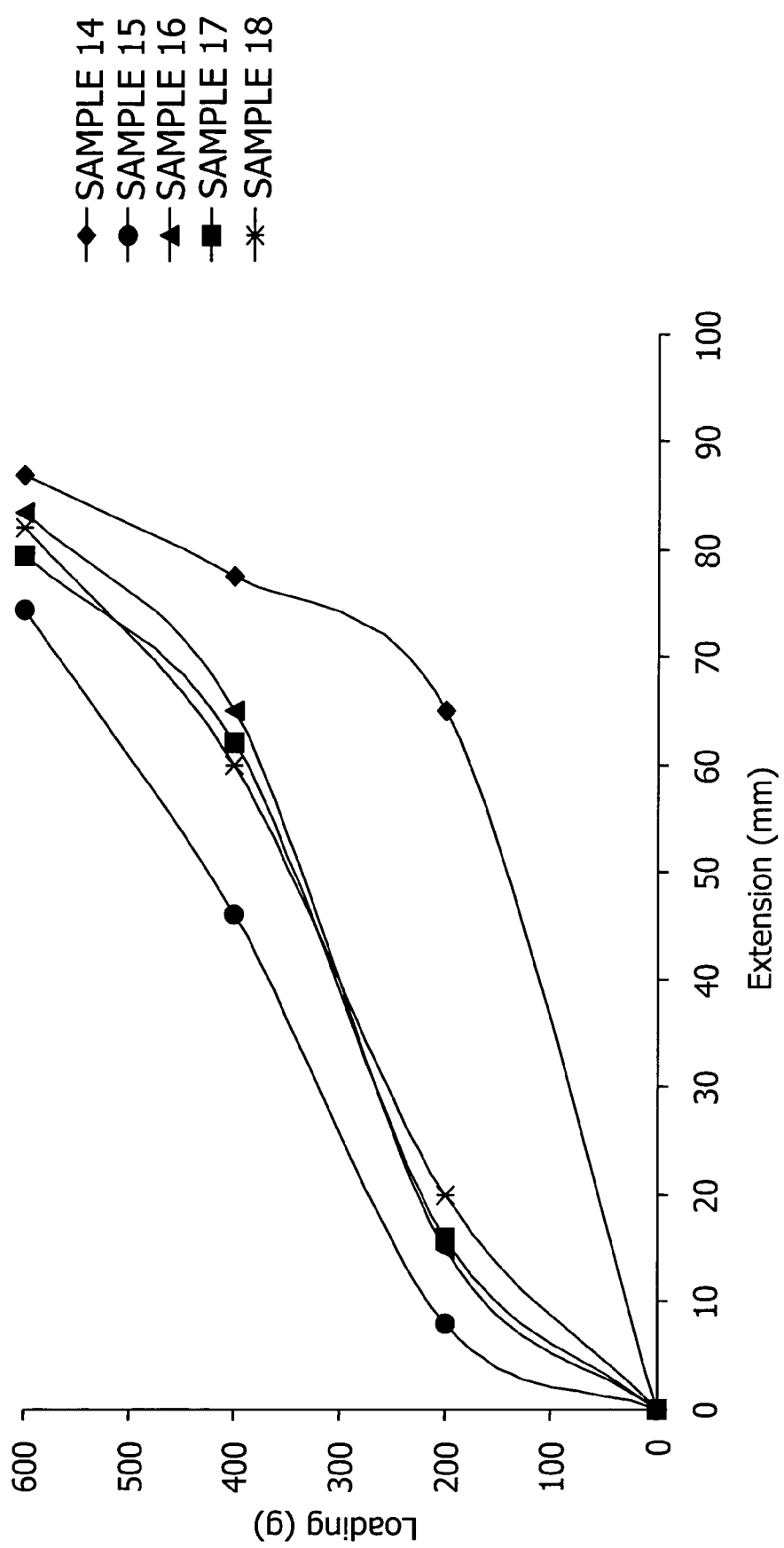
FIGS. 38-41 illustrate test data obtained in the third experiment.
Figure 39:
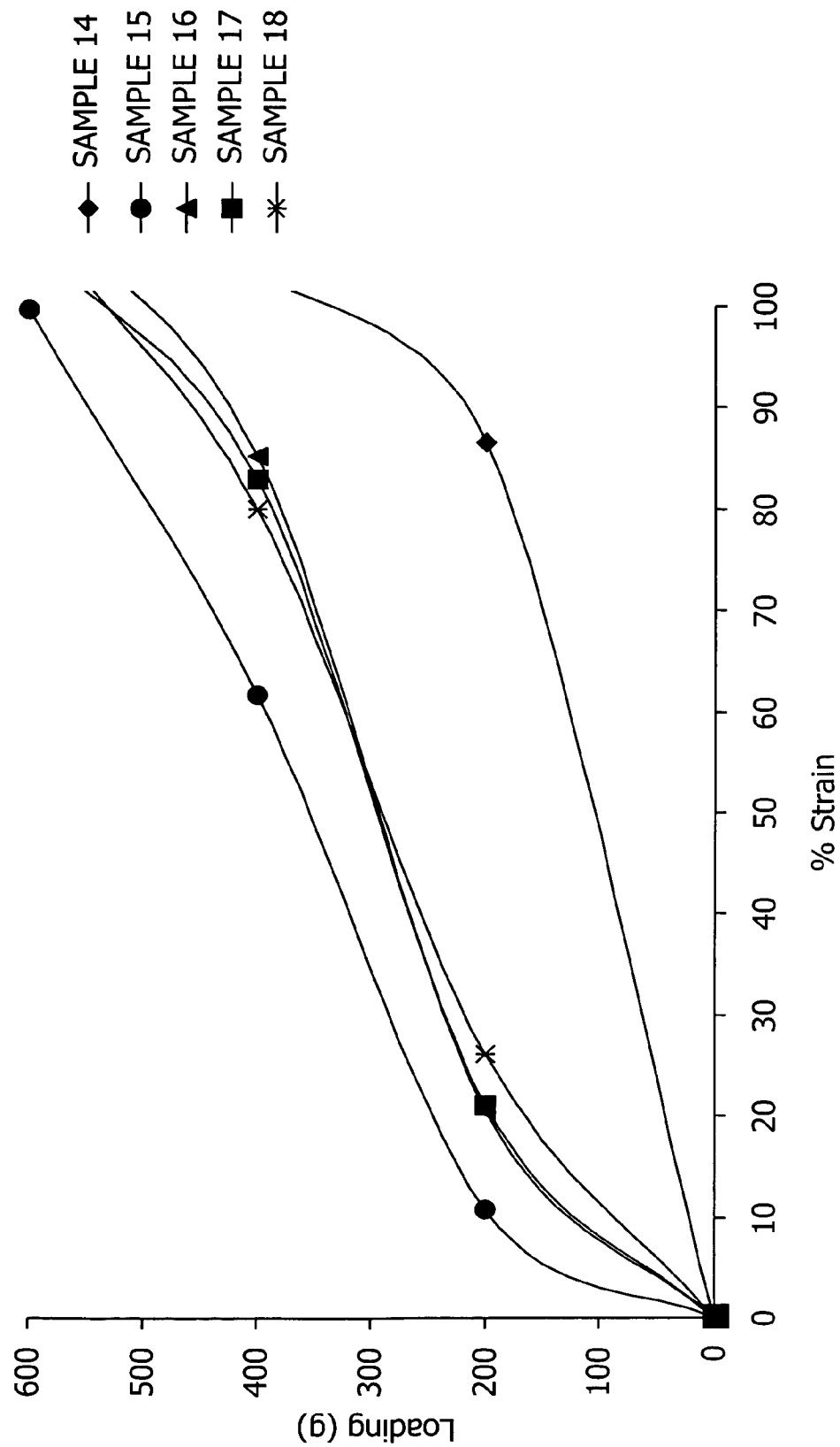

Each sample was subjected to the Material Elongation Tensile Test described below. FIGS. 38 and 39 illustrate the load versus extension curves and load versus strain curves generated for each sample. FIG. 38 shows that Samples 16-18 having an absorbent structure with weakening elements had a greater extension at a given tensile force compared to Sample 15 having an absorbent structure without weakening elements. FIG. 39 shows that Samples 16-18 having absorbent structures with weakening elements had increased strain at a given tensile force compared to Sample 15 having an absorbent structure without weakening elements.

The load versus extension curves for each sample shown in FIG. 38 were used to calculate the amount of extension energy of each sample at a specific amount of elongation. The extension energy of a sample is the amount of resistance to stretching in the sample. The amount of extension energy at a given elongation of the sample is calculated by determining the area under the load versus elongation curve (or load versus extension curve) up to the amount of elongation for each sample. The extension energy of a sample is inversely proportional to the amount of lateral stretch in the sample so that a higher extension energy means the sample will have a higher resistance to stretching and less elongation at a certain load.

The amount of extension energy of Sample 14, taken from the non-attachment zone of the composite, is compared with the amount of extension energy of each of the samples taken from the attachment zone of the composite (Samples 15-18) to determine an Extension Energy Ratio for each of Samples 15-18. That is, the Extension Energy Ratio of a respective sample comprises the extension energy of Sample 14 divided by the extension energy of the respective sample at a corresponding strain point. Therefore, the Extension Energy Ratio is a comparison of the amount of extension energy of the non-attachment zone of the composite with the amount of extension energy of the attachment zone samples having the various configurations of Samples 15-18. An Extension Energy Ratio equal to 1.0 would correspond to an ideal lateral stretch distribution in the article where an equal amount of extension energy is present in the non-attachment zone as in the attachment zone of the article.

Figure 40:
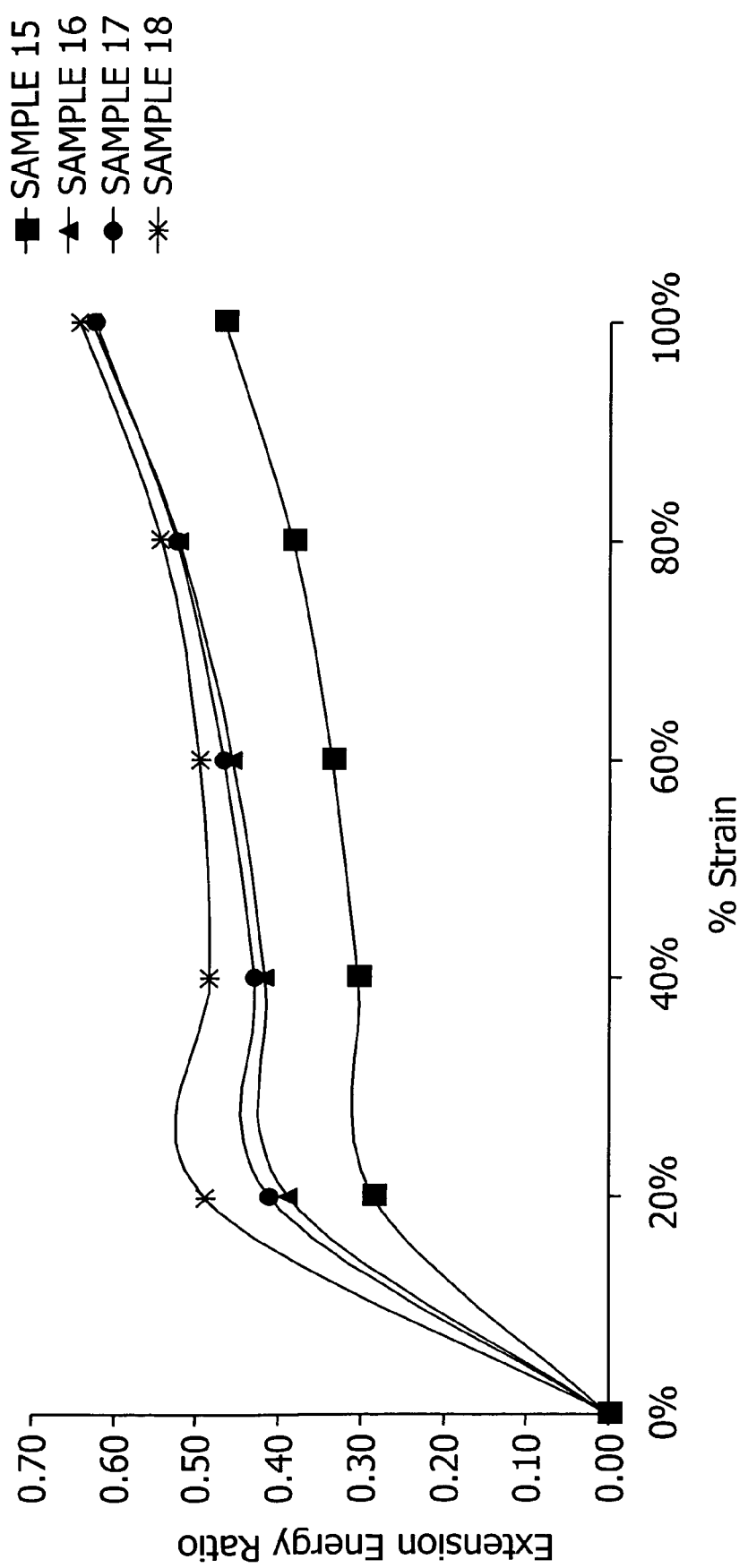

FIG. 40 is a plot showing the results of the third experiment including a comparison of the Extension Energy Ratio for Samples 15-18. The chart shows an increased Extension Energy Ratio for all the modified absorbent samples (Samples 16-18) over the non-modified absorbent sample (Sample 15). Sample 18, having slits passing through the opposed lateral side edges of the sample, had the highest ratio that was closest to the optimum value of 1.0. Thus a slit (e.g., a weakening element) extending to (e.g., intersecting) a longitudinal end of the absorbent structure and passing through the entire top or bottom waist region of the article is advantageous compared to a shorter slit extending to the longitudinal end of the absorbent structure. Typically the top waist region and bottom waist region of the article correspond to areas that are subjected to the greatest amount of lateral stretching during donning. The results of the third experiment show that samples having modified absorbent structures including weakening elements in the top waist region and bottom waist region have improved (i.e., higher) Extension Energy Ratios when compared to the Extension Energy Ratio of the sample having a non-modified absorbent structure.

Figure 41:
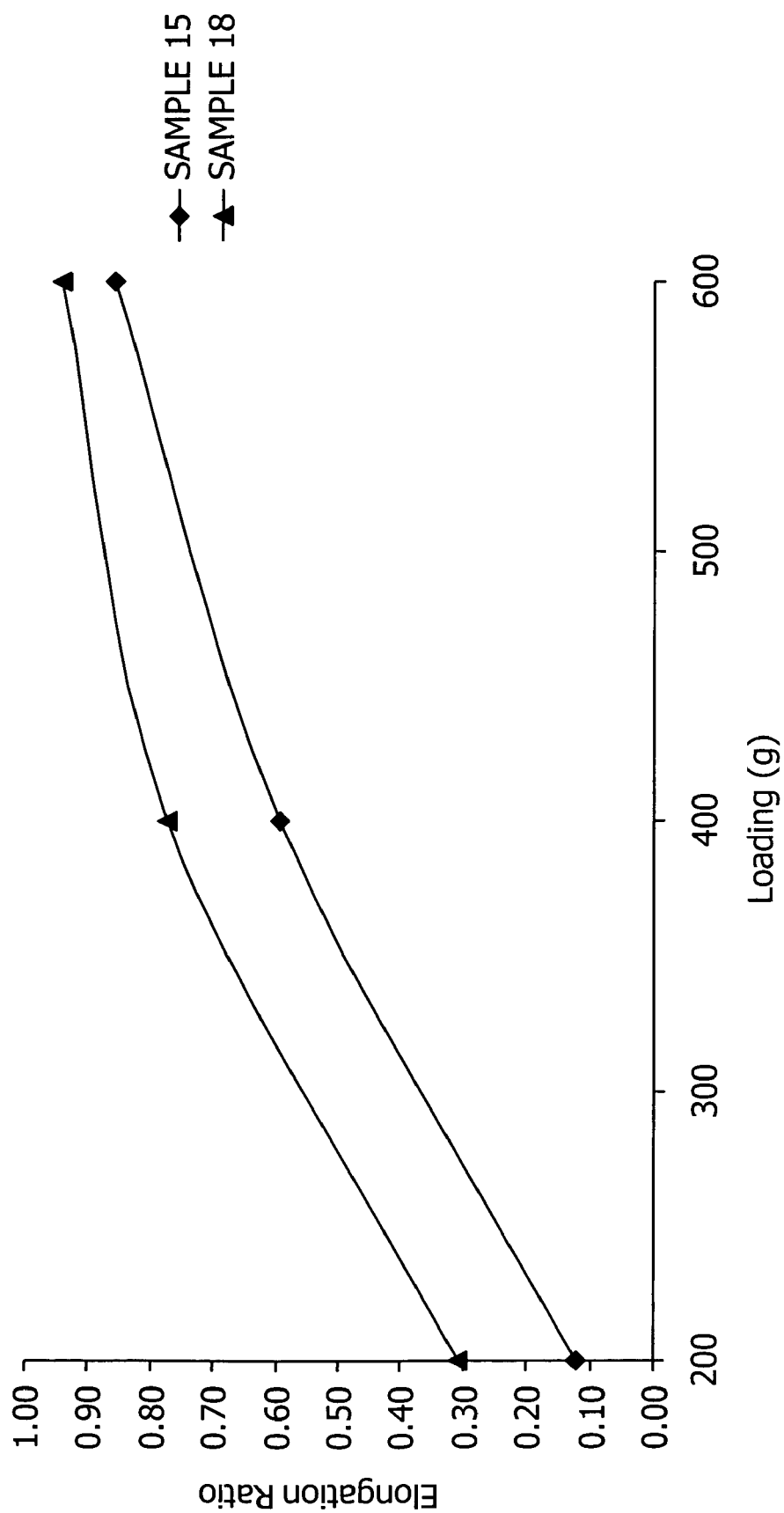

FIG. 41 is a plot showing additional results from the third experiment. This plot compares an Elongation Ratio for Samples 15 and 18. The Elongation Ratio for each sample is calculated by dividing the amount of elongation of each sample at a certain load by the amount of elongation of Sample 14, taken from the non-attachment zone of the composite, at the same load. The Elongation Ratio compares the amount of elongation in the attachment zone of the composite with the amount of elongation in the non-attachment zone of the composite at the same tension. An Elongation Ratio of 1.0 corresponds to an equal amount of elongation in the attachment zone and non-attachment zone of the composite and would correspond to an equal lateral stretch distribution across the composite. As shown in FIG. 41, the Elongation Ratio of Sample 18 was significantly higher than the Elongation ratio of Sample 15 across the range of tensile forces in the experiment. This result shows that the absorbent structure having slits passing through the top waist region and bottom waist region would have improved lateral stretch distribution.

EXPERIMENT 4

A fourth experiment was performed using the Material Elongation Tensile Test, as described later herein, to test the variability of the data from the previous experiments based on the size of the samples. In this experiment, three groups of test samples were tested using the Material Elongation Tensile Test with each sample having at least a 3 to 1 ratio of length to width. The samples were cut from a rectangular shaped composite similar to the composite used in Experiment 3 in that the composite comprised a stretchable outer cover and stretchable bodyside liner having an absorbent structure disposed therebetween and adhered to both the liner and outer cover. As in the previous experiment, the composite included a portion having absorbent structure between the outer cover and liner that formed an attachment zone of the composite and a portion having the outer cover adhered directly to the liner that formed a non-attachment zone of the composite free from absorbent structure between the outer cover and liner. The materials used in the outer cover, liner and absorbent structure of the composite for this experiment were identical to the materials described above for the previous experiments.

The samples tested in the fourth experiment consisted of three groups of samples (Groups I, II, and II), each group having a different length and width but maintaining the preferred 3 to 1 gage length to width ratio. Group I consisted of four 1 inch (25 mm)×5 inch (125 mm) samples (Samples 19-22) having a gage length of 3 inches (76 mm). Sample 19 comprised a strip of stretchable coform absorbent removed from the outer cover and liner of the composite. Sample 20 comprised a strip of stretchable outer over and liner from the non-attachment zone of the composite. Sample 21 was a strip of material from the attachment zone of the composite including the absorbent structure attached to the outer cover and liner. Sample 22 was similar to Sample 21 but included two slits across the width of the absorbent structure spaced approximately 1 inch (25 mm) apart Group II consisted of four 0.5 inch (12.7 mm)×2.5 inch (63.5 mm) samples (Samples 23-26) having a gage length of 1.5 inches (38 mm). Sample 23 comprised a strip of stretchable coform absorbent removed from the outer cover and liner of the composite. Sample 24 comprised a strip of stretchable outer over and liner from the non-attachment zone of the composite. Sample 25 was a strip of material from the attachment zone of the composite including the absorbent structure attached to the outer cover and liner. Sample 26 was similar to Sample 25 but included two slits across the width of the absorbent structure spaced approximately 1 inch (25 mm) apart.

Group III consisted of four 0.25 inch (6 mm)×1.25 inch (32 mm) samples (Samples 27-30) having a gage length of 0.75 inch (19 mm). Sample 27 comprised a strip of stretchable coform absorbent removed from the outer cover and liner of the composite. Sample 28 comprised a strip of stretchable outer cover and liner from the non-attachment zone of the composite. Sample 29 was a strip of material from the attachment zone of the composite including the absorbent structure attached to the outer cover and liner. Sample 30 was similar to Sample 25 but included one slit across the width of the absorbent structure spaced equally from the longitudinal ends of the sample.

Figure 43:
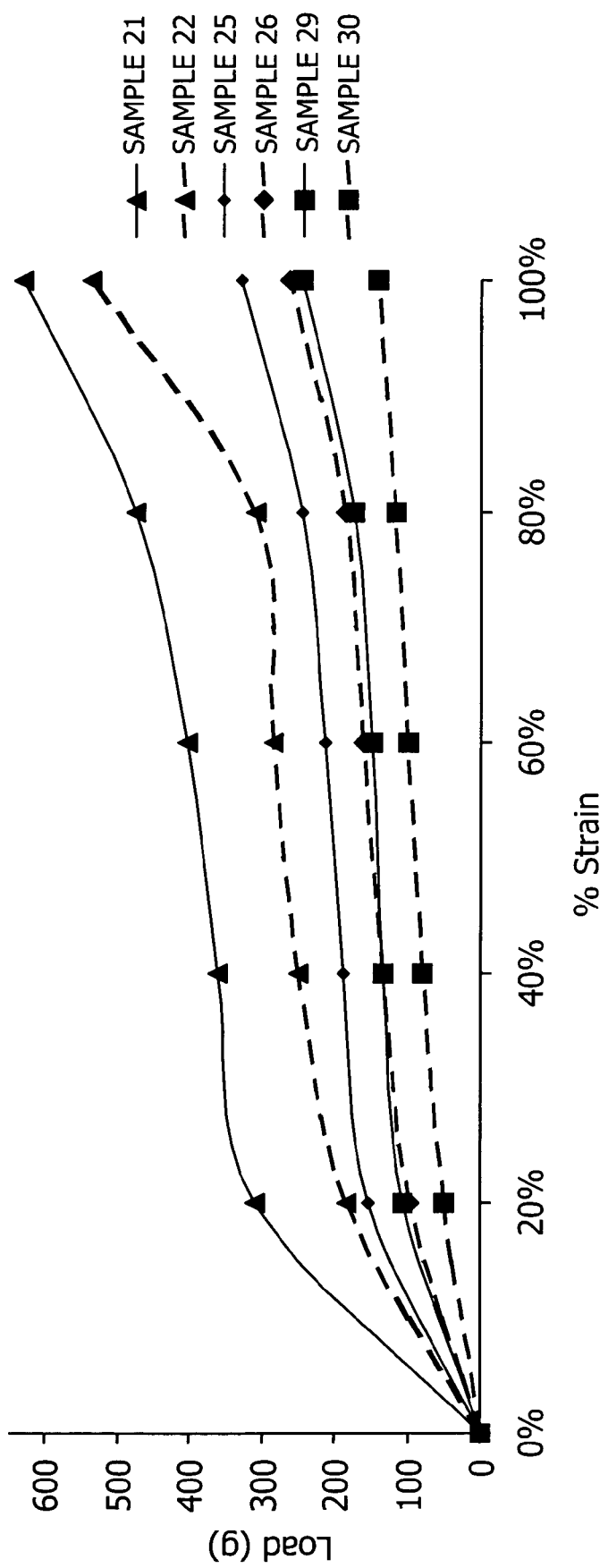
FIGS. 43-45 illustrate test data obtained from a fourth experiment described herein.

FIG. 43 shows the Load versus Strain curve for Samples 21, 22, 25, 26, 29, and 30. The data shown in FIG. 43 shows the general trend that the sample with the absorbent comprising at least one slit for each sample size group had a lower load than the sample having an unmodified absorbent structure of each size group for a given amount of strain.

Figure 44:
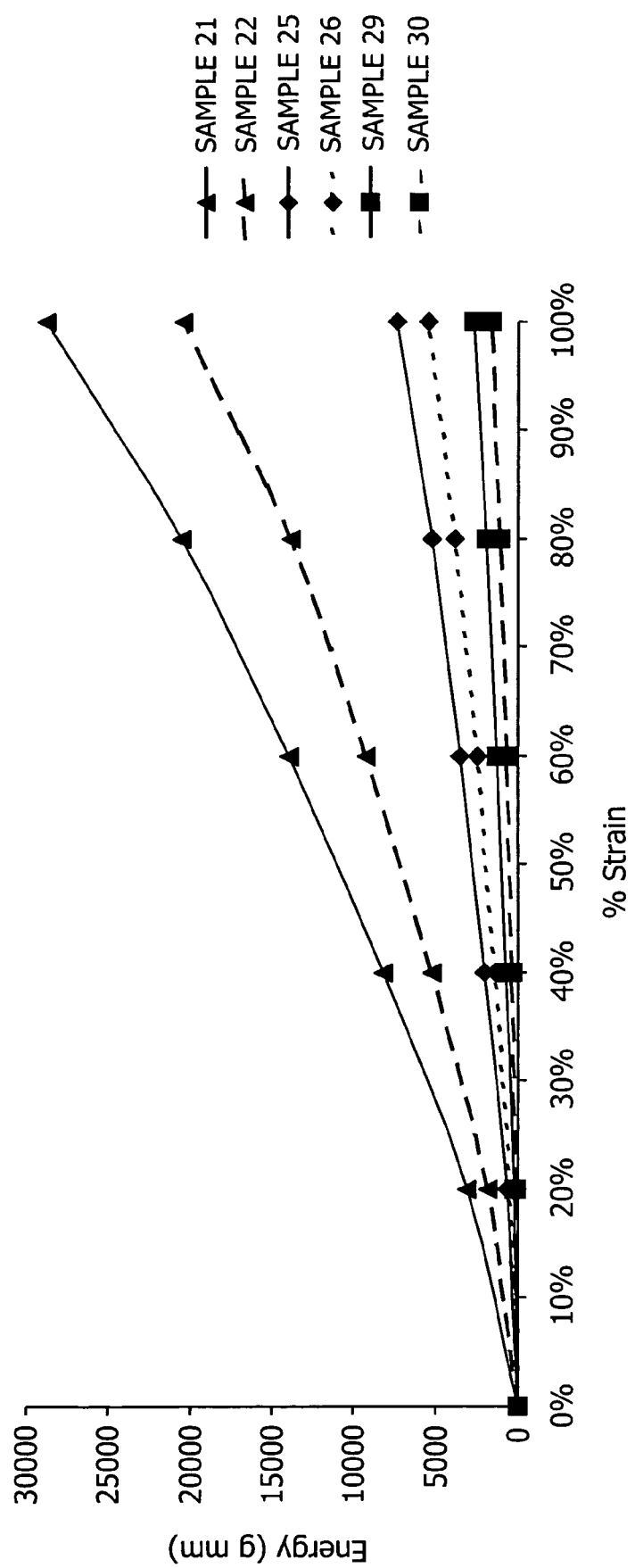

FIG. 44 shows a comparison of the extension energy for each of Samples 21, 22, 25, 26, 29, and 30 versus strain. As discussed above for Experiment 3, the extension energy at a given elongation of the sample is calculated by determining the area under the load versus extension curve up to the amount of elongation for each sample. FIG. 44 shows the general trend that the each sample having a modified absorbent structure including a weakening element (Samples 22, 26, and 30) had a lower extension energy than the corresponding sample of the same size having an unmodified absorbent structure (Samples, 21, 25, and 30, respectively). Because of the various sizes of the samples tested, the results of FIG. 44 also show that the extension energy of an absorbent article having weakening elements is improved (i.e., lower) regardless of the size of the test sample that is examined.

Figure 45:
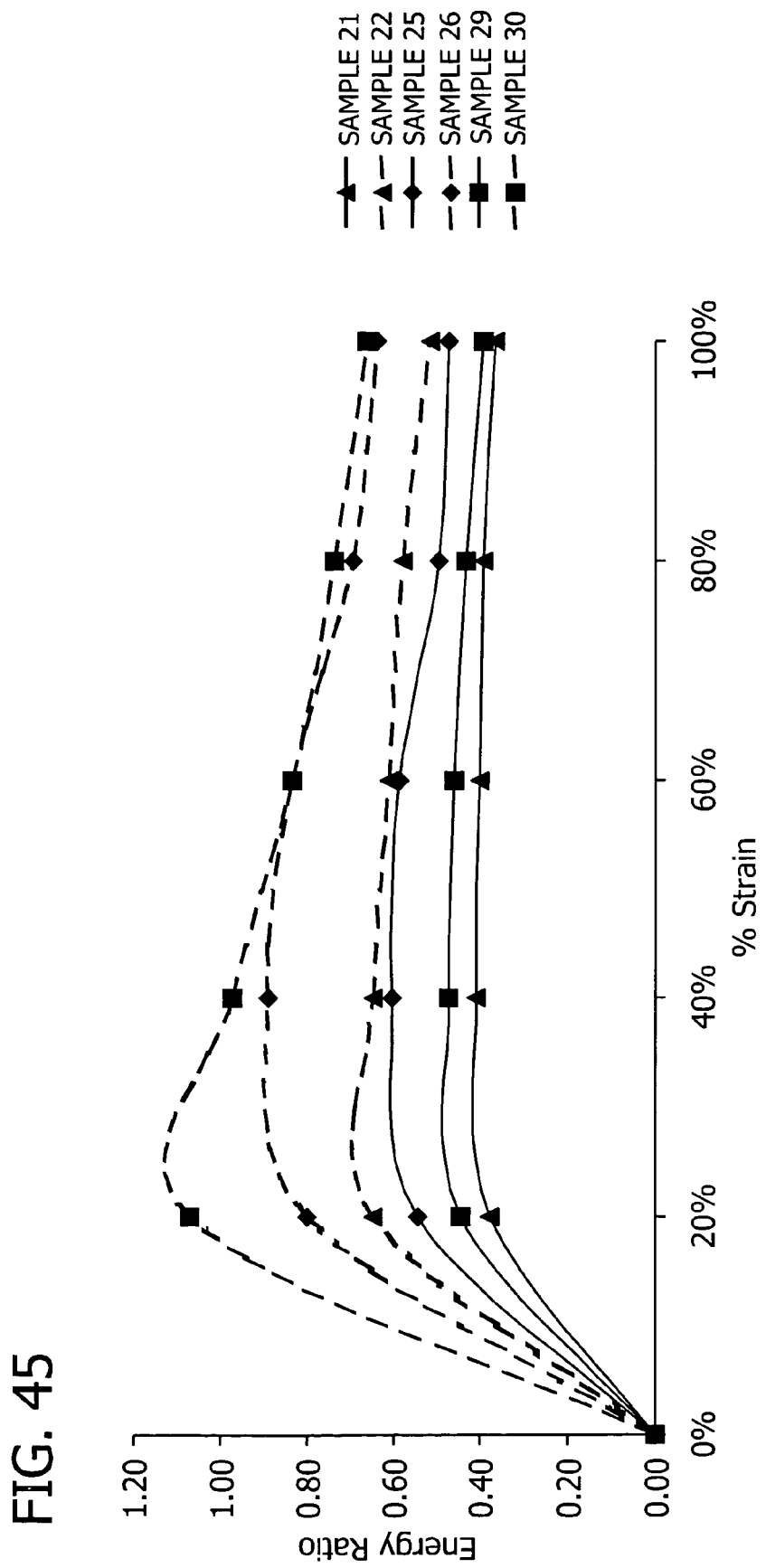

FIG. 45 shows a comparison of the Extension Energy Ratio of each sample taken from the attachment zone of the composite versus strain. As stated above for Experiment 3, the Extension Energy Ratio is a comparison of the amount of extension energy of the non-attachment zone samples of the composite with the amount of extension energy of the attachment zone samples. The Extension Energy Ratio of the attachment zone samples of Groups I, II, and III is calculated by dividing the extension energy value of the non-attachment zone sample of each group at a specific strain by the extension energy of the attachment zone samples of the group at the same strain. For example, the Extension Energy ratio of Sample 21 is calculated by dividing the extension energy of Sample 20 at a specific strain point by the extension energy of Sample 21 at the same strain point. The Extension Energy for Sample 22 would be calculated in a similar manner as the Extension Energy of Sample 21. The Extension Energy of the samples of Group II and III are calculated in a similar manner in that the extension energy of the corresponding attachment zone samples of each group are normalized with the extension energy of the corresponding non-attachment zone sample of the group (Sample 24 and 28, respectively).

FIG. 45 shows the general trend that the samples taken from the attachment zone of the composite having the weakening elements (Samples 22, 26, and 30) had a higher Extension Energy Ratio (closer to 1.0) than the samples that did not have weakening elements (Samples 21, 25, and 30).

MATERIAL ELONGATION TENSILE TEST

For the purposes of the present invention, the measurement of tensile strength and extension of a material or component can be determined by the following specifications and particulars.

Equipment

1. A suitable testing device is a SINTECH constant rate of extension tensile tester (available from MTS Systems Corporation, (a business having offices located in Eden Prairie, Minn.) or an equivalent device. The tensile tester is operatively programmed with suitable software (available from MTS Systems corporation), or an equivalent software.

2. Pneumatic-action grips having a 1 inch (25.4 mm) by 3 inch (76.2 mm) grip face.

3. Test facility having a temperature of 23±6 degrees Celsius, and a relative humidity of 50±10 percent.

The test samples can be cut with a precision cutter (available from Thwing-Albert Company, (a business having offices located in Philadelphia, Pa.) or an equivalent device. The test sample width is perpendicular to the direction of the tensile force applied during the testing. Gage length refers to the distance between the jaws. The sample is clamped in the jaws such that no slippage occurs during elongation of the sample and the 3-to-1 gage length to width ratio of the unstretched sample is present. The moving jaw travels at a constant rate of 250 mm/min. Upon reaching a load of 1 g the test is initiated and the jaw rate of movement changes to 500 mm/min. The gage length at the load of 1 g is the initial gage length in which percent extension calculations are derived. The moving jaw travels a distance equal to 50% of the original 1 g load gage length. Upon 50 percent extension from the initial 1 g gage length, the moving jaw returns to the original 1 g load test initiation position at a rate of 500 mm/min.

The percentage of stretch extension or percent strain can be determined in accordance with the following formula;

$$100*(L-LO)/(LO);$$

where:

LO=gage length at 1 g load, and

L=a distance of extension post test start.

In determining the extensibility or elastomeric nature in a particular of certain materials described herein, such as the outer cover materials, liner materials, and absorbent structure materials, a sample may be taken from a manufactured web or from a finished product. When two samples are intended to test performance of different areas of a finished product (e.g., attachment zone and non-attachment zone), the samples should be taken from the same finished product. Also, the length of the sample should correspond to the lateral direction of the product and the width of the sample should correspond to the longitudinal direction of the sample. Further, when cutting samples from an existing product to test lateral stretch distribution, the samples should be cut from either the front waist region or the back waist region of the product.

Where a sample is prepared from a manufactured web (prior to its incorporation in a product), specimens should be obtained from a segment of the web with consistent and even formation, such as along the midline of the web. The samples should be cut from the web in the orientation as would be found in the finished product. Where the desired materials cannot be obtained from a manufactured web, the sample may be extracted from within the product. Care should be taken to avoid stretching layers during separation. The sample to be separated should be cut to the desired specimen dimensions, or, depending on adhesive chemistry, the sample section may be treated with a solvent selected to dissolve a binding adhesive without affecting the structure or properties of the constituent layers. Each specimen to be tested should be free from attachment to any other auxiliary components that may be present, such as leg, waist and/or flap elastic structures, side panels, etc., at least in the region to be tested. All specimens of a given sample should be tested at the same dimensions.

Where a given material or product will not permit specimens of the desired dimensions to be prepared, the preferred material dimensions selected should have a gage length that is at least three times the sample width. Using the aforementioned SINTECH testing device, the samples may have a width of at least approximately ¼ inch (6 mm) and a gage length of at least approximately ¾" (19 mm). It is contemplated that other machines may be able to test smaller samples in accordance with this testing procedure.

Figure 30:
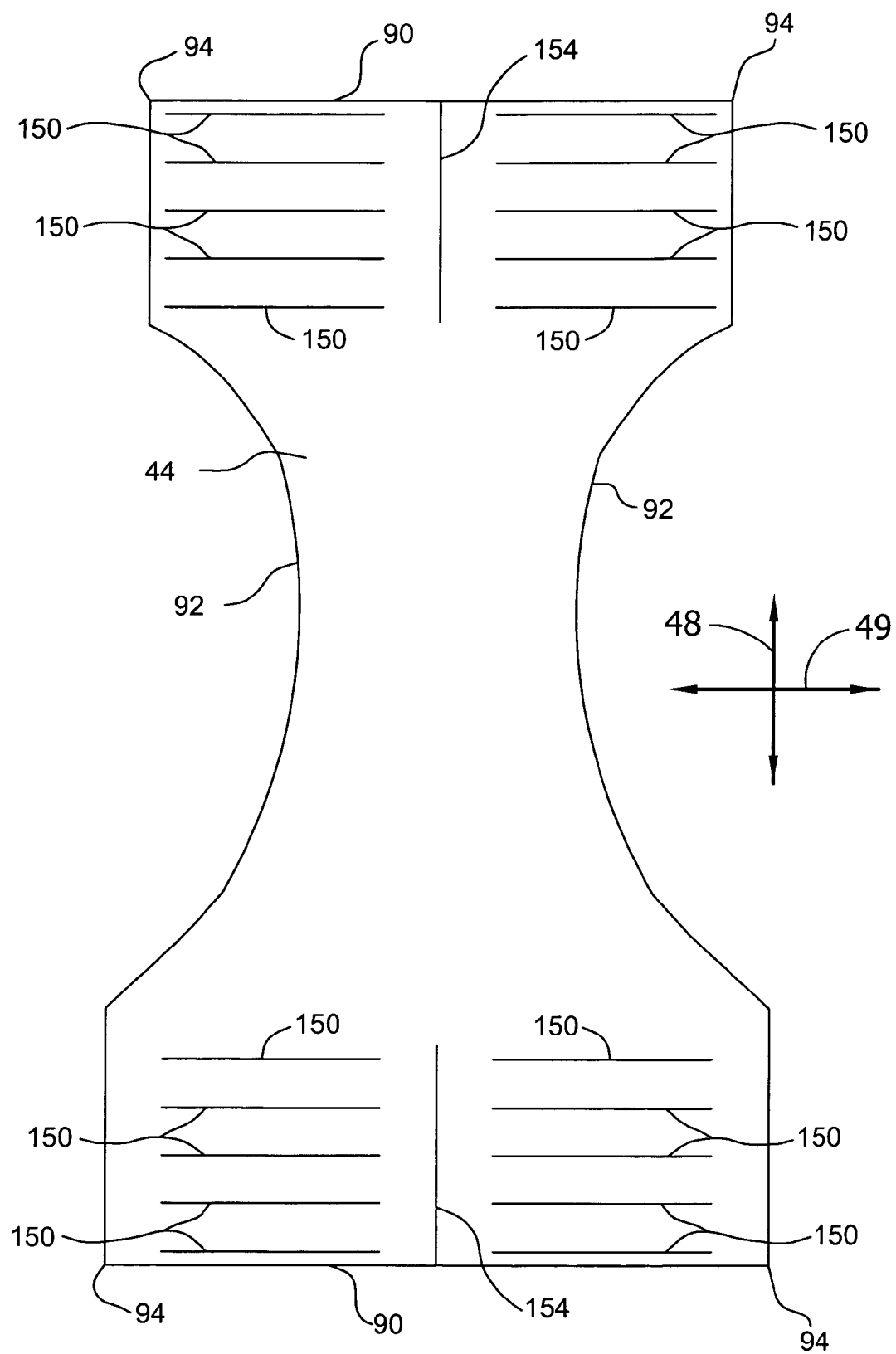
FIG. 30 is a top plan view of an alternative embodiment illustrating an absorbent structure removed from the training pants.
Figure 31:
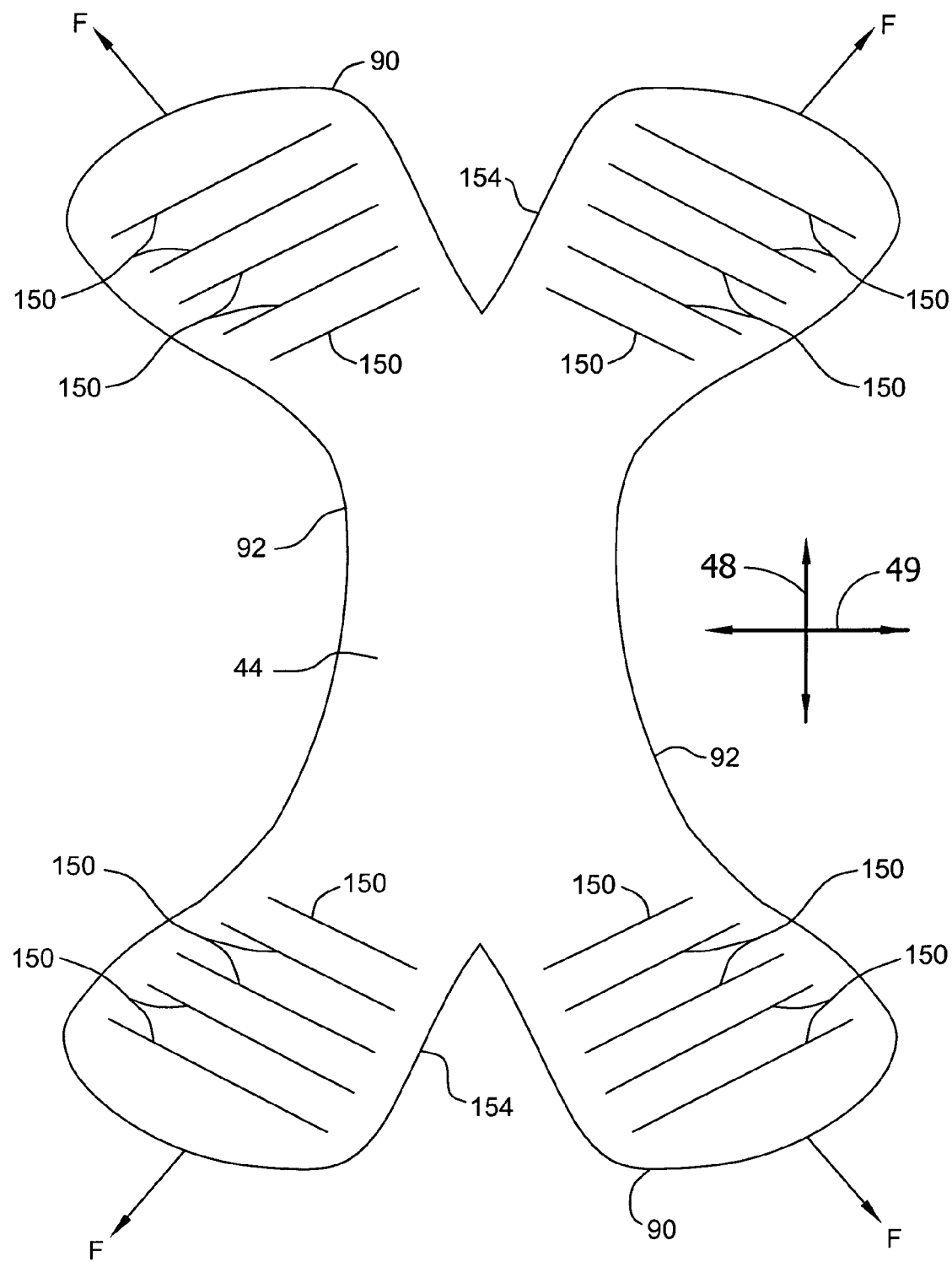
FIG. 31 is a top plan view similar to FIG. 30 but showing the absorbent structure in a stretched condition.
Figure 32:
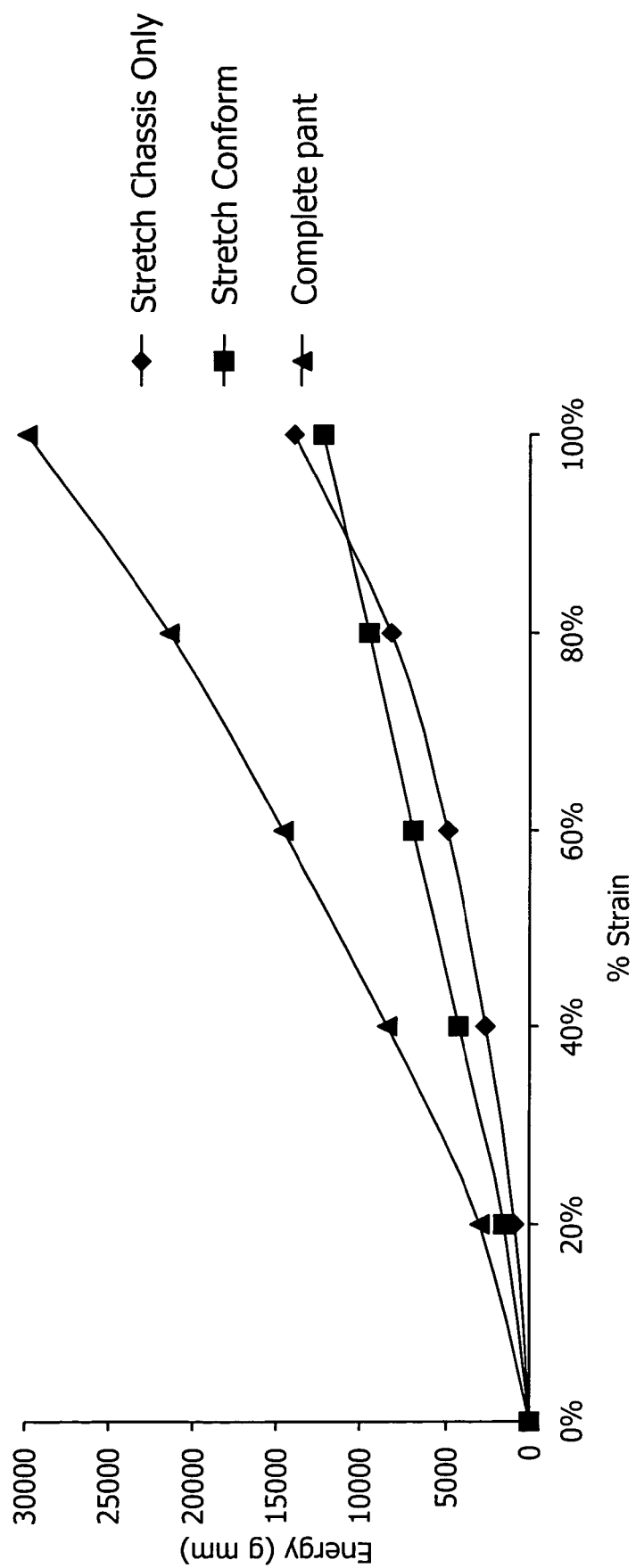
FIG. 32 is a graph comparing extension energy of a complete training pant and two of the training pant components.

FIGS. 30 and 31 illustrate an alternative embodiment of an absorbent structure 44 of the present invention. The absorbent structure 44 is shown removed from the outer cover 40 and bodyside liner 42 but it will be understood that the absorbent structure could be used in any of the previously described embodiments of the absorbent article 20 without departing from the scope of this invention.

Referring to FIG. 30, the absorbent structure 44 is substantially similar to the absorbent structure of the first embodiment except that the absorbent structure includes two spaced apart groups of weakening elements 150 generally near respective corner regions 94 of the absorbent structure. Each of the weakening elements 150 is in the form of a slit oriented in the lateral direction 49 of the article 20 such that each of the slits are substantially parallel. The absorbent structure 44 also has a transverse weakening element 154 in the form of a longitudinal slit disposed generally between each of the two groups of parallel laterally extending slits 150. In the illustrated embodiment each longitudinal slit 154 is located approximately on the longitudinal centerline of the absorbent structure 44 and extends to the longitudinal end 90 of the absorbent structure 44. However, it is understood that each longitudinally extending slit may be offset from the longitudinal centerline of the absorbent structure. Also, the portions of the absorbent structure 44 corresponding to the front waist region 22 and back waist region 24 of the article 20 have an identical arrangement of weakening elements 150, 154 but it will be understood that the absorbent structure may be otherwise configured.

The size, location, and type of parallel weakening elements 150 and transverse weakening elements 154 may vary from what is illustrated in the drawings. As with the previous embodiments, the weakening elements 150, 154 of the absorbent structure 44 may be slits or voids or other suitable weakening elements. For example, the parallel weakening elements 150 may include voids of any size, shape, and orientation and may be located on the longitudinal end 90 or lateral side edge 92 of the absorbent structure. Further, the transverse weakening elements 154 could comprise a void or a series of smaller slits or voids of any size and location without departing from the scope of this invention. It also contemplated that the parallel weakening elements 150 may extend to (e.g. intersect) the transverse weakening elements 154 and remain within the scope of this invention.

As described above, the absorbent structure 44 is subjected to a force F during donning having a magnitude and direction that may vary but is illustrated as being applied in a direction that defines an angle A1. As shown in FIG. 31, the donning force F tends to stretch the absorbent structure 44 of the article in a manner that separates the two corner regions 94 of the front waist region 22 and back waist region 24 at each of the transverse weakening elements 154. When the corner regions 94 are separated, each group of parallel weakening elements 150 become oriented to extend approximately perpendicular to the direction of the donning force F so that the weakening elements substantially reduce the resistance of the absorbent structure 44 to stretching in the direction of the applied donning force.

Figure 42:
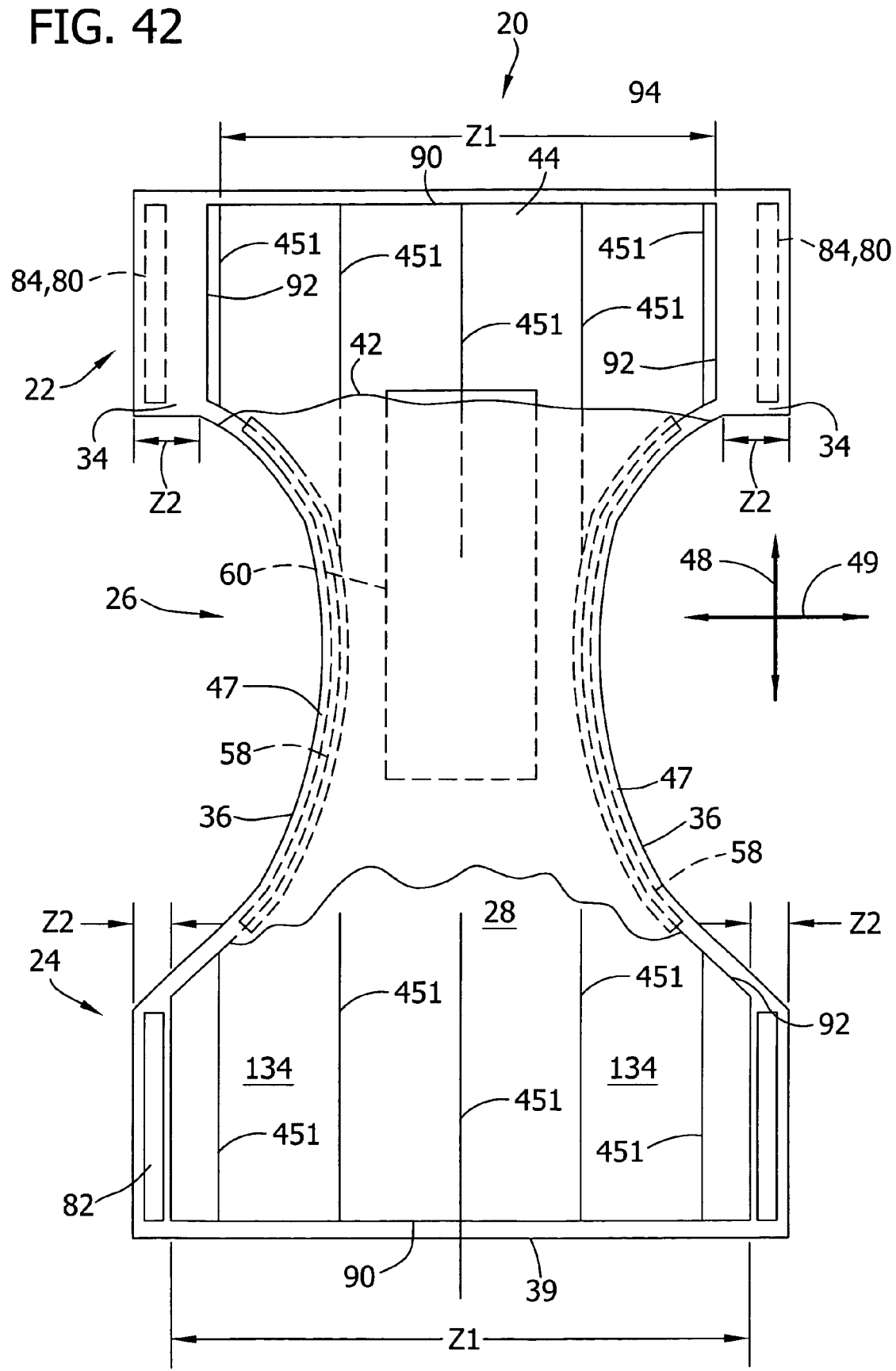
FIG. 42 is a top plan view of an alternate embodiment illustrating an absorbent structure to improve lateral stretch distribution in the article.

The present invention is also directed to an absorbent article 20 having a stretchable absorbent structure 44 that is modified to improve lateral stretch distribution of the article. Typically, the front waist region 22 and back waist region 24 of the article are subjected to stretching in order to increase the circumference of the pant during donning. As shown in FIG. 42, the absorbent article 20 has an absorbent structure 44 that is attached to the outer cover 40 and bodyside liner 42 across the lateral width of the absorbent structure to form an attachment zone Z1 of the article. The article has a side edge margin on both lateral sides of the article comprising the lateral width of the article 20 beyond the absorbent structure 44 that forms a non-attachment zone Z2. In the embodiment of FIG. 42, the absorbent structure 44 is attached to the outer cover 40 and/or bodyside liner 42 by a layer of adhesive (not shown) uniformly covering the surface area of the absorbent structure. In the non-attachment zone Z2 of the article the stretchable outer cover 40 and liner 42 are free from attachment to the absorbent structure 44. In the illustrated embodiment, the article 20 has two non-attachment zones Z2 on each lateral side of the article, but it will be understood that the article may have only one non-attachment zone or the non-attachment zones may be otherwise located without departing from the scope of this invention. Each non-attachment zone Z2 varies in lateral width across the longitudinal length of the article 20 but it is contemplated that the non-attachment zones may be equal width throughout the longitudinal length of the article. Also, the attachment zones Z1 and non-attachment zones Z2 in the front and back waist region may have the different or same dimensions without departing from the scope of this invention.

The attachment zone Z1 of the article 20 is defined by the lateral width between the two outermost points of attachment of the absorbent structure 44 to the outer cover 40 and/or liner 42. In the embodiment of FIG. 42 the absorbent structure 44 is attached to the outer cover 40 and liner 42 across the entire lateral width of the absorbent structure so that the width of the attachment zone Z1 equals the width of the absorbent structure.

Figure 42A:
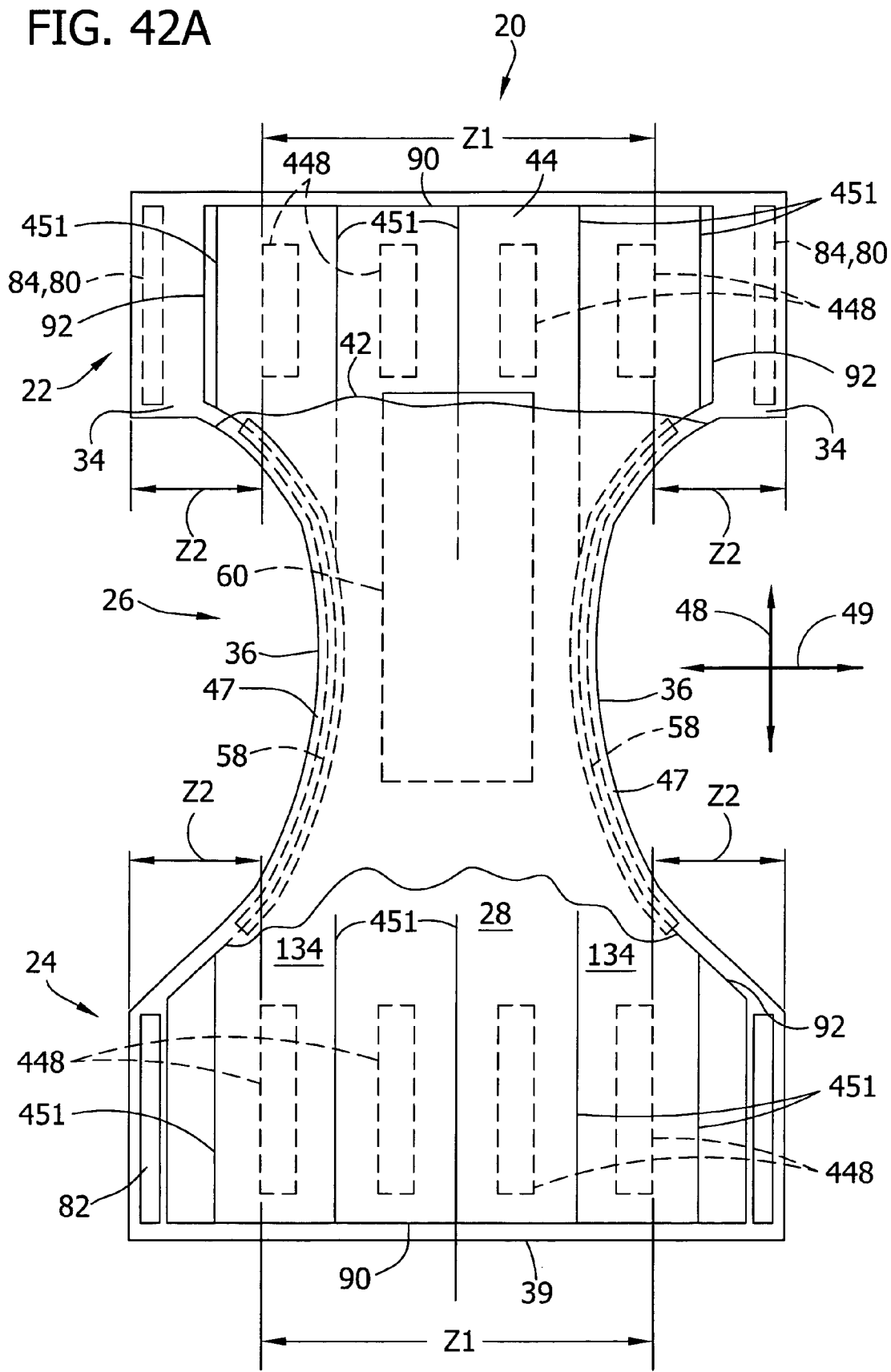
FIG. 42A is a view similar to FIG. 42 but showing an alternative embodiment of the article.

FIG. 42A shows an embodiment of an absorbent article 20 having an attachment zone Z1 that is less than the maximum lateral width of the absorbent structure 44. The absorbent structure 44 is attached to the outer cover 40 by a series of adhesive strips 448 between the absorbent structure and outer cover. It will be understood that adhesive strips similar to strips 448 may be used to attach the absorbent structure 44 to the bodyside liner 42 or that different adhesive configurations may be used between the absorbent structure and the outer cover 40 and liner. As shown in FIG. 42A, the attachment zone Z1 of the article 20 is the lateral width between the two outermost adhesive strips 448. Therefore, each non-attachment zone Z2 comprises the lateral width between each outermost adhesive strips 448 and a respective lateral side edge 47 of the article 20. In the embodiment of FIG. 42A, each portion of the absorbent structure 44 that is laterally beyond each of the outermost adhesive strips 448 would be in the non-attachment zone Z2 of the article 20. It will be understood that the absorbent structure 44 could be attached to the outer cover 40 and/or body side liner 42 by other than adhesive strips, e.g., using points of adhesives, swirls of adhesives, thermal bonding, pressure bonding and ultrasonic bonding, without departing from the scope of this invention.

In the embodiments of FIGS. 42 and 42A, the training pants 20 have weakening elements in the form of five slits 451 arranged in the longitudinal direction of the article 20 spaced equally across the attachment zone Z1 of the article at the front waist region 22 and back waist region 24 of the article. Preferably, the slits 451 extend to (e.g., intersect) the longitudinal ends 90 of the absorbent structure 44 and extend a sufficient length along the entire respective front waist region 22 and back waist region 24 of the article. It is contemplated that slits 451 may be located in only one of the front waist region 22 or back waist region 24 or both of the regions or that the slits may extend into the crotch region 26 of the article without departing from the scope of this invention.

The longitudinal weakening elements 451 act to increase the amount of elongation of the absorbent zone Z1 of the article 20 during donning so that the elongation needed to increase the waist opening 50 is more evenly distributed across the lateral width of the article 20. The longitudinal weakening elements 451 may be any of the weakening elements discussed above for the previous embodiments (e.g., slits, voids or other suitable weakening elements) without departing from the scope of this invention. The weakening elements 451 improve the lateral stretch distribution of the article 20 by increasing the stretchability of the attachment zone Z1 of the article so that the amount of stretch in the attachment zone is closer to the amount of stretch in the non-attachment zone Z2 of the article.

When introducing elements of the present invention or the preferred aspect(s) thereof, the articles "a", "an", "the", and "said" are intended to mean that there are one or more of the elements. The terms "comprising," "including", and "having" are intended to be inclusive and mean that there may be additional elements other than the listed elements.

As various changes could be made in the above constructions without departing from the scope of the invention, it is intended that all matter contained in the above description or illustrated in the accompanying drawings shall be interpreted as illustrative and not in a limiting sense.

What is claimed is:

1. An absorbent article having a longitudinal axis, a lateral axis, a front waist region, a back waist region, and a crotch region extending longitudinally between and interconnecting said front and back waist regions, said article comprising:
   an outer cover stretchable in at least the lateral direction;
   a liner in opposed relationship with the outer cover and stretchable in at least the lateral direction; and
   an absorbent structure disposed between the liner and the outer cover and extending from the crotch region to at least one of the front waist region and the back waist region of the article;
   the article having an attachment zone within which the absorbent structure is secured to at least one of the liner and the outer cover, and at least one non-attachment zone, laterally adjacent the attachment zone, within which the absorbent structure is free from securement to the liner and the outer cover, the absorbent structure having at least one weakening element disposed therein at least in part within the attachment zone of the article and configured to reduce a resistance of the absorbent structure within said attachment zone to stretching in at least the lateral direction;
   said absorbent article having a ratio of lateral extension energy in the non-attachment zone to the lateral extension energy in the attachment zone as determined by a Material Elongation Test, said lateral extension energy ratio being greater than a lateral extension energy ratio of an identically constructed absorbent article but with the absorbent structure being free from said at least one weakening element.

2. The absorbent article set forth in claim 1 wherein the at least one weakening element disposed in the absorbent structure extends in the longitudinal direction of the article.

3. The absorbent article set forth in claim 2 wherein the at least one weakening element comprises an elongate slit disposed in the absorbent structure and extending at least partially therethrough.

4. The absorbent article set forth in claim 3 wherein said at least one weakening element comprises five longitudinal slits disposed in the absorbent structure and extending at least partially therethrough.

5. The absorbent article set forth in claim 4 wherein said five longitudinal slits are evenly spaced across the lateral width of the article.

6. The absorbent article set forth in claim 3 wherein said elongate slit is located in one of the front waist region and the back waist region of the article.

7. The absorbent article set forth in claim 2 wherein the at least one weakening element comprises an elongate void disposed in the absorbent structure and extending at least partially therethrough.

8. The absorbent article set forth in claim 7 wherein the void is generally elliptical.

9. The absorbent article set forth in claim 2 wherein the at least one weakening element comprises a non-linear slit disposed in the absorbent structure and extending at least partially therethrough.

10. An absorbent article having a longitudinal axis, a lateral axis, a front waist region, a back waist region, and a crotch region extending longitudinally between and interconnecting said front and back waist regions, said article comprising:
    an outer cover stretchable in at least the lateral direction;
    a liner in opposed relationship with the outer cover and stretchable in at least the lateral direction; and
    an absorbent structure disposed between the liner and the outer cover and extending from the crotch region to at least one of the front waist region and the back waist region of the article;
    the article having an attachment zone within which the absorbent structure is secured to at least one of the liner and the outer cover, and at least one non-attachment zone, laterally adjacent the attachment zone, within which the absorbent structure is free from securement to the liner and the outer cover, the absorbent structure having at least one weakening element disposed therein at least in part within the attachment zone of the article and configured to reduce a resistance of the absorbent structure within said attachment zone to stretching in at least the lateral direction;
    said absorbent article having a ratio of lateral elongation in the attachment zone to lateral elongation in the non-attachment zone as determined by a Material Elongation Test, said lateral elongation ratio being greater than a lateral elongation ratio of an identically constructed absorbent article but with the absorbent structure being free from said at least one weakening element.

11. The absorbent article set forth in claim 10 wherein the at least one weakening element disposed in the absorbent structure extends in the longitudinal direction of the article.

12. The absorbent article set forth in claim 11 wherein the at least one weakening element comprises an elongate slit disposed in the absorbent structure and extending at least partially therethrough.

13. The absorbent article set forth in claim 12 wherein said at least one weakening element comprises five longitudinal slits disposed in the absorbent structure and extending at least partially therethrough.

14. The absorbent article set forth in claim 13 wherein said five longitudinal slits are evenly spaced across the lateral width of the article.

15. The absorbent article set forth in claim 12 wherein said elongate slit is located in one of the front waist region and the back waist region of the article.

16. The absorbent article set forth in claim 11 wherein the at least one weakening element comprises an elongate void disposed in the absorbent structure and extending at least partially therethrough.

17. The absorbent article set forth in claim 16 wherein the void is generally elliptical.

18. The absorbent article set forth in claim 11 wherein the at least one weakening element comprises a non-linear slit disposed in the absorbent structure and extending at least partially therethrough.

19. The absorbent article set forth in claim 1 wherein the lateral extension energy ratio of said article having at least one weakening element is at least approximately 0.4 for a strain ranging from about 20% to approximately 80% as measured by the Material Elongation Tensile Test.

20. The absorbent article set forth in claim 10 wherein the lateral elongation ratio of said article is at least approximately 0.3 for a tensile force of about 200 grams as measured by the Material Elongation Tensile Test.

21. The absorbent article set forth in claim 1 wherein the at least one weakening element disposed within the attachment zone of the article further comprises at least two weakening elements that are separate from each other and spaced longitudinally from each other.

22. The absorbent article set forth in claim 21 wherein at least one of said weakening elements is disposed at least in part within the front waist region of the article and at least one other of said weakening elements is separate from said at least one of said weakening elements and disposed at least in part within the back waist region of the article.

23. The absorbent article set forth in claim 1 wherein the absorbent structure is of a single-piece construction.

* * * * *